US009670543B2

(12) United States Patent
Germino et al.

(10) Patent No.: US 9,670,543 B2
(45) **Date of Patent: *Jun. 6, 2017**

(54) DETECTION AND TREATMENT OF POLYCYSTIC KIDNEY DISEASE

(71) Applicant: The Johns Hopkins University School of Medicine, Baltimore, MD (US)

(72) Inventors: Gregory G. Germino, Chevy Chase, MD (US); Terry J. Watnick, Chevy Chase, MD (US); Bunyong Phakdeekitcharoen, Bangkok (TH)

(73) Assignee: The Johns Hopkins University School of Medicine, Baltimore, MD (US)

( * ) Notice: Subject to any disclaimer, the term of this patent is extended or adjusted under 35 U.S.C. 154(b) by 562 days.

This patent is subject to a terminal disclaimer.

(21) Appl. No.: 13/965,083

(22) Filed: Aug. 12, 2013

(65) Prior Publication Data

US 2014/0037652 A1 Feb. 6, 2014

Related U.S. Application Data

(63) Continuation of application No. 11/485,062, filed on Jul. 11, 2006, now Pat. No. 8,530,161, which is a continuation of application No. 09/904,968, filed on Jul. 13, 2001, now Pat. No. 7,553,644.

(60) Provisional application No. 60/283,691, filed on Apr. 13, 2001, provisional application No. 60/218,261, filed on Jul. 13, 2000.

(51) Int. Cl.
*C12Q 1/68* (2006.01)

(52) U.S. Cl.
CPC ..... *C12Q 1/6883* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 5,472,672 | A | 12/1995 | Brennan | |
| 5,474,796 | A | 12/1995 | Brennan | |
| 5,654,170 | A | 8/1997 | Klinger et al. | |
| 5,837,832 | A | 11/1998 | Chee et al. | |
| 6,031,088 | A | 2/2000 | Somlo et al. | |
| 6,071,717 | A | 6/2000 | Klinger et al. | |
| 6,225,450 | B1 | 5/2001 | Koster | |
| 6,234,964 | B1 | 5/2001 | Iliff | |
| 6,288,591 | B1 | 9/2001 | Riccio | |
| 6,297,010 | B1 | 10/2001 | Stefano | |
| 6,362,326 | B1 | 3/2002 | Sathe et al. | |
| 6,380,360 | B1 | 4/2002 | Harris et al. | |
| 6,485,960 | B1 | 11/2002 | Harris et al. | |
| 6,656,681 | B1 | 12/2003 | Harris et al. | |
| 7,553,644 | B2 * | 6/2009 | Germino .............. | C12Q 1/6883 435/6.1 |
| 8,530,161 | B2 * | 9/2013 | Germino .............. | C12Q 1/6883 435/6.1 |

FOREIGN PATENT DOCUMENTS

| | | |
|---|---|---|
| WO | WO-95/18225 | 7/1995 |
| WO | 96/12033 A1 | 4/1996 |
| WO | WO-97/40165 | 10/1997 |
| WO | 97/44457 A1 | 11/1997 |

OTHER PUBLICATIONS

Watnick et al. 1999 (American J Hum Genet. 65:1561-1571, 1999).*
Watnick et al. 1998 (Am. J. Hum. Genet. 65:1561-1571).*
Thomas et al. (Am. J. Hum. Genet. 65:39-49) (1999).*
GenBank record Human autosomal dominant polycystic kidney disease protein 1 (PKD1), gene, (Accession: U24498, Version: U24498.1 GI:794297, May 5, 1995, eleven pages).*
GenBank record *Homo sapiens* Chromosome 16 BAC clone CIT987-SKA-13F4 ~complete genomic sequence, complete sequence. (Accession: AC002039 Version: AC002039.1 GI:2342716, Aug. 25, 1997, 34 pages).*
Bogdanova, Nadia et al., "Homologues to the First Gene for Autosomal Dominant Polycystic Kidney Disease are Pseudogenes," Genomics, vol. 74, 2001, pp. 333-341.
Boletta, Alessandra et al., "Polycystin-1, the Gene Product of PKD1, Induces Resistance to Apoptosis and Spontaneous Tubulogenesis in MDCK Cells," Molecular Cell, vol. 6, Nov. 2000, pp. 1267-1273.
Buck et al., "Design strategies and performance of custom DNA sequencing primers", Biotechniques, 27(3):528-536 (1999).
Liu, Wanguo, et al., "Denaturing High Performance Liquid Chromatography (DHPLC) Used in the Detection of Germline and Somatic Mutations," Nucleic Acids Research, vol. 26, No. 6, pp. 1396-1400, 1998.
Neophytou, et al., "Detection of a novel nonsense mutation and an intragenic polymorphism in the PKD1 gene of a Cyproit family with autosomal dominant polycystic kidney disease," Human Genet 98: 437-442 (1996).
Peral, et al., "Screening the 3' Region of the Polycystic Kidney Disease 1 (PKD1) Gene Reveals Six Novel Mutations," Am. J. Human Genet. 58: 86-96 (1996).
Perrichot, et al., "DGGE Screening of PKD1 gene reveals novel mutations in a large cohort of 146 unrelated patients," Hum Genet 105: 231-239 (1999).
Phakdeekitcharoen, Bunyong et al., "Mutation Analysis of the Entire Replicated Portion of PKD1 Using Genomic DNA Samples," J Am. Soc. Nephrol., vol. 12, 2001, pp. 955-963.
Phakdeekitcharoen, Bunyong et al., "Thirteen Novel Mutations of the Replicated Region of PKD1 in an Asian Population," Kidney International, vol. 58, 2000, pp. 1400-1412.
Roelfsema, et al., "Mutation Detection in the Repeated Part of the PKD1 Gene," Am. J Hum. Genet. 61: 1044-1052 (1997).
Rossetti, Sandro et al., "Mutation Analysis of the Entire PKD1 Gene: Genetic and Diagnostic Implications," *Am. J. Hum. Genet.*, vol. 68, 2001, pp. 46-63.

(Continued)

*Primary Examiner* — Juliet Switzer
(74) *Attorney, Agent, or Firm* — DLA Piper LLP (US)

(57) ABSTRACT

Compositions useful for examining the PKD1 gene are provided. In addition, methods for detecting mutations of the PKD1 gene, which can be associated with autosomal dominant polycystic kidney disease in humans, are provided. Methods for diagnosing a mutant PKD1 gene sequence in a subject also are provided, as are methods of treating a subject having a PKD1-associated disorder.

6 Claims, 2 Drawing Sheets

(56) References Cited

OTHER PUBLICATIONS

Rossetti, Sandro et al., "The Position of the Polycystic Kidney Disease 1 (PKD1) Gene Mutation Correlates With the Severity of Renal Disease," *J. Am. Soc. Nephrol*, vol. 13, 2002, pp. 1230-1237.

Shapira et al., "Deletional switch recombination occurs in interleukin-4-induced isotype switching to IgE expression by human B cells", *PNAS*, 88(17):7528-7532 (1991).

The European Polycystic Kidney Disease Consortium, "The Polycystic Kidney Disease 1 Gene Encodes a 14 kb Transcript and Lies within a Duplicated Region on Chromosome 16," *Cell*, vol. 77, Jun. 17, 1994, pp. 881-894.

Thomas et al., "Identification of Mutations in the Repeated Part of the Autosomal Dominant Polycystic Kidney Disease Type 1 Gene, PKD1, by Long-Range PCR," *Am. J. Hum. Genet*. 65: 39-49 (1999).

Turco et al., "A novel nonsense mutation in the PKD1 gene (C3817T) is associated with autosomal dominant polycystic kidney disease (ADPKD) in a large three-generation Italian family," *Human Molecular Genetics*, 4(8):1331-1335 (1995).

Underhill, Peter A., et al., Detection of Numerous Y Chromosome Biallelic Polymorphisms by Denaturing High-Performance Liquid Chromatography, Genome Research, vol. 7, pp. 996-1005, 1997.

Watnick, Terry et al., "Mutation Detection of PKD1 Identifies a Novel Mutation Common to Three Famalies with Aneurysms and/or Very-Early-Onset Disease," Am. J. Hum. Genet., vol. 65, 1999, pp. 1561-1571.

Watnick, Terry J. et al., "An Unusual Pattern of Mutation in the Duplicated Portion of PKD1 is Revelaed by Use of a Novel Strategy for Mutation Detection," *Human Molecule Genetics*, vol. 6, No. 9, 1997, pp. 1473-1481.

Watnick, Terry J. et al., "Somatic Mutation in Individual Liver Cysts Supports a Two-Hit Model of Cystogenesis in Autosomal Dominant Polycystic Kidney Disease," Molecular Cell, vol. 2, Aug. 1998, pp. 247-251.

Watnick, Terry J., "Gene Conversion is a Likely Cause of Mutation in PKD1," Human Molecular Genetics, vol. 7, No. 8 1998, pp. 1239-1243.

GenBank record having Accession No. L39891.1 (GI: 790818), published Jun. 19, 1995.

Communication from Canadian Patent Office from application No. CA 2,697,031.

Bogdanova et al., "Screening the 3' region of the polycystic kidney disease 1 (PKD1) gene in 41 Bulgarian and Australian kindreds reveals a prevalence of protein truncating mutations", Hum. Mutat., 16(2):166-74 (2000).

Ward, C.J. et al.: "*The polycystic kidney disease 1 gene encodes a 14 kb transcript and lies within a duplicated region on chromosome 16*"; The European Polycystic Kidney Disease Consortium [published erratum appears in Cell Aug. 26, 1994;78(4):following 724]. Cell, 77(6),1994, p. 881-894.

* cited by examiner

SEQUENCE LISTING

```
<160> NUMBER OF SEQ ID NOS: 113

<210> SEQ ID NO 1
<211> LENGTH: 53522
<212> TYPE: DNA
<213> ORGANISM: Homo sapiens

<400> SEQUENCE: 1

tgtaaacttt ttgagacagc atctcaccct gttccccagg ctggagtgca gtggtgtgat      60

catggctcac tgcagcgtca acctcctggg tctacttgat ctgtaaactt cgagggaagg     120

tgtaataaac cctcctgcaa tgtctttgtt tttcaaaatc tttgtatttc acagtttagc     180

ttcgtgggtt gatgttctat tttgtttttg tgtgtgtgtg tgtgtgtttt gtgttttttt     240

ttgagacaca gtcttgctct tgttgcccag gctggagtgc aatggtgtga tcttggctca     300

ctgcaacttc cacctcttgg gttcaagaga ttctcctgcc tcagccttcc gagtagctag     360

gattacaggc gccgccacca caccccgcta attttgtatt tttagtagag atggggtttc     420

tccatattgg tcaggctggt ctcaaactcc cgacctcagg tgatccgccc acctcagcct     480

cccaaaatgc tgggattaca ggcgtgagtc accgcacctg gccaatgttc tatttttgag     540

aacacaacag ttcataatat attctacata gaccatacct gttatgtgta gataaacaga     600

ctcttttccc atttaacacc ttttgcctta ggtttatttt tctggtatca atactggcac     660

acttactttg tttgcagttt cctgtctttt tttttttttt tttttttttt gagacagagt     720

ctcactctgt cacccaggct ggagtgaagt ggcgggatct cggctcactg caacctctac     780

ctcctgggtt catgcgattc tcctgcctca gcttcccgaa tagctgagac cacaactgtg     840

tgccaccatg cccagccaat ttttgtattt ttagtagaca cggggtttca ccatactggc     900

caggatggct caatctcttg acctcgtgat ccacctgcct ccgcctccca aagtgctggg     960
```

```
attacaggca tgagccactg tgcctggcct tttttttct ttttgagatg gagtctcact   1020
ctgtcaccca ggctggagtg cagtggggta acctcaggtc actgcgacct ccgcctcccg   1080
ggttccagtg attctcctgc ctcagcctcc cgagtagctg ggattacagg cacccaccac   1140
catgcctggc taatttttgt atttttagta gagacggggt tttgccacgt tggccaggtt   1200
ggtctcgaac tcttggcctc atgtgacccg cctgccttgg cctcccaaag tgctgggatt   1260
acaggtgtga gccactgtgc ctggcctggc tttcttgttt cttttctcct cttctagttt   1320
ccccctttta ggctaacaat tattcactgt taataaaaac cctcaggtct gtattttatc   1380
aagaaacatt tccctcacgt cttcttccct gaaccaaaca agatctctgg cacattttat   1440
ttgctctgtc tcaccacatg gattttgttt ttttgtttct ttgtttttttg agatggagtc  1500
tcactcttgt tgcccaggct ggagtgccat ggcacaatct cagctcactg caacctccac   1560
ctcctgggtt caagcgattc tcctgtctca gcctcctgag tagctgggat tacaggcgcg   1620
tggcaccacc cccagctaat ttttgtattt ttagtagaga cggggtttca ccatgttggt   1680
caggctggtc tcgaactcct gaccttgtga tctgcccacc ttggcctccc aaagtgctgg   1740
gattacaggc atgagccacc acgcccggcc cccatggttt ttcaaatagt ttagaatttc   1800
atttccaggt aactaatttg cttctttaaa catatgtctt ttctatttaa gaaatccttt   1860
ctaaacaatt gcattttatt ccacaaccgc cttcaaacaa tcattgagac ttggttaatc   1920
tgttttgctc atttggcagc agtttcttgt ggctgtttct tccctccact ggagtccttg   1980
aatcttaagt ctgtcatttg actgcaatta aaagctgggt ttggaataca atcgcagcct   2040
taccatccac ctgctgtgtg acctggtaaa tttctttttt ttttttgag acggagtctt    2100
gctctgttgc ccaggctgga gtgcagtggc acaacctctg cctcccaggt tcaagcgatt   2160
ctactgcctc aggctcccta gtagctggga ttataggtgc ctgccaccat gcccagctga   2220
tttttgtatt tttagtagag atgaggtttc accatgttgg ctaggctggt ctcgaacttc   2280
tgatcttgtg atctgcccgc ctcggcctcc caaagtgctg ggattacagg catgagccac   2340
cactcccagc cagttctttt tttcttttt ccattttttt ttttttcgag acaggatctt    2400
actcttttgc ccaggcggga gtgcagtggc acaatcacgg ctcagcgcag ccactgccta   2460
ctgggctcac acgctcctcc ggcctcagcc tctcgagtac ctgggactac aagcgtgagc   2520
cagtttggct aattttggct aatttttgta gaaacggggt ctcgccatgt tggccaggct   2580
ggtctccaac tcctggactc aagggatcca ccttcctccc cctctcaaag ttctgggatt   2640
accggagtga gccactgtgc cctgctggca aatttcttaa actgtctgtg cctcagtgac   2700
ctcatttaat aaagggaata attgtagcac actttttcta gagctgtgaa gattcaatgg   2760
aataaataag gcaataaatg aatggatggg gaatgaagga tgtgggtttc ctccctcttg   2820
tctttcaata agctctcacc atcaacctcc cattgcctgt tctctctctt ccccctctct   2880
ccctctgtct ctctctcagc caggaaacct ggggtaggga ggcttggagc cagcgggtgc   2940
gtcgggaggc tgcgggtact gactcgggcc gcgcacggag atcgcgggag aaggatccac   3000
aaccgcggaa gaaggatcag ggtggagcct gtggctgctg caggaggagg aacccgccgc   3060
ctggcccaca ccacaggaga agggcggagc agatggcacc ctgcccaccg cttcccgccc   3120
acgcacttta gcctgcagcg gggcggagcg tgaaaaatag ctcgtgctcc tcggccgact   3180
ctgcagtgcg acggcggtgc ttccagacgc tccgccccac gtcgcatgcg ccccgggaac   3240
gcgtggggcg gagcttccgg aggccccgcc ctgctgccga ccctgtggag cggagggtga   3300
```

-continued

```
agcctccgga tgccagtccc tcatcgctgg cccggtcgcg ctgtggcgaa gggggcggag   3360
cctgcacccg ccccgccccc cctcgccccg tccgccccgc gccgcgcggg gaggaggagg   3420
aggagccgcg gcggggcccg cactgcagcg ccagcgtccg agcgggcggc cgagctcccg   3480
gagcggcctg gccccgagcc ccgagcgggc gtcgctcagc agcaggtcgc ggccgcagcc   3540
ccatccagcc cgcgcccgcc atgccgtccg cgggccccgc ctgagctgcg gcctccgcgc   3600
gcgggcgggc ctggggacgg cggggccatg cgcgcgctgc cctaacgatg ccgcccgccg   3660
cgcccgcccg cctggcgctg gccctgggcc tgggcctgtg gctcggggcg ctggcggggg   3720
gccccgggcg cggctgcggg ccctgcgagc cccccctgcct ctgcggccca gcgcccggcg   3780
ccgcctgccg cgtcaactgc tcgggccgcg ggctgcggac gctcggtccc gcgctgcgca   3840
tccccgcgga cgccacagcg ctgtgagtag cgggcccagc ggcacccggg agaggccgcg   3900
ggacgggcgg gcgtgggcgg gttccctggc ccgggacggg aagcaggacg cgggccagga   3960
cgctcccagg ggcgaggctc cggcgcggca cggcgggccc tgctaaataa ggaacgcctg   4020
gagccgcggt tggcacggcc ccggggagcc gaaaaacccc gggtctggag acagacgtcc   4080
cacccggggg ctctgcagac gccagcgggg gcggggcgcg gaggccgcgc tcagctggga   4140
ggacaaacag tcgctaattg gagaggaatt gggatgcggc ctggggctgc ggggtacccg   4200
gagaggtggg gatggctgta gggggcggca gggaagagtt ccaggaggtg tctggaaaag   4260
gatttgatgg atgtgcaaga attgggctga tgcttaggaa ggggcgatga ggtgggtcca   4320
gaagaagggg ggtgaacggt gtgagcaaag accgtgaggc tggaggctgg ccacgggagg   4380
tgtgaggggt aggggcaggg tgggaggtgg gctcgcgggt gggctggggt catgaagggc   4440
ctcaggcgct ctgctattgg gttccaaggc tatcctgaga acaggggtga ggggggattg   4500
ccgtgggggg ttaaagcctt gtcatgttcg ctttcgggag ataaaaacaa caggtggcct   4560
ttatggagac gctgcccaga gccaggtctg tgccaggctc ctgttggggg tcgtcatgcg   4620
gaatcctgac tctgaccatc cgaggcatag ggaccgtgga gatttgcatt tcacagatga   4680
ggaaacaggt ttggagaggt gacacgacct gtcccaggca tcacagccgg gatgtgcata   4740
gcaggggttt ggaactatga ggtgcccagg acccagggtt ggattgaaaa gggcggaggg   4800
gactaagata agcagacagt tgtccccagc gctggggaga gtcttgggac cagtctgatg   4860
ccttgtattt cccaggctcc aggctcctcg ccgggacagt gtctccttgg gtgcgtgctg   4920
gatccctggg ggacgtggca catccccagg cttgctaaac attgggtggg ttctggcatt   4980
tggttttgta acgtttctgg gtcactcccg cctgtggcca cccttcctta ggggagccgt   5040
gtgtccttgg ggctttgctg ggtggtctcg agggtgggag aagaatgggt tctcctggac   5100
caatggagcc cgtgcccctc ggggccacat tgctcctgcg ctccctgact gcggacgcgt   5160
gtgtctcgcg gctgtctctg tggagatggc ctcctcctgc ctggcaacag cacccacaga   5220
attgcatcag acctacccca cccgttgttt gtgatgctgt agctgagggc tcctctgtct   5280
gccaggccgg tcactgggga ctctgtccag ggcctggtgg ttcctgcttc ccagcacctg   5340
atggtgtcca tgagagcagc ccctcaggag ctgtccggga gagaagggcg ctggtggctg   5400
ctgagcggag agcaaggccc gtgttctcca ggcccttggc acagcagtgg agccccccgcc   5460
cctgccttgt gttgtcctct taggctctgg tcctggggtt tggaggaggg ggaccctggg   5520
agttggtggc ctgtcccagc ctgagctggc aagattccga atgccaggcc ccccaagtgt   5580
gcaacagggc acagggtgac ctcatgtggg caggtgggtg ctgttctgta cacacctggg   5640
gccgccgctg ggagagttct ggaaggtggg gtgaggggac ccatggcaaa ctagggcctt   5700
```

```
aggaaggatg tgaaggccct ggctggcccc ccaggccacc ctctgtgctg tggggcagcc   5760
cagccatttt gctgtctacc ctgcaaactc ctcctcgggg agacggctgg gttttcccca   5820
gggaagaggg gtcaagctgg gagaggtgaa ggacacagat cacagctgct ggcaggtgtt   5880
caagggtcca agagcgttgc tgtctgggtg tcaccagtag ccttcctggg gggctcacgc   5940
aggtgcctct ccacttgtgg ctccctggct gctgaagctc agcagggaca gctgtgtcca   6000
gttccaggtg gaggacagcc ggggcttctg aggccacagc ctgccttggg ttaatgatgc   6060
tgccgagagg tggtggcttt tggaaaagat ggcgtactgc aaaacgtgct gctctgcgtg   6120
gctcgaagct tcgtggggag acgtgggcag agccgtggct gactcacaga ccccccaccc   6180
cagagcctgc cctgccctcc ctgccccgac ccttctccct cctgacccat gtgttttttt   6240
tttttttttt tttttttgag acagagttca ctcttgttgc caaggctgga gtgcaatggc   6300
acgatctcgg ctcatggcaa cctccgcctc ctgggttcaa gcgctttttc ctgcctcagc   6360
ctcccgagta gctgggatta caggcgtgca ccaccatgcc tggctaattt tgtattttta   6420
gtagagacag ggtttctcca tattggtcag gctggtcttg aactcctgac ctcagatgat   6480
ccgcccgcct cggcctccca aagtgctggg attacaggca tgagccacca cgcccagccc   6540
tgacccatgt tttgaaccaa attccagcca cccttttatc tgcaagcatt ttggagggca   6600
tcgcaatact gcagacccac ctaacacaac agacagttcc ttcatgccac cgaaggcctg   6660
gtgtgttcac atttttggtt taatagtttg aattaagagc caaataaggt ccacacactg   6720
caattagttg atgtcttttt ttttttcttt tttttttttt ttttgagacg gagtcttgct   6780
cttgtctcca ggccgcagtg cagtggcatg atctcagctc accgcaacct ccgactccct   6840
ggttcaagcg attctcctgc ctcagcctcc cgagtacctg gtagctgggt ttacaggcat   6900
gcaccaccgt gcccagctaa tttttgtatt tttagtagag acggggtttt actgtgttgg   6960
ccaggatggt ctcgatctcc tgacctcgtg atctgcccac ctcggcctcc caaagtgctg   7020
ggattacagg cgtgagccac cgcacccggc caatgtcttt taaaaatata tacttttttt   7080
ttttttttga gacggagttt cgctcttgtt gcccaggctg gagtgcagtg gcgcgatctc   7140
acctcacggc aacctccgcc tcccgggttc aagtgattct cctgcctcag cctctccagt   7200
agctgggatt acaggcatgt gccaccatgc ctggctaatt ttgtattttt aggagagacg   7260
gggtttctcc acgttggtca ggctggtctc aaactcctga cctcaggtga tccgcctgcc   7320
ttggcctccc aaagtgttgg gattacaggt gtgagccaac gcgcccagac aaaaatatat   7380
gtgtgtcttt aaggctggtc aagcaaagca gtaggactgg agaaagaatg aagaattcta   7440
cctggctgtg atcaattcgt tgtgaacacc actgtgcttg gaccagctag ctgatgtctt   7500
ttgttttgtt ttgtttgaga cggagtctgg ctctgtcacc caggctggag gacaatggtg   7560
tgatctcggc tcactgcagc ctccatctcc cgggttcaag cgattctcct gcctcagcct   7620
cctgagtagc tgggattaga ggcgcgcgcc accacgcccg gctaattttt aaaaatattt   7680
ttagtagaga tggggtttca ccatgttggt caggctggtc ttgaactctt ggccttaggt   7740
gatctgcttg cctcggcctc ccaaagtgct gggattacag gtgtgagtga tgtattttat   7800
ttatttattt atttatttat ttttattatt tgagatggag tctcactctg ttgcccaggc   7860
tggagtgcag cagtgccatc tcagctcact gcaagctccg cctcctgggt tcacgccatt   7920
ctcctgcctc agcctcctga gtagcctgga ctggtgcccg ccaccatgcc cagctaattt   7980
tttgtatttt tagtagagac ggggtttcac cgtgttagcc aggatggtct ggatctcctg   8040
```

-continued

```
acctcgtgat cctcccgcct cagcctccca aagtgctggg attacaggct tgagccaccg   8100
cctgtctttt aaatgtccga tgatgtctag gagcttccct tcctctcttt ttccttgtgc   8160
aatttgttga agaaactggc tcctgcagcc tggatttctc gctgtgtctt gggggtgcca   8220
cctccatggt gtcacctccg tggtgctgtg agtgtgtgct ttgtgtttct tgtaaattgg   8280
tcgttggagc cgacatccca ttgtcccaga ggttgtcctg gctggcactg gcctaggtgt   8340
agatgtcatc agctcagggc cccctgctct aaaggccact tctggtgctg gttgccactc   8400
accctggctg ggggtcacct gggtctgctg ctgtctcgca aatgctgggg tccaggactg   8460
ggcacatcga gggacttggt aggtgcttgg ttcactgatg taaaatatag gagcacccgg   8520
ggccttgccc tttcccacct gcatccctga atgacaggag agtgtgggag agtgtaggga   8580
cagcaggcgc agaccccggg gcccctgcct gggattggcg tcggggaaga caggcattct   8640
ggagcgaccc ctaggcctga tgccttagag cgcaactgcc agagacacag cttccttggg   8700
gggctggcca ggccacggag gggccctggc tcccatttct ggtccctgga tcctgagagc   8760
gaggactagg gattgtcacc aaggcctcca tgagccctca gcagaaggag ggccaccctc   8820
gagggctccg ttatcactgg agcccgcgtt caaccaacac gcagatgatt ctccaaggac   8880
agagatggat gatggggagg gggctggcct ggaaggaccc ccagtgcagg tgacattgaa   8940
gccaggtttc aaagctccca cagggagctg cccagagaga gtccccaagg ggcaaggtga   9000
ctcgggggca ggggtagggc ctctgtcagg agagcctagg agaggcctgt gtcttctagg   9060
aagagccctg gcagccgagc ggaggcagtg gtgaggacct gcatcctgca tgtccagctg   9120
gcctcacccg gggtccctga gccgggtctt acgtggctcc cgcactcggg cgttcagaac   9180
gtgcctgcgt gagaaacggt agtttcttta ttagacgcgg atgcaaactc gccaaacttg   9240
tggacaaaaa tgtggacaag aagtcacacg ctcactcctg tacgcgattg ccggcagggg   9300
tgggggaagg gatggggagg ctttggttgt gtctgcagca gttgggaatg tggggcaccc   9360
gagctcccac tgcagaggcg actgtggaga cagagagcac ctgcaggtca tccatgcagt   9420
atcggcttgc atccagatca tacagggaac actatgattc aacaacagac agggaccccg   9480
tttaaacatg gacaaggggt cactcacgcc tggaatccca gcagtttggg aggccagggt   9540
gggtggatcg cttgagccca ggagtttgac accagcctgg gcaacagggt gagaccccgg   9600
tctctaaaaa ataaaagaac attggccggg cgtggtggta tgcatctgtg gtcccagcta   9660
ttcaggagac tgaggtggga catcacttga gccgaggagg tcaaggctgc agtgagctgt   9720
gatcacacca ctgcactcca ggctgggtca cagagcaaga ccctgtctca aaaaaaaaaa   9780
aaaaaaaaaa aaaaaatcac aggatctgaa cagagatttc tccaaagaag acgcacagat   9840
ggccaacagc gtgtgagaag atggtcggcc tcattagtca tgagggaaac gtaaatcaaa   9900
accactgtcc agccgggcgc ggtgcctcac gcctgtaatc ccagcacttt aggagagcag   9960
atggcttgag gccaggagtt tgaggccagc ctgggcaaca tagcgagacc aataaataga  10020
tattagtggt ggcgcctgta gtcccagcta gttgggaggc tgagggggga ggattccctg  10080
agtctatgag gttgagactg cagttagctg tgatggtgcc actgcactcc agcctgggcg  10140
actaggaaac ggtctttaaa aaaaaaaaaa aaaaacaggg tgggcgcggt ggttcacgcc  10200
tgtaatctca gcactttggg aggccaaggt ggggggatca caaggtcagg agtttgtgac  10260
cagcctgacc aacatggtga aaccccgttc tactaaaaat acaaaaatta gcgaggtgtg  10320
gtcgtgggcg cctgtaatcc cagctaatta ggaggctgag gcaggagaat cacttgaacc  10380
cgggaggcgg aggttgcagt gagccaatat cacaccactg cactctagcc tggtcaacag  10440
```

agcgagactc tgtctcaaaa aaaaaaaatg ctgagcgtgg tggcgcatgc ctgtagtctc 10500
agctactttg ggggctgagg caggagaatc gcttgaacct gggaggcaga ggtcgcagtg 10560
aggcaagatt gcaccattgc actccagcct gggagacaga gtgaaactct gtctcaaaaa 10620
gaaaaggtct aggaagagtc cgcaccctct ccccgcggtg gccacgccgg gctccgcgct 10680
gagccctctg tgttcttgtc tctccatacc tcatcacggc accgcagggt tgcagccact 10740
cctggtctca ttttacacac caggaaattg aggctctttg agaagccgtg gtgatgattt 10800
catcagcatg ctctggggca gacccctgca gccgcacagg gtgcctgggg cccacactag 10860
tgccctggtt tatagacaga cagaggtggc agtggcgctt ccgagtcggg ctgcgatgtg 10920
cttgcactcc ccgaggggct gaggggccct gcgcccaggt gcagctgctt gggtgctgcc 10980
agcccctccc acctctccct ccctgccagc ccctcccacc tctccctccc tgccagcccc 11040
tcccacctct ccctccctgc cagcccctcc cacctctccc tccctgccag cccctcccac 11100
ctctccctcc ctgccagccc ctcccacctc tccctccctg ccagcccctc ccacctctcc 11160
ctccctgcca gcccctccca cctctccctc cctccagccc ctcccacctc tccctccctg 11220
ccagcccctc ccacctctcc ctccctgcca gcccctccca cctctccctc cctgccagcc 11280
cctcccacct ctccctccct gccagcccct cccacctctc cctccctgcc agcccctccc 11340
acctctccct ccctgccagc ccctcccacc tctccctccc tggctcatcc ctgctgtgtc 11400
ccttctctct agtttcctgt tcagtttcag gaaggaggct gggaacccag atgtagggaa 11460
tttgcgccct ggagtcagac ctgggttcac gtcccagcgc ctccacctct ggtgtgacct 11520
tggtccagtc tctcagcctc agtttcctca cctgtaaagt gggctccatg attagatgca 11580
ccctgcaggg cagtgtagca gtgacctggc tcagccactg gcagccccaa caatcatacc 11640
ttgttaaagt agctctgtcg gttccctcag gggttccggg ggcccattcc cctgtcctcc 11700
atgcactgtg agacctgccc tgccacagag cagagtgtaa cagcctgagg gtgagagcca 11760
gacactgtgc ctgtgcttag accagacact ggacgacggg agccagtgca gcctgggcgg 11820
gtggactcct atggacccct cagcacccag cctcggtgcc ttcagcgcag ggccgcgtgg 11880
ctgtgggggc tcacaagacc cggcccactc ctgcttgtgc ctacatctgg gtgtttgccc 11940
attggtgcct tttgacgcgt tctggtgtgt gtgagacgtg cggggctggg aagtgttggc 12000
agagccgcga gtaccgtcct cactcctttt gttcttttga cgtaagctgg cgagtggcac 12060
tgcctgagtt ccgctcagtg cccgccctga tgtgcggacc ccgctgcatt cttgctgtta 12120
ggtggtggcg gtgtgcgctg tcgctggtgg gcaccgagag tctttgggag ctttggggag 12180
gttgtgccaa gcctgagcct cgacgtcccc cttcccggct ttctgttggc tcttctgagg 12240
ccagggcatc tctatgaggg cctcctgctg gagccgtctc tgtggatctc ctctgccatc 12300
ctggcccatg agtgggtgat gcgctggcca ccatctggtg acagtggccg ggcaccgctg 12360
ccaaatgtgg gtcccgcatc tgcaagcccc tccctgggtc ccctagggta tggggtggtt 12420
ctgccactgc cctcgctccc ccaccttggg gtgcctctcc ccctgctcgt gggggagacc 12480
ctgcctggga tctgctttcc agcaaggaat atactttgga gggagacaca catgttcttt 12540
tctggagctc tgcagtggcc acggcagccc agcccgccaa gcaccctgga atgaaaacat 12600
cccgctgctg tctgggcctg gcctgcactc tgctgcctgc gctccagctg gctgaggccg 12660
ggcacgtctg cgggcacagc agcgggggcg ccacagtctc cctgcagagt gagcgcagct 12720
ggaaaatgca gctcacgccc tttcccagaa cacctcgctc ttcatggctt ggcagctgtc 12780

-continued cttgcctagg ggccagggtg cccaggcact ggtggcagga gaagggctac atctggggct 12840
gaggcgggct gggtcctttt ctccctgcag ctcccgaggc ccagccctgg cccagcctgg 12900
cattcctgac cttagcagcg ccatgatctg aagacaggct ggcttctgtg aggccacctc 12960
agaaagggct ttgtgcccag gcagaggcgg aagccagctc ttccttctgg ttgaggcagg 13020
aatgaggcca gcgctgggca agcccatgcc cagggaacgt cacagctgtg ggagtacagg 13080
ggctccgggt tctgagcccg tccactgtgc atcgtggccc tggcctcagg atggctcgta 13140
ccatcattgg ctgtgcccac agccgagtgg gtgatgggat tccggctgcc ccgctggatc 13200
tgtgctgctg ccctctccag ggcactgctg tgcccgcaca gccgggcgca gatggccagt 13260
ttgcttgccc cccccccac catcctcttc ctaccttggc ttcctccatt gacacactgg 13320
accctgctgg ctgcccgggg aggtgtttgg gggatggtgt tgggggagga ggagggcccc 13380
ttgagcctca gtgtgcccat caggagcgta aggtcagtgc agcacctgcc cacacaggct 13440
gtgaagggtg ggagtggaga gggatgcaag ggggtcacaa cgcctggctc catgtcagct 13500
gcgtgcaggg gcaccaggag ccggccctca ttctcccctt gaactggaag ggtggccccg 13560
accccagcgg caggtagcat acgtatgaag cgctctcctt cctacacccc acaggtgggc 13620
tcgtctccag acggcccttt ttgagctggc tgtgtttttc catctgtgta ggcaaggaca 13680
tcgcagactc ccctttctca tctccctcgt tcagcctccg aggccggagt ctccatccct 13740
gtgcctgcct gtgggtcccg ggaggacctg aggctgccca tgtcaccccc ggcatctcat 13800
cctggggaca gttcagccgt gggagggatc tgtaaggaca gaatgccgct gagcctgggg 13860
ctccccagct agtctcacac cccgtgtctg ggacccagag accctcgtgc agggctctgt 13920
tgcttggggc ctggcagcct cgtcctgtat cagaggctgc cacccccacc cctcgtgggg 13980
ccagggttgt ggccggcctc cctggccctc cccatggaag tggtaggcgg agccagcagc 14040
catctgccca gcccggggct gcactgtttt ttttcaaatg agcaccgtcc caaactgcag 14100
cccgttaatt taaacaggat catttccggc cctggaagcc gcctcactct ccttaaatag 14160
aaaggagcac agcgcagagg gaaacagatg aggtcatggc tcggctggcc cagcgaggaa 14220
ggggccgcag tgggggtggc actgccgcct gtcccctgtc ctctccagcg cccacactgc 14280
agcccatttc ctcaccctgg gcctgctctc gggagggacg ggcctggggg tcctcttgct 14340
gggcggaggg gaaccagctc ctccaggaga ggacggggcc tggcaggggg catggggcct 14400
ccctgggtct ggcgtcctgt cctgcccctg ccgagggagg agcggttaca taagctccgc 14460
aggcggcccc tccgagccgg tccccccagc ccagtttcca gtgaggcggc cagcgcgggc 14520
gggggtgccg ggcctggcgc acacccgctg ctgaccacac gtgtctggaa tgtgcagatg 14580
tttctttggg ggctccgtcc ggcccccaga ccccactcag catctggtct ggggagtggg 14640
cgcctggggc actcagctct gagtgtgaga ctctgaggca ggtctggttt gtctggggcc 14700
attccctctg ctgtggattg ggagggcccc gggagctgcc ccacacccag ggaagttctc 14760
ctcagtccca ctgttgcatt ccccgacccc ggctcccccg gcccaggagc gcctgtgggg 14820
cagaaggccc agccccaaga cttcccggcc ctgccagcct caggcttcac ccaccctcgc 14880
gccaactgtg ggcagagccc agggggaggg caggagagcc agcgcctggc tgggaacacc 14940
cctgaggggc cgaggctcca gggcgagggg gcccgacctg ggttcacac gcccgggtgg 15000 cgggcagacc cgctgcagca tgagacacgt gtcagctacc tcgggccggc aggctggccc 15060
tgctgcccac agccctggga cgtggcccca cctgtgacgg gtgtggaggg gcagcctcca 15120
ggcctggcca caccctctgc tgttgctgct cctgctccag gattggcaag ggtgctggga 15180

```
aggggtgaag acccgtactg tggccacaca cctgggactt ccttctccac ccagtggtgc  15240
cccagcagcc gctaaggagc ccgctgggtc ccacgctagg atggtcctaa ctcctcccgc  15300
cttccagatc ggacgctcgg cgctggggac cccttgtgtc ccggggctgg ggcaccgtcc  15360
tgcccccatg gggtgtact cctcccgaca agcttggctt cagcttccct gggagcacat  15420
cctggccctc gggcacccat caggctgtcc ctgtgcacct ggctcccacc cttccagctc  15480
atagcaggaa ctggggtgag gagtgcgtgg ggcagcaagg gcctgggacc ccagaggacc  15540
ctgcactctg ctctgtgctc ttgcctgggc ttagggccgc tcggtggtcc tgctgccaga  15600
tgcctgggcc ctgctgtgtc ccccatcctt gcagggaacc agaacgtggg ggcagggcat  15660
cagacagcgg cgatgatgtc acctggcggg tgcagaggaa gcccgagggg cggggtgggg  15720
gggctggcgc gaggctgcct ggctaggcct tggcgttccc ccagaacggc gatggcaaaa  15780
gcagatggag acgtgaaaaa gtacgggagc aagcgaggtg aggactccac ggggacccct  15840
gtgctgttcc ctgtccctga agcccacacc tgagtcctgc ccagggcaga tgcttccaca  15900
cccagggggc acctgagtcc tacccagggc agacgcttcc acaccctggg ggctgggga  15960
ctgcacctgg ctcctgtctg ggccccagct tcattccact gccctgggcc ctgggagctc  16020
ggccgagcgg ggtccccaag accttgctgc atttctgggc cttgggctgg ggtgagggcc  16080
gggagaagga gccagcctgg agcctggcac gcagggagtg catggccaga accggtgaca  16140
ggcagggctg cctgctggcg tggaagaagt gtccatggca cccccaggcc tggttcacag  16200
tgggatgggc ggggagccgg ggggctctgg ggtcctcggc tgacctgccc ccacccctgc  16260
cctggcttgt cagctcccag cagcagccac tcttgatgga ttttccagaa aatgaggtgt  16320
ggccaaacat cttcaggctt ttccttcttt cctttctccc gtggcctggg tgggagctgc  16380
tccccatgcc tgggggcagg tgcgagagcc tgtgcccctc cctggggcag tttcacagct  16440
gtgtcccttc cagggggcct gcctgtgttc accgtggcct ctgcagcacc tctcgcccct  16500
tagggctcct gcgcctcggg tcccggtgcc tcatttctcc ctaaagcatt ggttctgctg  16560
ccgccgcagc cgctggaaag tccctcctca ggtctaactg cagttcctca cggcacagtg  16620
ttccccctcg ggcatggtgc ttgggcagtg ggtgtgagtc cagctgcctc accctgtctc  16680
gagaatggcc tcttgctggt ctcccagcca ccaccctgtc ccaccccacg gcggggatgg  16740
tgtggatgcc tagcagcgcg gctgtgggcc cacccatcct tatgggcagt ggggagcacc  16800
tcagcccgtg tccctacctt ggtgtagagg aggggacggc agagaagcag ggttcagtta  16860
ggggggaagt ggtggccctg ccggaggggc cgttccctgt gtgcctggcc cccagatcct  16920
ctcccctccc ggagcccagg gcacaggcat aggctctctg agtgtcccac agcccctggg  16980
ggaagggaac tgcaccccca accgtgccct ccatccgcag atggaacgag aagctccggg  17040
agccagtgcc cagcgtctca tctgtctggg cacccagccc aggtgagggc ctggctccac  17100
cgtccgtggc tggtgctgct tcctggcacg gagaaggcct cggctgctct gtcccctcag  17160
ctggggtggc ctctggtccc cttctttgtt ggttcccttc tcaagctctt gccctggccc  17220
cgggccccac cgggcagcct gtgtgtgcgt ctctcctgcg ccgggtaggc tcctgtggga  17280
gcggagctcc ggtgggagga gcagggctgg aggctggcag gggctgggcg ggtgttcagg  17340
gatggaggcc gccccggctt ggggctggct gccgggtggt cattgctggg aagagcaagt  17400
ctaggcggag gcacctgctg ggtcactcgt ggggagggtg acacctgggg aagtagaggc  17460
ccgtggcagg aggtgaggcc tcggggtcct ggggagcagg ggggtggtgt gcagacctgc  17520
```

-continued

```
ggagccatag tcctgtgcca ggagcactac tgggagtgcg tgggaccagg aggggtgccc  17580
agggtgggcg gcagagtgac ccccgaggtg cttgaggccg aggggaggtg gagttctcgg  17640
tttgccccag ctctctgtct actcacctcc gcatcaccag ctccaggacc tggtttgtaa  17700
ctcgggcagc tctgaaaaga gagacatgct gccgccctgt ggtttctgtt gctttttctt  17760
cactgactac tgacatggga tgtttttcct acggctgtga ccaattgtgc ttcttctaat  17820
tgcctggttt ttctttttt gtttttggag ttttctcttt ctttcctccc tccctctcac  17880
cctccatcct ttttttttt atttttattt tttgagatgg agcttcactc ttgcaggatg  17940
gggtgctgga gtgcaggggt gcgatctcag ctcactgcaa cctctgcctc gcgggttcaa  18000
gtgattctcc tgcctaagcc tcctgagtag ctggaattac aggtgcttgc caccacgccc  18060
gactaattct gtagttttgg tagagacagg gtgtctccgt gttggtcggt ctggtcttga  18120
actcctgacc tcaggtgatg cgcccgcctc agcctcccaa agtgctggga ttacaggcag  18180
gagccattgc acccggctct ttccccttct cctttcttc tctctctcct ccctttcttt  18240
cttttctttt cttttttttt tcttttgaga tggagtctcg ctctgtcacc aggctggatt  18300
gcagtggcgt gatcttggct cactgcaacc ttcgcctccc gggttcacgt gattctcctg  18360
cctcagcctc ctgagtggct ggcactacag gctcccgccg ccatgcccgg ctaattttg  18420
catttttagt agagacaggg tttcaccctg ttggccagga tggtctcgat ctcttgatct  18480
catgatccac ccaccttggc ctcccaaagt tctggcatta caggagtgag ccaccgtgcc  18540
cggccatctt tctttccttg ctttctcttt gttttcttc gagaccgggt cttgctctgt  18600
cgcccaggct ggactgcagt ggcacaatca tagctcactg cagcctcgac ttccctggct  18660
caagcgatcc ttcctcctca gcccccgag tagctggaac tacagttaca cactaccatg  18720
cctggctgat tctttttttc cttgtagaga tggggtcttg ctatgctgtc catcctggtc  18780
tcaaactcct ggccttccca aagcactggg tttacaggca taagccacca cacccagttt  18840
ccttttcttc tttttaactg gaatagttga cgttttcttt attagctgtg tgtcaggagg  18900
gtatttttgg cctttagtat gtcgtgtaag ttgctagtgc ttttctgaga ttgtagtttg  18960
ttttctaatt ttatttatat tttgcgtaga agttgtgtat tttagatgga gttaggtcgg  19020
ctggtctttg atgttttatt tattaattat gtatgtattt atttattttt gaggtagagt  19080
ctcgccgttt cacccaggct ggagtacagt gatgcgatct cagctccctg tagccttgac  19140
ctctctgggc tcaagtgatt tttctctcct ctacctcccg agtacttggg accccaggcg  19200
catgccgcca tgcctggcta atgtgtattt tttgtagata cggggtctca ctgtgttgcc  19260
cagggtggtt tcaaaatcct gggcccaggc gatccttccg tctcagctcc cacggtgctg  19320
tgttaccggc gtgtgcccag tgcctggccg tcttggaggt cttgtttctc tgggtttatg  19380
cctcgaggtg gcgcctgctc ccctgtgctc cctggtagcc tggtagtgag cctgcttctc  19440
acacagtcat acctggttgt ggtcccacag tgggaccacc ctgttgggtt cagaacagga  19500
gatgggggcc cctcgagtct gtgtgggggc tgtggacagg gttgggagac cttggctctg  19560
tgggggactg tggacagggg atggggggcc ttggccctgc gtgggatggg ttgggggtcc  19620
gtgcccttcc tggccctggg tggacaggtc catgtggcac tcggcatagg gctgagatgg  19680
gtgcagaggg ctgaggcccc caggcctctc ctggcttggt ttccccagat gagtgttcat  19740
ttgggtcttc catcagaaag tcccctcctg acctctggga gtggggagct caagggtggg  19800
aggccatagc ttggggatgc tggcaatgtg tgggatgggc ccagggaagg cctctggcct  19860
actaggggct ctggccctga cccacggcca ctcactcctc agagacgtct cccacaacct  19920
```

gctccgggcg ctggacgttg ggctcctggc gaacctctcg gcgctggcag agctgtgagt 19980
gtcccccagt cgtgccagca tgcggggctc actccgggtg ggctggcggc accgcctctt 20040
gctgctcagc tgtgggggct tccatcagct ttgccgaatc cccgtctctt tccagggata 20100
taagcaacaa caagatttct acgttagaag aaggaatatt tgctaattta tttaatttaa 20160
gtgaaatgta agttgtggtt ctttgggtgg ggtcctggct ggaccccagg cccccaatat 20220
cccttctgcc ctcccagttg gtccgtgtcc ccttccaggc ttgagaccag atcctggggg 20280
cagttcactg cctgcttgga gccccccagt gccggcttgg ttggggcagg ggaggcggtg 20340
ctgtcagggt ggctccaggg cctggttgcc agtggggggc tggcatagac ccttcccacc 20400
agacctggtc cccaacacct gcccctgccc tgcagaaacc tgagtgggaa cccgtttgag 20460
tgtgactgtg gcctggcgtg gctgccgcga tgggcggagg agcagcaggt gcgggtggtg 20520
cagcccgagg cagccacgtg tgctgggcct ggctccctgg ctggccagcc tctgcttggc 20580
atccccttgc tggacagtgg ctgtggtgag tgccggtggg tggggccagc tctgtccttc 20640
ccagccaggt gggacctggg ccctgcagac actgggcagg gctcaggaag gcctctctgg 20700
ggggggcctc cgggccaagg gaacagcatg ggagcctgtg agtgcggcgg gcggatgtgg 20760
gggcgtgggg tggagccagg aggagcagaa cccggggtcc agtggctgcc tcttctaggt 20820
gaggagtatg tcgcctgcct ccctgacaac agctcaggca ccgtggcagc agtgtccttt 20880
tcagctgccc acgaaggcct gcttcagcca gaggcctgca gcgccttctg cttctccacc 20940
ggccagggcc tcgcagccct ctcggagcag ggctggtgcc tgtgtggggc ggcccagccc 21000
tccagtgcct cctttgcctg cctgtccctc tgctccggcc ccccgccacc tcctgccccc 21060
acctgtaggg gccccaccct cctccagcac gtcttccctg cctccccagg ggccaccctg 21120
gtggggcccc acggacctct ggcctctggc cagctagcag ccttccacat cgctgccccg 21180
ctccctgtca ctgccacacg ctgggacttc ggagacggct ccgccgaggt ggatgccgct 21240
gggccggctg cctcgcatcg ctatgtgctg cctgggcgct atcacgtgac ggccgtgctg 21300
gccctggggg ccggctcagc cctgctgggg acagacgtgc aggtggaagc ggcacctgcc 21360
gccctggagc tcgtgtgccc gtcctcggtg cagagtgacg agagcctcga cctcagcatc 21420
cagaaccgcg gtggttcagg cctggaggcc gcctacagca tcgtggccct gggcgaggag 21480
ccggcccgag gtgagtgtct gctgcccact ccccttcctc cccagggcca tccagatggg 21540
gcagagcctg gtacccccgt cttgggccca cactgaccgt tgacaccctc gttcccaccg 21600
gtctccagcg gtgcacccgc tctgcccctc ggacacggag atcttccctg gcaacgggca 21660
ctgctaccgc ctggtggtgg agaaggcggc ctggctgcag gcgcaggagc agtgtcaggc 21720
ctgggccggg gccgccctgg caatggtgga cagtcccgcc gtgcagcgct tcctggtctc 21780
ccgggtcacc aggtgcctgc cccaccccc cgaggggcca taggttggga gatctctgaa 21840
gcactggggc agagactgcg gctggggagt ctcaggagga aggaggtggg agctgggccg 21900
gccctggtga gcaggtggcg ccggccggtg gggccgttcc tgtcagctct gcagatgcag 21960
aggtggacat gagctggggg cagcctccgg acactcctgg gcacgccata cgggaggtgg 22020
cctgcacggg gatccctgcc ggtacccaca ggccccgtgg gtgggtgctg ctgtgagcct 22080
gggctggtgg gccctggtct ccgggctctg agcctcagtt tccccatctg gaaaggggga 22140
cagtgatggg gctcccagcg ggctgctgtg agggtgggag gatggaggag tgccctgagc 22200
cccctgccat cccacacccg cccccaggag cctagacgtg tggatcggct tctcgactgt 22260

```
gcagggggtg gaggtgggcc cagcgccgca gggcgaggcc ttcagcctgg agagctgcca  22320
gaactggctg cccggggagc cacacccagc cacagccgag cactgcgtcc ggctcgggcc  22380
caccgggtgg tgtaacaccg acctgtgctc agcgccgcac agctacgtct gcgagctgca  22440
gcccggaggt gtgcgggggg ccaggcaggg gcctgagacg ctggctgtgg ttaggggcct  22500
gccgagcgcc cgcggtggag cctgggctga ggaggagggg ctggtggggg ggttttcggg  22560
cggctcggtc cccagtctgt tcgtcctggt gtcctgggcc ctggcccggc gcctcactgt  22620
gcactcgcca ccccaggccc agtgcaggat gccgagaacc tcctcgtggg agcgcccagt  22680
ggggacctgc agggacccct gacgcctctg gcacagcagg acggcctctc agccccgcac  22740
gagcccgtgg aggtagtcgg ccccccacgt tctacaacct gccctcctgc ctgcccctgg  22800
aggccttgcc tgccctgccc actgtgggtc tcgccaaaaa acttgggggc cttaatgttg  22860
cttgtgccca gtgaagatgg ttgggaaaat ccagagtgca gagaggaaag cgtttactca  22920
cattacctcc aggccttttc tctgagcgtg tgtgagttat tcctgaaagg caggtcaggg  22980
gtcctgcccc ccatggacag tttccaccgg agtcttcctc tcgagcgaca ggagccaggc  23040
ctgtgggggt ctgatggctc gctctccttc cctcccctct tcctgggaag ttcgggtagg  23100
gggagtctgg gcttcaggct gggatggggt ctgtggagct gaggcggccc cctgcccacc  23160
aggtcatggt attcccgggc ctgcgtctga gccgtgaagc cttcctcacc acggccgaat  23220
ttgggaccca ggagctccgg cggcccgccc agctgcggct gcaggtgtac cggctcctca  23280
gcacagcagg tgggactctg ggtggtgggt ggtgggtggt gggcgccgca ggactcgggg  23340
tggcctctct gagctttcac gtctgctggt cctgtggcca ccagagtggt tcccagtctt  23400
aggtggacag agcaggggtt ccagagacac cagctcattc caggtgtcct gggggtggat  23460
tgggtggggc ctgcctgggg gccggcctgg gtcagtcggc tggccggaga cggacgcagc  23520
actgggctgg gagtgctgcc caggtgggga gacctgtcct cacagcaagg ccaggattgc  23580
tggtgcaggc agttgggcat ctctgacggt ggcctgtggg caaatcaggg ccccaacacc  23640
ctcccctcct cacagggacc ccggagaacg gcagcgagcc tgagagcagg tccccggaca  23700
acaggaccca gctggccccc gcgtgcatgc caggggggacg ctggtgccct ggagccaaca  23760
tctgcttgcc gctggacgcc tcctgccacc cccaggcctg cgccaatggc tgcacgtcag  23820
ggccagggct acccggggcc ccctatgcgc tatggagaga gttcctcttc tccgttcccg  23880
cggggccccc cgcgcagtac tcggtgtgtg gccctgacct gggtctgttc cctgcatctc  23940
ctcaggccac cttcctgtct gctgcccagg gtctgggtct gtgcaccaga cacacccagc  24000
ctgcaggccc ctcccacgtc cttgccacct ctgacctccg acctctgcag tgccctcggc  24060
cctctcccag tgggagaagc tctcgcctgg gcccttggca cgagctgtgc ctcctcttcc  24120
tctctcccag cacagctgct ccttcctgtc tgccaggtct tggcctgtgt cctctccccg  24180
tgtgtccccc ggtctgcaac tgtcctgcct gtccttgtca cgagcactgt ggggaggctc  24240
cttgaggtgt ggctgacgaa gcggggagcc ctgcgtgtcc accctcatcc gtcgtgcggg  24300
ggtccacggg ccatgaccgt gaggacgtga tgcagccctg cctccctctc cacaggtcac  24360
cctccacggc caggatgtcc tcatgctccc tggtgacctc gttggcttgc agcacgacgc  24420
tggccctggc gccctcctgc actgctcgcc ggctcccggc caccctggtc cccgggcccc  24480
gtacctctcc gccaacgcct cgtcatggct gccccacttg ccagcccagc tggagggcac  24540
ttgggcctgc cctgcctgtg ccctgcggct gcttgcagcc acggaacagc tcaccgtgct  24600
gctgggcttg aggcccaacc ctggactgcg gctgcctggg cgctatgagg tccgggcaga  24660
```

ggtgggcaat ggcgtgtcca ggcacaacct ctcctgcagc tttgacgtgg tctccccagt 24720
ggctgggctg cgggtcatct accctgcccc ccgcgacggc cgcctctacg tgcccaccaa 24780
cggctcagcc ttggtgctcc aggtggactc tggtgccaac gccacggcca cggctcgctg 24840
gcctgggggc agtgtcagcg cccgctttga gaatgtctgc cctgccctgg tggccacctt 24900
cgtgcccggc tgcccctggg agaccaacga taccctgttc tcagtggtag cactgccgtg 24960
gctcagtgag gggggagcacg tggtggacgt ggtggtggaa aacagcgcca gccgggccaa 25020
cctcagcctg cgggtgacgg cggaggagcc catctgtggc ctccgcgcca cgcccagccc 25080
cgaggcccgt gtactgcagg gagtcctagt ggtgagtatg gccgaggctc caccaccagc 25140
ccccaggcag gtgcctgcag acagggtgct cacacagggc gtgaggcctg gcttcccagt 25200
gagggcagca gcccagttac tggggacgtc ggccccgggc aggtcctgct ggctggctcc 25260
tcgggctacc tggtgggctt taaattcctg gaaagtcacg gctctgacag tggctccgct 25320
aactcattcc actgtctcat ttcacaaaat gaatttaaaa ctctgctccc tgacctcaca 25380
cgagcccccg tgagtctctc acgccctctg ctgtgttctc gcctggctaa agcgagtggc 25440
ttttgaggtg gagtctgaac ccctgatggg aaactgcggg ctgcccgcgg tgccaccatg 25500
ctgggtacat gggggacagg gctgtctcca tcttgcgggt acctgcctct tcaccagggg 25560
ccttgggagg ggccatcaga aatggcgtga cctgtgcagc ctgtcctggg ttctgtaagc 25620
cagtgtaggt gcctcccctc actgctccga gctctctggg tgaggagctg gggcaagagc 25680
gccgggaggg tctgagaaga ctcagagaga ggtggactct ttgtagctgg tactaggttt 25740
gctttacaga tggggaaact gaggcacaga gaggttgagg cattagtagt actacatggc 25800
tggctggaga gccggacagt gagtgtccca gcccgggctt ggctcccatg gcatgcagag 25860
ccccgggcac ctcctctcct ctgtgccccg cgtgggactc tccagcccga cgggaggtgt 25920
gtccaggagg cgacaggcta agggcagagt cctccacaga gcccaggctg acaccattcc 25980
ccccgcagag gtacagcccc gtggtggagg ccggctcgga catggtcttc cggtggacca 26040
tcaacgacaa gcagtccctg accttccaga acgtggtctt caatgtcatt tatcagagcg 26100
cggcggtctt caagctctca gtaggtgggc gggggtgggg aggggagggg atggggcggg 26160
gcagggcggg ggcgggctcc accttcacct ctgccttctg ctctgcttca tgctgcccga 26220
ggacgctgcc atggctgtgg gtgagtggag ggagggacgc caatcagggc caggcctctc 26280
acctgccacc tgggctcact gacgcctgtc cctgcagctg acggcctcca accacgtgag 26340
caacgtcacc gtgaactaca acgtaaccgt ggagcggatg aacaggatgc agggtctgca 26400
ggtctccaca gtgccggccg tgctgtcccc caatgccacg ctagcactga cggcgggcgt 26460
gctggtggac tcggccgtgg aggtggcctt cctgtgagtg actcgggggc cggtttgggg 26520
tgggcaccag gctcttgtcc cagccccagc ctcagccgag ggacccccac atcacggggt 26580
tgcttttctg agcctcggtt tccctgtctg ttgggaggta actgggtgca caggagccct 26640
gaggctgcac gggagccggg agaggcctca gcacagccgg gtgggccctg aatggaggcc 26700
cggggcgtga ctgcagagtg gagcctcggc tgggtcccaa gcaccccctg ccccgccacc 26760
gcccacccct gtcccggttc actcactgcg tcccaccgcc ccggcaggtg gacctttggg 26820
gatggggagc aggccctcca ccagttccag cctccgtaca acgagtcctt cccggttcca 26880
gacccctcgg tggcccaggt gctggtggag cacaatgtca tgcacaccta cgctgcccca 26940
ggtgagggat gagggggtga gggggccact gcctttcagg ctctgagcac gggtccccccc 27000

-continued agctccccag tcaagctgcc ccccttcctc cccaacagcc ctcactgtga cctcacctgg 27060
gctgatggct taggccctac tggggtgagg gaggggccag gcgtgggggg agtggacagg 27120
gaagctgggc ccctgaactg cgcccccccgc cctccccggg cctggctctt gctgctctgc 27180
tgccccgagt gcagctgcac ttggaggcgg tgcgtcctcg ccaggcagcc ctcagtgctg 27240
ctacacctgt gctccgtccc gcacgtggct tgggagcctg ggacccttaa ggctgggccg 27300
caggtgcagc cgttcacccc gggctcctca ggcgggggggc ttctgccgag cgggtgggga 27360
gcaggtgggg gtgccgcggc tgccccactc gggcctgtcc ccacaggtga gtacctcctg 27420
accgtgctgg catctaatgc cttcgagaac cggacgcagc aggtgcctgt gagcgtgcgc 27480
gcctccctgc cctccgtggc tgtgggtgtg agtgacggcg tcctggtggc cggccggccc 27540
gtcaccttct acccgcaccc gctgccctcg cctgggggtg ttctttacac gtgggacttc 27600
ggggacggct cccctgtcct gacccagagc cagccggctg ccaaccacac ctatgcctcg 27660
aggggcacct accacgtgcg cctggaggtc aacaacacgg tgagcggtgc ggcggcccag 27720
gcggatgtgc gcgtctttga ggagctccgc ggactcagcg tggacatgag cctggccgtg 27780
gagcagggcg cccccgtggt ggtcagcgcc gcggtgcaga cgggcgacaa catcacgtgg 27840
accttcgaca tgggggacgg caccgtgctg tcgggcccgg aggcaacagt ggagcatgtg 27900
tacctgcggg cacagaactg cacagtgacc gtgggtgcgg ccagccccgc cggccacctg 27960
gcccggagcc tgcacgtgct ggtcttcgtc ctggaggtgc tgcgcgttga acccgccgcc 28020
tgcatcccca cgcagcctga cgcgcggctc acggcctacg tcaccgggaa cccggcccac 28080
tacctcttcg actggacctt cggggatggc tcctccaaca cgaccgtgcg ggggtgcccg 28140
acggtgacac acaacttcac gcggagcggc acgttccccc tggcgctggt gctgtccagc 28200
cgcgtgaaca gggcgcatta cttcaccagc atctgcgtgg agccagaggt gggcaacgtc 28260
accctgcagc cagagaggca gtttgtgcag ctcggggacg aggcctggct ggtggcatgt 28320
gcctggcccc cgttccccta ccgctacacc tgggactttg gcaccgagga agccgccccc 28380
acccgtgcca ggggccctga ggtgacgttc atctaccgag acccaggctc ctatcttgtg 28440
acagtcaccg cgtccaacaa catctctgct gccaatgact cagccctggt ggaggtgcag 28500
gagcccgtgc tggtcaccag catcaaggtc aatggctccc ttgggctgga gctgcagcag 28560
ccgtacctgt tctctgctgt gggccgtggg cgccccgcca gctacctgtg ggatctgggg 28620
gacggtgggt ggctcgaggg tccggaggtc acccacgctt acaacagcac aggtgacttc 28680
accgttaggt ggccggctgg aatgaggtga gccgcagcga ggcctggctc aatgtgacgg 28740
tgaagcggcg cgtgcggggg ctcgtcgtca atgcaagccc cacggtggtg cccctgaatg 28800
ggagcgtgag cttcagcacg tcgctggagg ccggcagtga tgtgcgctat tcctgggtgc 28860
tctgtgaccg ctgcacgccc atccctgggg gtcctaccat ctcttacacc ttccgctccg 28920
tgggcacctt caatatcatc gtcacggctg agaacgaggt gggctccgcc caggacagca 28980
tcttcgtcta tgtcctgcag ctcatagagg ggctgcaggt ggtgggcggt ggccgctact 29040
tccccaccaa ccacacggta cagctgcagg ccgtggttag ggatggcacc aacgtctcct 29100
acagctggac tgcctggagg gacaggggcc cggccctggc cggcagcggc aaaggcttct 29160
cgctcaccgt ctcgaggccg gcacctacca tgtgcagctg cgggccacca acatgctggg 29220
cagcgcctgg gccgactgca ccatggactt cgtggagcct gtggggtggc tgatggtggc 29280
cgcctccccg aacccagctg ccgtcaacaa aagcgtcacc ctcagtgccg agctggctgg 29340
tggcagtggt gtcgtataca cttggtcctt ggaggagggg ctgagctggg agacctccga 29400

-continued gccatttacc acccatagct tccccacacc cggcctgcac ttggtcacca tgacggcagg 29460
gaacccgctg ggctcagcca acgccaccgt ggaagtggat gtgcaggtgc ctgtgagtgg 29520
cctcagcatc agggccagcg agcccggagg cagcttcgtg gcggccgggt cctctgtgcc 29580
cttttggggg cagctggcca cgggcaccaa tgtgagctgg tgctgggctg tgcccggcgg 29640
cagcagcaag cgtggccctc atgtcaccat ggtcttcccg gatgctggca ccttctccat 29700
ccggctcaat gcctccaacg cagtcagctg ggtctcagcc acgtacaacc tcacggcgga 29760
ggagcccatc gtgggcctgg tgctgtgggc cagcagcaag gtggtggcgc ccgggcagct 29820
ggtccatttt cagatcctgc tggctgccgg ctcagctgtc accttccgcc tgcaggtcgg 29880
cggggccaac cccgaggtgc tccccgggcc ccgtttctcc cacagcttcc cccgcgtcgg 29940
agaccacgtg gtgagcgtgc ggggcaaaaa ccacgtgagc tgggcccagg cgcaggtgcg 30000
catcgtggtg ctggaggccg tgagtgggct gcaggtgccc aactgctgcg agcctggcat 30060
cgccacgggc actgagagga acttcacagc ccgcgtgcag cgcggctctc gggtcgccta 30120
cgcctggtac ttctcgctgc agaaggtcca gggcgactcg ctggtcatcc tgtcgggccg 30180
cgacgtcacc tacacgcccg tggccgcggg gctgttggag atccaggtgc gcgccttcaa 30240
cgccctgggc agtgagaacc gcacgctggt gctggaggtt caggacgccg tccagtatgt 30300
ggccctgcag agcggcccct gcttcaccaa ccgctcggcg cagtttgagg ccgccaccag 30360
ccccagcccc cggcgtgtgg cctaccactg ggactttggg gatgggtcgc cagggcagga 30420
cacagatgag cccagggccg agcactccta cctgaggcct ggggactacc gcgtgcaggt 30480
gaacgcctcc aacctggtga gcttcttcgt ggcgcaggcc acggtgaccg tccaggtgct 30540
ggcctgccgg gagccggagg tggacgtggt cctgcccctg caggtgctga tgcggcgatc 30600
acagcgcaac tacttggagg cccacgttga cctgcgcgac tgcgtcacct accagactga 30660
gtaccgctgg gaggtgtatc gcaccgccag ctgccagcgg ccggggcgcc cagcgcgtgt 30720
ggccctgccc ggcgtggacg tgagccggcc tcggctggtg ctgccgcggc tggcgctgcc 30780
tgtggggcac tactgctttg tgtttgtcgt gtcatttggg gacacgccac tgacacagag 30840
catccaggcc aatgtgacgg tggcccccga gcgcctggtg cccatcattg agggtggctc 30900
ataccgcgtg tggtcagaca cacgggacct ggtgctggat gggagcgagt cctacgaccc 30960
caacctggag gacggcgacc agacgccgct cagtttccac tgggcctgtg tggcttcgac 31020
acaggtcagt gcgtggcagg gccgtcctcc atgcccctca cccgtccaca cccatgagcc 31080
cagagaacac ccagcttgcc accagggctg gcccgtcctc agtgcctggt gggccccgtc 31140
ccagcatggg gagggggtct cccgcgctgt ctcctgggcc gggctctgct ttaaaactgg 31200
atggggctct caggccacgt cgccccttgt tctcggcctg cagagggagg ctggcgggtg 31260
tgcgctgaac tttgggcccc gcgggagcag cacggtcacc attccacggg agcggctggc 31320
ggctggcgtg gagtacacct tcagcctgac cgtgtggaag gccggccgca aggaggaggc 31380
caccaaccag acggtgggtg ccgcccgccc ctcggccact tgccttggac agcccagcct 31440
ccctggtcat ctactgtttt ccgtgtttta gtgctggtgg aggccgcacg ctctcccctc 31500
tctgtttctg atgcaaattc tatgtaacac gacagcctgc ttcagctttg cttccttcca 31560
aacctgccac agttccacgt acagtcttca agccacatat gctctagtgg caaaagctac 31620
acagtcccct agcaatacca acagtgagga agagcccctt cccaccccag aggtagccac 31680
tgtccccagc ccatgtccct gttgctggat gtggtgggcc ggttctcacc ctcacgctcc 31740

-continued

```
cctctctgga ccggccagga ggcttggtga ccctgagccc gtggtggctg ctcctgctgc  31800
tgtcaggcgg ggcctgctgg tgccccagag tgggcgtctg ttccccagtc cctgctttcc  31860
tcagctggcc tgattggggg tcttcccaga ggggtcgtct gaggggaggg tgtgggagca  31920
ggttccatcc cagctcagcc tcctgaccca ggccctggct aagggctgca ggagtctgtg  31980
agtcaggcct acgtggcagc tgcggtcctc acacccacac atacgtctct tctcacacgc  32040
atccccccag gggccctcag tgagcattgc ctgcctcctg ctagggtcca gctgggtcca  32100
gtacaccaga acgcacactc cagtgtcctc tgccctgtgt atgcccttcc gccgtccaag  32160
ttggaaggtg gcaaaccgga tgagtatcct gggagggagt gagctcaccg gcagtggcca  32220
ggcccctggg aaacctggag tttgggagca gcatcctcca tgggtccccc agtccttcca  32280
gcaggccaaa tagacctgtg ttggaggtaa ccccactccc acgccaggtg ctgatccgga  32340
gtggccgggt gcccattgtg tccttggagt gtgtgtcctg caaggcacag gccgtgtacg  32400
aagtgagccg cagctcctac gtgtacttgg agggccgctg cctcaattgc agcagcggct  32460
ccaagcgagg ggtgagtgtt gagcggggtg tgggcgggct ggggatgggt cccatggccg  32520
aggggacggg gcctgcaggc agaagtgggg ctgacagggc agagggttgc gccccctcac  32580
cacccccttct gcctgcagcg gtgggctgca cgtacgttca gcaacaagac gctggtgctg  32640
gatgagacca ccacatccac gggcagtgca ggcatgcgac tggtgctgcg gcggggcgtg  32700
ctgcgggacg gcgagggata caccttcacg ctcacggtgc tgggccgctc tggcgaggag  32760
gagggctgcg cctccatccg cctgtccccc aaccgcccgc cgctgggggg ctcttgccgc  32820
ctcttcccac tgggcgctgt gcacgccctc accaccaagg tgcacttcga atgcacgggt  32880
gagtgcaggc ctgcgtgggg ggagcagcgg gatcccccga ctctgtgacg tcacggagcc  32940
ctcccgtgat gccgtgggga ccgtccctca ggctggcatg acgcggagga tgctggcgcc  33000
ccgctggtgt acgccctgct gctgcggcgc tgtcgccagg gccactgcga ggagttctgt  33060
gtctacaagg gcagcctctc cagctacgga gccgtgctgc cccgggttt caggccacac  33120
ttcgaggtgg gcctggccgt ggtggtgcag gaccagctgg gagccgctgt ggtcgccctc  33180
aacaggtgag ccaggccgtg ggagggcgcc cccgagactg ccacctgctc accaccccct  33240
ctgctcgtag gtctttggcc atcaccctcc cagagcccaa cggcagcgca acggggctca  33300
cagtctggct gcacgggctc accgctagtg tgctcccagg gctgctgcgg caggccgatc  33360
cccagcacgt catcgagtac tcgttggccc tggtcaccgt gctgaacgag gtgagtgcag  33420
cctgggaggg gacgtcacat ctgctgcatg cgtgcttggg accaagacct gtacccctgc  33480
ctggagcttt gcagagggct catcccgggc cccagagata aatcccagtg accctgaagc  33540
agcaccccga ccttccgctc ccagcagcca cacccaccgg gccctctccg gcgtctgctt  33600
tccacaatgc agcccccgcc caggagggcc catgtgctta ccctgttttg cccatgaaga  33660
aacagctcag tgttgtgggt cagtgcccgc atcacacagc gtctagcacg taactgcacc  33720
ccgggagtcg tgggcatctg ctggcctcct gccggcctcc tgcgctgctg acagcttgct  33780
gtgcccctg cctgccccag tacgagcggg ccctggacgt ggcgcagagc ccaagcacga  33840
gcggcagcac cgagcccaga tacgcaagaa catcacggag actctggtgt ccctgagggt  33900
ccacactgtg gatgacatcc agcagatcgc tgctgcgctg gcccagtgca tggtaggatg  33960
gccccacctg ctcaccctgc cccgcatgcc tgccagggca ctgggttcag ccccccaggg  34020
cagacgggca gcttggccga ggagctgagc ctccagcctg ggctccttcc tgccatggcg  34080
ttcctcggtc tctgacctgc ttcagtagcc tcagccgttc tgtcctgtgt gaacgcaggg  34140
```

```
tgcctctcgg gggacccagg gtgtaaagag gggcccagat gtggggaggg actaagaaga  34200
tgctgctctg tgccctccac tctcccctcc cctcccctcc cccttccctc ccctagcccc  34260
tcccctcctc ccctcccta gcccttcccc tcctcccctc ccctagccct ttcccttctt  34320
cccccccagc ccttcccctc ctcccctccc ctagcccttc ccctcctccc ctcccctacc  34380
ccttcccctc ctcccctccc ctagaccttc ccctcacctc ctcccgctga gcccctccac  34440
tcgtccccca gcccctccct cccctagccc ctcccctccc ccttcctccc ctcctccccc  34500
tcccctcctc cccctccctc ttcctccccc tcccctcctc cccttcctc ccctctcctc  34560
cccctcccct cctgtccccc ctcctcccct cctccctcct cccctcctcc cccctcctcc  34620
tccccctcct ccctcctccc tcctccccct cctcctcctc ccctcctccc tcctcccctc  34680
ctcccctccc ctcctccccc tccccctcc cttcctcccc ctccccctc ccctcctccc  34740
cctctcctcc tcccatccct cctcccatcc ctcctccccg ttcccattct ctcccctccc  34800
ccttccattt ctccctcctc cccctgccct cctctcctcc tcacctcccc ttctccgctc  34860
ctttcttctc ctccctccct ttctctcctc cctcccttc tcccttctc ctcttctccc  34920
cttctcctct cttttcatcc ttcccttctt ccctcctttc ctcctctttt ccctcttctc  34980
ccccctcctc ccctccttcc tcctcccatt ccccctcctc ccccctccca ttccccctcc  35040
tcccctcctt cctcctccca ttacccctcc tctcctcccc tcctcccacc cccctctcct  35100
cccggctcct ctcctcccct cctcatcccc ctcctctcct tccctcctaa ccccccctcct  35160
ctcctcccct cctcatcccc ctcctctcct tccctcctcc tatccccct cctctcctcc  35220
cctcctccta ttccccctcc tctcctcccc tccttcctcc tcctctcctc ccatgccccc  35280
tcctcccctc ctcccatccc cctcctcccc tcctccctcc tcccatccca tcccccctcct  35340
ctcctcccct tctctcccct cctctcctcc cctcctctcc tctcctcctc tcctcccctc  35400
ctcccatccc ccctcctccc atcccccctc ctctcctccc cactcctctc ctccccactc  35460
ctctcctccc ctcatccccc tcctctctcc tcccctcccc ctcctctcct tccctcctcc  35520
tttcctcccc tcccccctcct tcccccctcct ccccctcctt ctccccatcc cccttcccct  35580
tctcctcctc tcccctcccc cttctctttt tccctcctcc tcccttcctc ctcccctctt  35640
ctcccctttt ccctttctc ttcctctcct cccctctcc cctcctgtcc tccctccctt  35700
tctctctttc tttcctccct ttccttctcc cctgttctcc tcccttccct tctcccctttt  35760
tcttccctcc tcctttcctc ccctcctcct tttctctgtt tctcttcctt tcccctccac  35820
tttcccctc ctttcccctc tcctttctcc ttcctttcct ctccccttct cttccttttc  35880
ctctctcccc ttcttttccc tcttcccctc ccctcctctt cccctcccct cctcttcccc  35940
tcccctcctc ttcccctccc ctcctcttcc cctctcctcc tcttcccctc ccctcctctt  36000
tccctcccct cttctcctcc cctcctctcc cctcttcccc tcccctcctc ttccctcccc  36060
ttcccctccc ctcctcttcc ctccccttcc cctcccctcc tcttccctcc ccttcccctc  36120
ctcttccttc ctctcttccc ctcccctcct cttccctccc ctcttcccct cccctctctct  36180
tctcctcccc ttctcttccc ctccccttttt cttccctctc cttgtcttcc ctgccctcct  36240
cttccctccc ctcctcttcc ctcccctctt cccctctcct cctcttccct cccctcttcc  36300
tctttcctct tcccctcccc tcctcctccc tcccctttcc cctcttcccc tcccctccgc  36360
ttccctcccc tttctccccc ttctctcccc tcccctctcc ccccttctct cccctcccct  36420
ctccccttc tctcccctcc cctctccccc ttctctcccc tctcctctcc cccttctctc  36480
```

-continued

```
cccctctct ccccccttctc tctcccctc tctcccccctt ctctcccctc ccccccttctc 36540
tcccctcccc tctcccccctt ctctcccctc ccctctcccc tgtcctctcc tctccaccct 36600
tctctcccct cccctctcct ctccccccttc cctctcctct ccccccttctc tcccctcccc 36660
tctcctctcc ccccttttct ccactcccct ctcctctctc ccctcctcct ccgctctcat 36720
gtgaagaggt gccttgtgtg gtcggtgggc tgcatcacgt ggtccccagg tggaggccct 36780
gggtcatgca gagccacaga aaatgcttag tgaggaggct gtgggggtcc agtcaagtgg 36840
gctctccagc tgcagggctg gggtgggag ccaggtgagg acccgtgtag agaggagggc 36900
gtgtgcaagg agtggggcca ggagcggggc tggacactgc tggctccaca caggggccca 36960
gcagggagct cgtatgccgc tcgtgcctga agcagacgct gcacaagctg gaggccatga 37020
tgctcatcct gcaggcagag accaccgcgg gcaccgtgac gcccaccgcc atcggagaca 37080
gcatcctcaa catcacaggt gccgcggccc gtgccccatg ccacccgccc gccccgtgcg 37140
gccctttcct ctgcctccct cctcccccca accgcgtcgc ctttgcccca tcccatcttc 37200
gtcccctcc cctcccccca attcccatcc tcatcccct cccccaattc ccattctcct 37260
ccccctcccc cttccctatt accatccctt ttctccatct ctctcccctt ttctccattt 37320
cccccccgt cctccccgtc cttttgtcca ttcccctcat cttcctcatc cccctcatcc 37380
cccttcccct cccttatccc ccttcccctc cctttccccc tgctcctctt cttctccctt 37440
ctcttttctc taccctttc cttcctttt cctccctctc cccatcatcc ccctcatctt 37500
cgtcctcatc cccatcacct tccccctccc ccctccacca ctctctctcc agcttccccc 37560
ttccttctgc ctgcacctcg ctctctgccc cctcaggttc cccctttctc ccagccccca 37620
ccctccggct cccccttttt gcctgccccc accctccctc tacctccctg tctctgcact 37680
gacctcacgc atgtctgcag gagacctcat ccacctggcc agctcggacg tgcgggcacc 37740
acagccctca gagctgggag ccgagtcacc atctcggatg gtggcgtccc aggcctacaa 37800
cctgacctct gccctcatgc gcatcctcat gcgctcccgc gtgctcaacg aggagcccct 37860
gacgctggcg ggcgaggaga tcgtggccca gggcaagcgc tcggacccgc ggagcctgct 37920
gtgctatggc ggcgccccag ggcctggctg ccacttctcc atccccgagg ctttcagcgg 37980
ggccctggcc aacctcagtg acgtggtgca gctcatcttt ctggtggact ccaatccctt 38040
tccctttggc tatatcagca actacaccgt ctccaccaag gtggcctcga tggcattcca 38100
gacacaggcc ggcgcccaga tccccatcga gcggctggcc tcagagcgcg ccatcaccgt 38160
gaaggtgccc aacaactcgg actgggctgc ccggggccac cgcagctccg ccaactccgc 38220
caactccgtt gtggtccagc cccaggcctc cgtcggtgct gtggtcaccc tggacagcag 38280
caaccctgcg gccgggctgc atctgcagct caactatacg ctgctggacg gtgcgtgcag 38340
cgggtggggc acacgcggcc ccctggcctt gttcttgggg ggaaggcgtt tctcgtaggg 38400
cttccatggg tgtctctggt gaaatttgct ttctgtttca tgggctgctg ggggcctggc 38460
cagagaggag ctgggggcca cggagaagca ggtgccagct ctggtgcaga ggctcctatg 38520
ctttcaggcc cgtggcagag ggtgggctca ggagggccat cgtgggtgtc ccccgggtgg 38580
ttgagcttcc cggcaggcgt gtgacctgcg cgttctgccc caggccacta cctgtctgag 38640
gaacctgagc cctacctggc agtctaccta cactcggagc cccggcccaa tgagcacaac 38700
tgctcggcta gcaggaggat ccgcccagag tcactccagg gtgctgacca ccggccctac 38760
accttcttca tttccccggg gtgagctctg cgggccagcc tggcagggca gggcagggca 38820
tcatgggtca gcattgcctg ggttactggc cccatgggga cggcaggcag cgaggggact 38880
```

ggaccgggta tgggctctga gactgcgaca tccaacctgg cggagcctgg gctcacgtcc 38940
gctacccctt ccctgcccag gagcagagac ccagcgggga gttaccatct gaacctctcc 39000
agccacttcc gctggtcggc gctgcaggtg tccgtgggcc tgtacacgtc cctgtgccag 39060
tacttcagcg aggaggacat ggtgtggcgg acagaggggc tgctgcccct ggaggagacc 39120
tcgccccgcc aggccgtctg cctcacccgc cacctcaccg ccttcggcgc cagcctcttc 39180
gtgcccccaa gccatgtccg ctttgtgttt cctgtgagtg accctgtgct cctgggagcc 39240
tctgcagagt cgaggagggc ctgggtgggc tcggctctat cctgagaagg cacagcttgc 39300
acgtgacctc ctgggcccgg cggctgtgtc ctcacaggag ccgacagcgg atgtaaacta 39360
catcgtcatg ctgacatgtg ctgtgtgcct ggtgacctac atggtcatgg ccgccatcct 39420
gcacaagctg gaccagttgg atgccagccg gggccgcgcc atccctttct gtgggcagcg 39480
gggccgcttc aagtacgaga tcctcgtcaa gacaggctgg ggccggggct caggtgaggg 39540
gcgcagcggg gtggcagggc ctcccctgct ctcactggct gtgctggttg caccctctgg 39600
gagtgagtct cgtcgcaggc gtcagaacaa ggcagttttt gcagtgctgt gtgaagggct 39660
cgtgtgttca tcctgggaat gacctcgtga gcactcactg tccctgagga ctaggacagc 39720
tcctagctgg aagtaggtgc cagtcagtca gggtgggcag cccacgttct gcacagtagc 39780
gtggccccac aagtgacgtg agcatcgcta ccactgtggg agactgtgca tccacccgcg 39840
atcctgactg catagctcgt ctctcagacg gaggcgccag caccctcccc gtggctgttt 39900
cttcagtacc tccattttcc tttcattgga attgcccttc tggcattccc tttttgtttt 39960
cgtttttctt tttttagaga cggagtctca ctctgttgcc caggctggag tgcaatggca 40020
tgatcttggc tcacagcaac ttccagctcc cgggtttaag ccattcccct taagcgattc 40080
tcctgagtag ctgggagtac aggtgcacac caccacaccc agttaatttt tcaccatgtc 40140
agccaggcga actcctgacc tcaggtgatc cgcctgcctc ggcctgccag agtgctggga 40200
tgacaggtgt gagccaccac acctggctgt gttcccattt tttatctctg tgctgctttc 40260
ctcttcattg cccagttctt tcttttgatt acctactttt aaaaactgtc ggccgggcgc 40320
ggtggctcac acctgtaatc cgagcacttt gggaggccag gcaggcaaat cacggggtca 40380
ggagatcgag accatcctgg ctaacggtga aaccctgtct ctaataaaaa gtacaaaaaa 40440
attagcccgg cgtagtggca ggcgcctgta gtcccagctc cttgggagac tgaggcagga 40500
gaatggcgtg aacccgggag gcggagcttg cagtgagctg agattgcgcc actgcactcc 40560
agcctgggtg acacagcaag actccatctc aaaaaaaaaa gaaaaaaaat actgtcacct 40620
gggtctgtca ctgggagagg aggtgacaca gcttcacgct ttgcagtctg tgcatgaact 40680
gagggacggg tgtgtggtgc gggtcaccgg ttgtggcatg actgaggcgt ggacaggtgt 40740
gcagtgcggg tcactggttg tggtgtggac tgaggcgtgt gcagccatgt ttgcatgtca 40800
caagttacag ttctttccat gtaacttaat catgtccttg aggtcctgct gttaattgga 40860
caaattgcag taaccgcagc tccttgtgta tggcagagcc gtgcaaagcc gggactgcct 40920
gtgtggctcc ttgagtgcgc acaggccaaa gctgagatga cttgcctggg atgccacacg 40980
tgttgggcag cagaccgagc ctcccacccc tccctcttgc ctcccaggta ccacggccca 41040
cgtgggcatc atgctgtatg gggtggacag ccggagcggc caccggcacc tggacggcga 41100
cagagccttc caccgcaaca gcctggacat cttccggatc gccaccccgc acagcctggg 41160
tagcgtgtgg aagatccgag tgtggcacga caacaaaggt ttgtgcggac cctgccaagc 41220

-continued

```
tctgcccctc tgccccccgca ttggggcgcc ctgcgagcct gacctccctc ctgcgcctct  41280
gcagggctca gccctgcctg gttcctgcag cacgtcatcg tcagggacct gcagacggca  41340
cgcagcgcct tcttcctggt caatgactgg ctttcggtgg agacggaggc caacgggggc  41400
ctggtggaga aggaggtgct ggccgcgagt aaggcctcgt tccatggtcc cactccgtgg  41460
gaggttgggc agggtggtcc tgccccgtgg cctcctgcag tgcggccctc cctgccttct  41520
aggcgacgca gcccttttgc gcttccggcg cctgctggtg gctgagctgc agcgtggctt  41580
ctttgacaag cacatctggc tctccatatg ggaccggccg cctcgtagcc gtttcactcg  41640
catccagagg gccacctgct gcgttctcct catctgcctc ttcctgggcg ccaacgccgt  41700
gtggtacggg gctgttggcg actctgccta caggtgggtg ccgtaggggt cggggcagcc  41760
tcttcctgcc cagcccttcc tgcccctcag cctcacctgt gtggcctcct ctcctccaca  41820
cagcacgggg catgtgtcca ggctgagccc gctgagcgtc gacacagtcg ctgttggcct  41880
ggtgtccagc gtggttgtct atcccgtcta cctggccatc ctttttctct tccggatgtc  41940
ccggagcaag gtgggctggg gctggggacc cgggagtact gggaatggag cctgggcctc  42000
ggcaccatgc ctagggccgc cactttccag tgctgcagcc agagggaaag gcgtccacca  42060
aaggctgctc gggaagggtc aacacacttg agcagcctta gctagactga ccagggagaa  42120
agagagaaga ctcagaagcc agaatggtga aagaacgagg gcactttgct aagcagacgc  42180
cacggacgac tgcacagcag cacgccagat aactcagaag aagcaagcac gcggctgtgc  42240
acgcttccga aatgcactcc agaagaaaat ctcagtacat ctataggaag tgaagaggct  42300
gagttagtcc cttagaaacg tcccagtggc cgggccgggt gtggtggctc acgcctgtaa  42360
tcccaacact tcaggtggcc gaggtgggcg gatctgagtc caggagtttg agaccagcct  42420
gggcaacata gcaagacccc atctatataa aacattaaaa agggccaggc gcggtggctc  42480
acgcctgtaa tcccagcact ttgggaggcc gaggcgggca gatcacttga ggtcaggagt  42540
tcgagaccag cctggccaac acaatgaaac cccgactcta ctacaaatac aaaaacttag  42600
ctgggcatgg tggcgggcgc ctgtagtccc agctactcga gaggctgagg caggagaatg  42660
gcatgaaccc aggaggcgga gcttgcagtg agccgagatt gcgccactgc actccatcct  42720
gggcaacgga gcaagactcc atctccaaaa aaaaaaaaaa aaaatcccac aaagaaaagc  42780
tcaggctcag agccttcacg atagaatttt tctaagcagt taaggaagaa ttaacaccaa  42840
tccttcacag actctttcca agaatacagc aggtgggaac gcttcccatt catacggaaa  42900
cgggaggccg caccccttag gaatgcacac gtggggtcct caagaggtta catgcaaact  42960
aaccccagca gcacacagag aaggcgcata agccgcgacc aggaggggtt gctcccgagt  43020
ccgtggcagg aaccagaggc cacatgtggc tgctcgtatt taagttaatt aaaatggaac  43080
gatggccggg tgtggtggct cacacctgta atcccagcac tttgggaggc ggaggcgggc  43140
agatcacttg aggtcaggag ttccaagacc agcctggcca acacagtgaa accccgtctc  43200
tactaaaaat acaaaaaatt agctgggcat ggtggcaggc acctgtaatc ccagctactc  43260
aggaggctga gccaggacaa tcgcctgaac gcgggaggtg gaggttgcag tgagctgaga  43320
ttgcgccatt gcactccagc ctgggtgaca gcgagactcc atctaaaaaa gaaaatatga  43380
aatttaaaac tctgttcctt agctgcacca gtctgctgtc aagtgttcag tggcacacgt  43440
cgcgaggggc tgccatcacg gacggtgcag atgtcccata tatccagcat tctaggacat  43500
tctgtcagat ggcaccgggc tctgtcctgt ctgctgagga ggtggcttct catccctgtc  43560
ctgagcaggt ctgagctgcc gcccgctgac cactgccctc gtcctgcagg tggctgggag  43620
```

cccgagcccc acacctgccg ggcagcaggt gctggacatc gacagctgcc tggactcgtc 43680
cgtgctggac agctccttcc tcacgttctc aggcctccac gctgaggtga ggactctact 43740
gggggtcctg ggctgggctg ggggtcctgc cgccttggcg cagcttggac tcaagacact 43800
gtgcacctct cagcaggcct ttgttggaca gatgaagagt gacttgtttc tggatgattc 43860
taagaggtgg gttccctaga gaaacctcga gccctggtgc aggtcactgt gtctggggtg 43920
ccgggggtgt gcgggctgcg tgtccttgct gggtgtctgt ggctccatgt ggtcacacca 43980
cccgggagca ggtttgctcg gaagcccagg gtgtccgtgc gtgactggac gggggtgggc 44040
tgtgtgtgtg acacatcccc tggtaccttg ctgacccgcg ccacctgcag tctggtgtgc 44100
tggccctccg gcgagggaac gctcagttgg ccggacctgc tcagtgaccc gtccattgtg 44160
ggtagcaatc tgcggcagct ggcacggggc caggcgggcc atgggctggg cccagaggag 44220
gacggcttct ccctggccag cccctactcg cctgccaaat ccttctcagc atcaggtgag 44280
ctggggtgag aggaggggc tctgaagctc acccttgcag ctgggcccac cctatgcctc 44340
ctgtacctct agatgaagac ctgatccagc aggtccttgc cgagggggtc agcagcccag 44400
cccctaccca agacacccac atggaaacgg acctgctcag cagcctgtga gtgtccggct 44460
ctcgggggag gggggattgc cagaggaggg gccgggactc aggccaggca gccgtggttc 44520
ccgcctgggg tagggtgggg tggggtgcca gggcagggct gtggctgcac cacttcactt 44580
ctctgaacct ctgttgtctg tggaaagagc ctcatgggat ccccagggcc ccagaacctt 44640
ccctctaggg agggagcagg ctcatggggc tttgtaggag cagaaaggct cctgtgtgag 44700
gctggccggg gccacgtttt tatcttggtc tcagagcagt gagaaattat gggcgggttt 44760
ttaaataccc catttttggc cgggcgcggt ggctcacacg tgtaatccca gcactttggg 44820
aggccgaggt gggcagatga cctgaggtca gcagttcgag accagcctgg ccaacatggc 44880
gaaaccccgt ctctactaaa aatacaaaaa attagccggg catgctggca ggcgcctgta 44940
gtcccagtta ctcgggagac tgaggtagga gaatcgattg aacctggtag gtgaaggttg 45000
tagtgagccg agatcgcgcc actgcactcc agcctgggca acaagagcga aactccgtct 45060
caaaaacaaa aaaattcctc aatttcttgg ttgttttgta acttatcaac aaatggtcat 45120
atagaggtta ccttgtatgt agtcacgcac atagtcacgc acatggcagc cggcggcgga 45180
gcgcacccac ggcgtgttcc cacgcgtgtg accccgggct ctgccatgcc ctcctatgct 45240
caggtgtgct gaggtccaca cggccctgcc gttgcactgc agctgcctgc aggattcagt 45300
gcagtggcat gcagtgcagg tgcggtgccc cggagccaca ggccacacca cagggcctgc 45360
atgcacaggg gctgcggtgt ctgggtttgg gtaactacgc cctgtgacat ttgcacagca 45420
acagaattac ctaatgacgc atttctcaga acacatccct ggcactaagt ggtgcgtgac 45480
tgctgctttt gcatccacat ctagtttgat ttgtgtgtta ttcctttgag tgcttctcat 45540
tgttaagcaa ccaagaacta aagaggtatg aactgcccct ggactcaaac aaaaaggaaa 45600
acttcctgat ttacaaaagg cagataacca tcacatgagg gcatctttat gaataaattg 45660
ctggttggtt ttaaaaatac agagtatggg gaaatccagg ggtagtcact acatgctgac 45720
cagccccagg tatctccggc ccaaagctct gtgaaatcca gattcagtgc ttccgcgggg 45780
atttctgacg gcagctcaga ctccgcatcc acacagagcg cgtggccctc accctcccgg 45840
cttcctcaac ccttggccgt cccttgctcg gacagtgctt cgggctgacc aggtcggagg 45900
cttgggtttg tcctggaccc ctctgcgtcc ttcctcactg cagcctccag cgcgtcccgt 45960

-continued

```
ggctcctttc ccaacgcaga gcacggcctt ccctgcgcct gagcctgcac cctccgtcct  46020
ggcggcgcct ctgccctggc attccctgcc actccatgcc tccctattgg ccattctccg  46080
tctctgccag cgagagcctg ctccctgagt cagaccctga gtcatttgtg ttgctataaa  46140
ggaatagttg aggctgggtt attttttatt tttatttatt tttttgagat ggagtctctg  46200
ttgcccagac tggagtgcag tcgcatgatc tcggctcact gcaaagtctg cctcccacgt  46260
tcaagcagtt atctgcctca gcctcccaag tagctaagat tacaggcgcc cgccgccaca  46320
gccggctaat tttttgtgtg tgtgttttag tagagaggag gtttcaccat cttagccagg  46380
ctggtcttga actcctgacc tcgtgatcca cccatctcag cctcccaaaa tgctgagatt  46440
acaggcgtga gccaccacgc ctgaccaagt tgaggctagg tcattttttta attttttgta  46500
aagacagggt ctcactgtct ccaactcctg agctcaagtg atcctcctgc ctcagcctcc  46560
tgaagtgctg ggattacagg cttgagacac tgcgcccagc caagagtgtc ttttatcctc  46620
cgagagacag caaaacagga agcattcagt gcagtgtgac cctgggtcag gccgttcttt  46680
cggtgatggg ctgacgaggg cgcaggtacg ggagagcgtc ctgagagccc gggactcggc  46740
gtctcgcagt tggtctcgtc ctccccctca acgtgtcttc gctgcctctg tacctcttct  46800
ctagcagctc tgggaccggg catatcagca tggtggcccg atgcagtggc acagcctcgg  46860
tggtcactgg ctcctggaga cacaagcaga tctctggcct cagggagccc tacacactgt  46920
tgggatttga aaggcattca tatgtttcct tgtccagaag ttaattttag gccataaacc  46980
tgcatgggac agacacactg gcgtctctag attgtagaga tgcttgttgg atggttgaga  47040
cccaatcata gtttgcaggg ttgaaggggg gctcattgca ccctgagaga ctgtgcactg  47100
ctgtaagggc agctggtcag gctgtgggcg atgggtttat cagcagcaag cgggcgggag  47160
agggacgcag gcggacgcct gacttcggtg cctggagtgg ctcttggttc cctggctccc  47220
agcaccactc ccactctcgt ttggggtagg gtcttccggc tttttgtcgg ggggaccctg  47280
tgacccaaga ggctcaagaa actgcccgcc caggttaaca tgggcttggc tgcaactgcc  47340
tcctggaggc cgggatgaat tcacagccta ccatgtccct caggtccagc actcctgggg  47400
agaagacaga gacgctggcg ctgcagaggc tgggggagct ggggccaccc agcccaggcc  47460
tgaactggga acagccccag gcagcgaggc tgtccaggac aggtgtgctt gcgtagcccc  47520
gggatgcccc tagcccctcc ctgtgagctg cctctcacag gtctgtctct gcttccccag  47580
gactggtgga gggtctgcgg aagcgcctgc tgccggcctg gtgtgcctcc ctggcccacg  47640
ggctcagcct gctcctggtg gctgtggctg tggctgtctc agggtgggtg ggtgcgagct  47700
tccccccggg cgtgagtgtt gcgtggctcc tgtccagcag cgccagcttc ctggcctcat  47760
tcctcggctg ggagccactg aaggtgaggg ggctgccagg ggtaggctac aggcctccat  47820
cacgggggac ccctctgaag ccaccccctc cccaggtctt gctggaagcc ctgtacttct  47880
cactggtggc caagcggctg cacccggatg aagatgacac cctggtagag agcccggctg  47940
tgacgcctgt gagcgcacgt gtgccccgcg tacggccacc ccacggcttt gcactcttcc  48000
tggccaagga agaagcccgc aaggtcaaga ggctacatgg catgctgcgg gtgagcctgg  48060
gtgcggcctg tgcccctgcc acctccgtct cttgtctccc acctcccacc catgcacgca  48120
ggacactcct gtccccccttt cctcacctca gaaggccctt aggggttcaa tgctctgcag  48180
cctttgcccg gtctccctcc taccccacgc cccccacttg ctgccccagt ccctgccagg  48240
gcccagctcc aatgcccact cctgcctggc cctgaaggcc cctaagcacc actgcagtgg  48300
cctgtgtgtc tgcccccagg tggggttccg ggcagggtgt gtgctgccat taccctggcc  48360
```

```
aggtagagtc ttggggcgcc ccctgccagc tcaccttcct gcagccacac ctgccgcagc  48420
catggctcca gccgttgcca aagccctgct gtcactgtgg gctggggcca ggctgaccac  48480
agggcccccc cgtccaccag agcctcctgg tgtacatgct ttttctgctg gtgaccctgc  48540
tggccagcta tggggatgcc tcatgccatg ggcacgccta ccgtctgcaa agcgccatca  48600
agcaggagct gcacagccgg gccttcctgg ccatcacgcg gtacgggcat ccggtgcact  48660
ggtctgtctt ctgggcttta gttttgcctt tagtccagcc agaccctagg ggacatgtgg  48720
acatgtgtag ataccttttgt ggctgctaga actggaggta ggtgctgctg gcatcagtag  48780
gcagagggga gggacacagg tccgtgtctt gcagtgcaca ggacgggccc atgacagaca  48840
actgtctgcc ccagaacatc cccaggataa ggctgagaag cccaggtcta gccgtggcca  48900
gcagggcagt gggagccatg ttccctgggt ctctggtggc cgctcactcg aggcgggcat  48960
ggggcagtag gggctggagc gtgtgactga tgctgtggca ggtctgagga gctctggcca  49020
tggatggccc acgtgctgct gccctacgtc cacgggaacc agtccagccc agagctgggg  49080
cccccacggc tgcggcaggt gcggctgcag gaaggtgagc tggcagggcg tgccccaaga  49140
cttaaatcgt tcctcttgtt gagagagcag cctttagcgg agctctggca tcagccctgc  49200
tccctagctg tgtgaccttt gccctcttaa caccgccgtt tccttctctg tatatgagag  49260
atggtaacgt tgtctaattg atggctgctg ggagggttcc ctggggtggc gccgaaccag  49320
agctcaggcg agctggccag caggaaacac tcctgttggg ttttgatgag gccctggccc  49380
cggcctgggg ctctgtgtgt ttcagcactc tacccagacc ctcccggccc cagggtccac  49440
acgtgctcgg ccgcaggagg cttcagcacc agcgattacg acgttggctg ggagagtcct  49500
cacaatggct cggggacgtg ggcctattca gcgccggatc tgctggggtg agcagagcga  49560
gggccccggg cgtctacgcc aaggacaagg gagtagttct ccaggagtgc cgcggcctcc  49620
tgaccagcct ggctccgggg tgccggaagg gctggggtgc ggcacccacg ccacccctct  49680
ccggcagggc atggtcctgg ggctcctgtg ccgtgtatga cagcgggggc tacgtgcagg  49740
agctgggcct gagcctggag gagagccgcg accggctgcg cttcctgcag ctgcacaact  49800
ggctggacaa caggtgggag ctccctcccc tgccctctcc ggggtggccg cagtcaccag  49860
ccaggagccc accctcactc ctccggcccc cgctggccta ggcggcttcc acagcccctc  49920
agccacgcct gcactgcgcg gtccccgcag ctcccgccct gccacccgct cctactgacc  49980
cgcaccctct gcgcaggagc cgcgctgtgt tcctggagct cacgcgctac agcccggccg  50040
tggggctgca cgccgccgtc acgctgcgcc tcgagttccc ggcggccggc cgcgccctgg  50100
ccgccctcag cgtccgcccc tttgcgctgc gccgcctcag cgcgggcctc tcgctgcctc  50160
tgctcacctc ggtacgcccg tccccggcca gaccccgcgc ctcccaccgg cagcgtcccg  50220
ccccctcgcg gggccccgcc cggcagcgtc tcacccctcg cagcgccccg ccccctcgca  50280
gcgtcccgcc ccctcgcagg gccccgcccc ggcagcgtcc cgccccctcg tagggccccg  50340
ccccggcagc gtcccgcccc ctcgcagggc cccgccccgg cagcgtccct cccgccctcc  50400
tgaccgcgcc ccccacaggt gtgcctgctg ctgttcgccg tgcacttcgc cgtggccgag  50460
gcccgtactt ggcacaggga agggcgctgg cgcgtgctgc ggctcggagc ctgggcgcgg  50520
tggctgctgg tggcgctgac ggcggccacg gcactggtac gcctcgccca gctgggtgcc  50580
gctgaccgcc agtggacccg tttcgtgcgc ggccgcccgc gccgcttcac tagcttcgac  50640
caggtggcgc agctgagctc cgcagcccgt ggcctggcgg cctcgctgct cttcctgctt  50700
```

-continued

```
ttggtcaagg tgagggctgg gccggtgggc gcggggctgg gcgcacaccc cagggctgca  50760
agcagacaga tttctcgtcc gcaggctgcc cagcagctac gcttcgtgcg ccagtggtcc  50820
gtctttggca agacattatg ccgagctctg ccagagctcc tgggggtcac cttgggcctg  50880
gtggtgctcg gggtagccta cgcccagctg gccatcctgg taggtgactg cgcggccggg  50940
gagggcgtct tagctcagct cagctcagct gtacgccctc actggtgtcg ccttccccgc  51000
agctcgtgtc ttcctgtgtg gactccctct ggagcgtggc ccaggccctg ttggtgctgt  51060
gccctgggac tgggctctct accctgtgtc ctgccgagtc ctggcacctg tcacccctgc  51120
tgtgtgtggg gctctgggca ctgcggctgt ggggcgccct acggctgggg gctgttattc  51180
tccgctggcg ctaccacgcc ttgcgtggag agctgtaccg gccggcctgg gagccccagg  51240
actacgagat ggtggagttg ttcctgcgca ggctgcgcct ctggatgggc ctcagcaagg  51300
tcaaggaggt gggtacggcc cagtgggggg gagagggaca cgccctgggc tctgcccagg  51360
gtgcagccgg actgactgag cccctgtgcc gcccccagtt ccgccacaaa gtccgctttg  51420
aagggatgga gccgctgccc tctcgctcct ccaggggctc caaggtatcc ccggatgtgc  51480
ccccacccag cgctggctcc gatgcctcgc acccctccac ctcctccagc cagctggatg  51540
ggctgagcgt gagcctgggc cggctgggga caaggtgtga gcctgagccc tcccgcctcc  51600
aagccgtgtt cgaggccctg ctcacccagt ttgaccgact caaccaggcc acagaggacg  51660
tctaccagct ggagcagcag ctgcacagcc tgcaaggccg caggagcagc cgggcgcccg  51720
ccggatcttc ccgtggccca tccccgggcc tgcggccagc actgcccagc cgccttgccc  51780
gggccagtcg gggtgtggac ctggccactg gccccagcag gacacccctt cgggccaaga  51840
acaaggtcca ccccagcagc acttagtcct ccttcctggc gggggtgggc cgtggagtcg  51900
gagtggacac cgctcagtat tactttctgc cgctgtcaag gccgagggcc aggcagaatg  51960
gctgcacgta ggttccccag agagcaggca ggggcatctg tctgtctgtg ggcttcagca  52020
ctttaaagag gctgtgtggc caaccaggac ccagggtccc ctccccagct cccttgggaa  52080
ggacacagca gtattggacg gtttctagcc tctgagatgc taatttattt ccccgagtcc  52140
tcaggtacag cgggctgtgc ccggccccac cccctgggca gatgtccccc actgctaagg  52200
ctgctggctt cagggagggt tagcctgcac cgccgccacc ctgcccctaa gttattacct  52260
ctccagttcc taccgtactc cctgcaccgt ctcactgtgt gtctcgtgtc agtaatttat  52320
atggtgttaa aatgtgtata tttttgtatg tcactatttt cactagggct gaggggcctg  52380
cgcccagagc tggcctcccc caacacctgc tgcgcttggt aggtgtggtg gcgttatggc  52440
agcccggctg ctgcttggat gcgagcttgg ccttgggccg gtgctggggg cacagctgtc  52500
tgccaggcac tctcatcacc ccagaggcct tgtcatcctc ccttgcccca ggccaggtag  52560
caagagagca gcgcccaggc ctgctggcat caggtctggg caagtagcag gactaggcat  52620
gtcagaggac cccagggtgg ttagaggaaa agactcctcc tgggggctgg ctcccagggt  52680
ggaggaaggt gactgtgtgt gtgtgtgtgt gcgcgcgcgc acgcgcgagt gtgctgtatg  52740
gcccaggcag cctcaaggcc ctcggagctg gctgtgcctg cttctgtgta ccacttctgt  52800
gggcatggcc gcttctagag cctcgacacc cccccaaccc ccgcaccaag cagacaaagt  52860
caataaaaga gctgtctgac tgcaatctgt gcctctatgt ctgtgcactg gggtcaggac  52920
tttatttatt tcactgacag gcaataccgt ccaaggccag tgcaggaggg agggccccgg  52980
cctcacacaa actcggtgaa gtcctccacc gaggagatga ggcgcttccg ctggcccacc  53040
tcatagccag gtgtgggctc ggctggagtc tgtgcagggg ctttgctatg ggacggaggg  53100
```

```
tgcaccagag gtaggctggg gttggagtag gcggcttcct cgcagatctg aaggcagagg  53160

cggcttgggc agtaagtctg ggaggcgtgg caaccgctct gcccacacac ccgccccaca  53220

gcttgggcag ccagcacacc ccgctgaggg agccccatat tccctacccg ctggcggagc  53280

gcttgatgtg gcggagcggg caatccactt ggaggggtag atatcggtgg ggttggagcg  53340

gctatgatgc acctgtgagg ccatctgggg acgtaggcag ggggtgagct cactatcagg  53400

tggcacctgg gcctgtccca ccagctcacg cctggaccca cccccactca catttgcgtg  53460

cagggccatc tggcgggcca cgaagggcag gttgcggtca gacacgatct tggccacgct  53520

gg                                                                 53522
```

<210> SEQ ID NO 2
<211> LENGTH: 4303
<212> TYPE: PRT
<213> ORGANISM: Homo sapiens

<400> SEQUENCE: 2

```
Met Pro Pro Ala Ala Pro Ala Arg Leu Ala Leu Ala Leu Gly Leu Gly
1               5                   10                  15

Leu Trp Leu Gly Ala Leu Ala Gly Gly Pro Gly Arg Gly Cys Gly Pro
            20                  25                  30

Cys Glu Pro Pro Cys Leu Cys Gly Pro Ala Pro Gly Ala Ala Cys Arg
        35                  40                  45

Val Asn Cys Ser Gly Arg Gly Leu Arg Thr Leu Gly Pro Ala Leu Arg
    50                  55                  60

Ile Pro Ala Asp Ala Thr Glu Leu Asp Val Ser His Asn Leu Leu Arg
65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Gln Trp Ala Glu Glu Gln Gln
    130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Ala Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285
```

-continued

```
Leu Ala Ala Phe His Ile Ala Ala Pro Leu Pro Val Thr Asp Thr Arg
    290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
        355                 360                 365

Ser Asp Glu Ser Leu Asp Leu Ser Ile Gln Asn Arg Gly Gly Ser Gly
    370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
                405                 410                 415

Gly His Cys Tyr Arg Leu Val Val Glu Lys Ala Ala Trp Leu Gln Ala
            420                 425                 430

Gln Glu Gln Cys Gln Ala Trp Ala Gly Ala Ala Leu Ala Met Val Asp
        435                 440                 445

Ser Pro Ala Val Gln Arg Phe Leu Val Ser Arg Val Thr Arg Ser Leu
    450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
            500                 505                 510

Pro Thr Gly Trp Cys Asn Thr Asp Leu Cys Ser Ala Pro His Ser Tyr
        515                 520                 525

Val Cys Glu Leu Gln Pro Gly Gly Pro Val Gln Asp Ala Glu Asn Leu
    530                 535                 540

Leu Val Gly Ala Pro Ser Gly Asp Leu Gln Gly Pro Leu Thr Pro Leu
545                 550                 555                 560

Ala Gln Gln Asp Gly Leu Ser Ala Pro His Glu Pro Val Glu Val Met
                565                 570                 575

Val Phe Pro Gly Leu Arg Leu Ser Arg Glu Ala Phe Leu Thr Thr Ala
            580                 585                 590

Glu Phe Gly Thr Gln Glu Leu Arg Arg Pro Ala Gln Leu Arg Leu Gln
        595                 600                 605

Val Tyr Arg Leu Leu Ser Thr Ala Gly Thr Pro Glu Asn Gly Ser Glu
    610                 615                 620

Pro Glu Ser Arg Ser Pro Asp Asn Arg Thr Gln Leu Ala Pro Ala Cys
625                 630                 635                 640

Met Pro Gly Gly Arg Trp Cys Pro Gly Ala Asn Ile Cys Leu Pro Leu
                645                 650                 655

Asp Ala Ser Cys His Pro Gln Ala Cys Ala Asn Gly Cys Thr Ser Gly
            660                 665                 670

Pro Gly Leu Pro Gly Ala Pro Tyr Ala Leu Trp Arg Glu Phe Leu Phe
        675                 680                 685

Ser Val Pro Ala Gly Pro Pro Ala Gln Tyr Ser Val Thr Leu His Gly
    690                 695                 700

Gln Asp Val Leu Met Leu Pro Gly Asp Leu Val Gly Leu Gln His Asp
```

-continued

```
705                 710                 715                 720

Ala Gly Pro Gly Ala Leu Leu His Cys Ser Pro Ala Pro Gly His Pro
                725                 730                 735

Gly Pro Arg Ala Pro Tyr Leu Ser Ala Asn Ala Ser Ser Trp Leu Pro
            740                 745                 750

His Leu Pro Ala Gln Leu Glu Gly Thr Trp Gly Cys Pro Ala Cys Ala
        755                 760                 765

Leu Arg Leu Leu Ala Gln Arg Glu Gln Leu Thr Val Leu Leu Gly Leu
    770                 775                 780

Arg Pro Asn Pro Gly Leu Arg Leu Pro Gly Arg Tyr Glu Val Arg Ala
785                 790                 795                 800

Glu Val Gly Asn Gly Val Ser Arg His Asn Leu Ser Cys Ser Phe Asp
                805                 810                 815

Val Val Ser Pro Val Ala Gly Leu Arg Val Ile Tyr Pro Ala Pro Arg
            820                 825                 830

Asp Gly Arg Leu Tyr Val Pro Thr Asn Gly Ser Ala Leu Val Leu Gln
        835                 840                 845

Val Asp Ser Gly Ala Asn Ala Thr Ala Thr Ala Arg Trp Pro Gly Gly
    850                 855                 860

Ser Leu Ser Ala Arg Phe Glu Asn Val Cys Pro Ala Leu Val Ala Thr
865                 870                 875                 880

Phe Val Pro Ala Cys Pro Trp Glu Thr Asn Asp Thr Leu Phe Ser Val
                885                 890                 895

Val Ala Leu Pro Trp Leu Ser Glu Gly Glu His Val Val Asp Val Val
            900                 905                 910

Val Glu Asn Ser Ala Ser Arg Ala Asn Leu Ser Leu Arg Val Thr Ala
        915                 920                 925

Glu Glu Pro Ile Cys Gly Leu Arg Ala Thr Pro Ser Pro Glu Ala Arg
    930                 935                 940

Val Leu Gln Gly Val Leu Val Arg Tyr Ser Pro Val Val Glu Ala Gly
945                 950                 955                 960

Ser Asp Met Val Phe Arg Trp Thr Ile Asn Asp Lys Gln Ser Leu Thr
                965                 970                 975

Phe Gln Asn Val Val Phe Asn Val Ile Tyr Gln Ser Ala Ala Val Phe
            980                 985                 990

Lys Leu Ser Leu Thr Ala Ser Asn  His Val Ser Asn Val  Thr Val Asn
        995                 1000                 1005

Tyr Asn  Val Thr Val Glu Arg  Met Asn Arg Met Gln  Gly Leu Gln
    1010                 1015                 1020

Val Ser  Thr Val Pro Ala Val  Leu Ser Pro Asn Ala  Thr Leu Ala
    1025                 1030                 1035

Leu Thr  Ala Gly Val Leu Val  Asp Ser Ala Val Glu  Val Ala Phe
    1040                 1045                 1050

Leu Trp  Thr Phe Gly Asp Gly  Glu Gln Ala Leu His  Gln Phe Gln
    1055                 1060                 1065

Pro Pro  Tyr Asn Glu Ser Phe  Pro Val Pro Asp Pro  Ser Val Ala
    1070                 1075                 1080

Gln Val  Leu Val Glu His Asn  Val Thr His Thr Tyr  Ala Ala Pro
    1085                 1090                 1095

Gly Glu  Tyr Leu Leu Thr Val  Leu Ala Ser Asn Ala  Phe Glu Asn
    1100                 1105                 1110

Leu Thr  Gln Gln Val Pro Val  Ser Val Arg Ala Ser  Leu Pro Ser
    1115                 1120                 1125
```

```
Val Ala Val Gly Val Ser Asp Gly Val Leu Val Ala Gly Arg Pro
    1130                1135                1140

Val Thr Phe Tyr Pro His Pro Leu Pro Ser Pro Gly Gly Val Leu
    1145                1150                1155

Tyr Thr Trp Asp Phe Gly Asp Gly Ser Pro Val Leu Thr Gln Ser
    1160                1165                1170

Gln Pro Ala Ala Asn His Thr Tyr Ala Ser Arg Gly Thr Tyr His
    1175                1180                1185

Val Arg Leu Glu Val Asn Asn Thr Val Ser Gly Ala Ala Ala Gln
    1190                1195                1200

Ala Asp Val Arg Val Phe Glu Glu Leu Arg Gly Leu Ser Val Asp
    1205                1210                1215

Met Ser Leu Ala Val Glu Gln Gly Ala Pro Val Val Val Ser Ala
    1220                1225                1230

Ala Val Gln Thr Gly Asp Asn Ile Thr Trp Thr Phe Asp Met Gly
    1235                1240                1245

Asp Gly Thr Val Leu Ser Gly Pro Glu Ala Thr Val Glu His Val
    1250                1255                1260

Tyr Leu Arg Ala Gln Asn Cys Thr Val Thr Val Gly Ala Gly Ser
    1265                1270                1275

Pro Ala Gly His Leu Ala Arg Ser Leu His Val Leu Val Phe Val
    1280                1285                1290

Leu Glu Val Leu Arg Val Glu Pro Ala Ala Cys Ile Pro Thr Gln
    1295                1300                1305

Pro Asp Ala Arg Leu Thr Ala Tyr Val Thr Gly Asn Pro Ala His
    1310                1315                1320

Tyr Leu Phe Asp Trp Thr Phe Gly Asp Gly Ser Ser Asn Thr Thr
    1325                1330                1335

Val Arg Gly Cys Pro Thr Val Thr His Asn Phe Thr Arg Ser Gly
    1340                1345                1350

Thr Phe Pro Leu Ala Leu Val Leu Ser Ser Arg Val Asn Arg Ala
    1355                1360                1365

His Tyr Phe Thr Ser Ile Cys Val Glu Pro Glu Val Gly Asn Val
    1370                1375                1380

Thr Leu Gln Pro Glu Arg Gln Phe Val Gln Leu Gly Asp Glu Ala
    1385                1390                1395

Trp Leu Val Ala Cys Ala Trp Pro Pro Phe Pro Tyr Arg Tyr Thr
    1400                1405                1410

Trp Asp Phe Gly Thr Glu Glu Ala Ala Pro Thr Arg Ala Arg Gly
    1415                1420                1425

Pro Glu Val Thr Phe Ile Tyr Arg Asp Pro Gly Ser Tyr Leu Val
    1430                1435                1440

Thr Val Thr Ala Ser Asn Asn Ile Ser Ala Ala Asn Asp Ser Ala
    1445                1450                1455

Leu Val Glu Val Gln Glu Pro Val Leu Val Thr Ser Ile Lys Val
    1460                1465                1470

Asn Gly Ser Leu Gly Leu Glu Leu Gln Gln Pro Tyr Leu Phe Ser
    1475                1480                1485

Ala Val Gly Arg Gly Arg Pro Ala Ser Tyr Leu Trp Asp Leu Gly
    1490                1495                1500

Asp Gly Gly Trp Leu Glu Gly Pro Glu Val Thr His Ala Tyr Asn
    1505                1510                1515
```

```
Ser Thr  Gly Asp Phe Thr Val  Arg Val Ala Gly Trp  Asn Glu Val
    1520                 1525                 1530

Ser Arg  Ser Glu Ala Trp Leu  Asn Val Thr Val Lys  Arg Arg Val
    1535                 1540                 1545

Arg Gly  Leu Val Val Asn Ala  Ser Arg Thr Val Val  Pro Leu Asn
    1550                 1555                 1560

Gly Ser  Val Ser Phe Ser Thr  Ser Leu Glu Ala Gly  Ser Asp Val
    1565                 1570                 1575

Arg Tyr  Ser Trp Val Leu Cys  Asp Arg Cys Thr Pro  Ile Pro Gly
    1580                 1585                 1590

Gly Pro  Thr Ile Ser Tyr Thr  Phe Arg Ser Val Gly  Thr Phe Asn
    1595                 1600                 1605

Ile Ile  Val Thr Ala Glu Asn  Glu Val Gly Ser Ala  Gln Asp Ser
    1610                 1615                 1620

Ile Phe  Val Tyr Val Leu Gln  Leu Ile Glu Gly Leu  Gln Val Val
    1625                 1630                 1635

Gly Gly  Gly Arg Tyr Phe Pro  Thr Asn His Thr Val  Gln Leu Gln
    1640                 1645                 1650

Ala Val  Val Arg Asp Gly Thr  Asn Val Ser Tyr Ser  Trp Thr Ala
    1655                 1660                 1665

Trp Arg  Asp Arg Gly Pro Ala  Leu Ala Gly Ser Gly  Lys Gly Phe
    1670                 1675                 1680

Ser Leu  Thr Val Leu Glu Ala  Gly Thr Tyr His Val  Gln Leu Arg
    1685                 1690                 1695

Ala Thr  Asn Met Leu Gly Ser  Ala Trp Ala Asp Cys  Thr Met Asp
    1700                 1705                 1710

Phe Val  Glu Pro Val Gly Trp  Leu Met Val Ala Ala  Ser Pro Asn
    1715                 1720                 1725

Pro Ala  Ala Val Asn Thr Ser  Val Thr Leu Ser Ala  Glu Leu Ala
    1730                 1735                 1740

Gly Gly  Ser Gly Val Val Tyr  Thr Trp Ser Leu Glu  Glu Gly Leu
    1745                 1750                 1755

Ser Trp  Glu Thr Ser Glu Pro  Phe Thr Thr His Ser  Phe Pro Thr
    1760                 1765                 1770

Pro Gly  Leu His Leu Val Thr  Met Thr Ala Gly Asn  Pro Leu Gly
    1775                 1780                 1785

Ser Ala  Asn Ala Thr Val Glu  Val Asp Val Gln Val  Pro Val Ser
    1790                 1795                 1800

Gly Leu  Ser Ile Arg Ala Ser  Glu Pro Gly Gly Ser  Phe Val Ala
    1805                 1810                 1815

Ala Gly  Ser Ser Val Pro Phe  Trp Gly Gln Leu Ala  Thr Gly Thr
    1820                 1825                 1830

Asn Val  Ser Trp Cys Trp Ala  Val Pro Gly Gly Ser  Ser Lys Arg
    1835                 1840                 1845

Gly Pro  His Val Thr Met Val  Phe Pro Asp Ala Gly  Thr Phe Ser
    1850                 1855                 1860

Ile Arg  Leu Asn Ala Ser Asn  Ala Val Ser Trp Val  Ser Ala Thr
    1865                 1870                 1875

Tyr Asn  Leu Thr Ala Glu Glu  Pro Ile Val Gly Leu  Val Leu Trp
    1880                 1885                 1890

Ala Ser  Ser Lys Val Val Ala  Pro Gly Gln Leu Val  His Phe Gln
    1895                 1900                 1905

Ile Leu  Leu Ala Ala Gly Ser  Ala Val Thr Phe Arg  Leu Gln Val
```

```
    1910                1915                1920

Gly Gly  Ala Asn Pro Glu Val  Leu Pro Gly Pro Arg  Phe Ser His
    1925                1930                1935

Ser Phe  Pro Arg Val Gly Asp  His Val Val Ser Val  Arg Gly Lys
    1940                1945                1950

Asn His  Val Ser Trp Ala Gln  Ala Gln Val Arg Ile  Val Val Leu
    1955                1960                1965

Glu Ala  Val Ser Gly Leu Gln  Val Pro Asn Cys Cys  Glu Pro Gly
    1970                1975                1980

Ile Ala  Thr Gly Thr Glu Arg  Asn Phe Thr Ala Arg  Val Gln Arg
    1985                1990                1995

Gly Ser  Arg Val Ala Tyr Ala  Trp Tyr Phe Ser Leu  Gln Lys Val
    2000                2005                2010

Gln Gly  Asp Ser Leu Val Ile  Leu Ser Gly Arg Asp  Val Thr Tyr
    2015                2020                2025

Thr Pro  Val Ala Ala Gly Leu  Leu Glu Ile Gln Val  Arg Ala Phe
    2030                2035                2040

Asn Ala  Leu Gly Ser Glu Asn  Arg Thr Leu Val Leu  Glu Val Gln
    2045                2050                2055

Asp Ala  Val Gln Tyr Val Ala  Leu Gln Ser Gly Pro  Cys Phe Thr
    2060                2065                2070

Asn Arg  Ser Ala Gln Phe Glu  Ala Ala Thr Ser Pro  Ser Pro Arg
    2075                2080                2085

Arg Val  Ala Tyr His Trp Asp  Phe Gly Asp Gly Ser  Pro Gly Gln
    2090                2095                2100

Asp Thr  Asp Glu Pro Arg Ala  Glu His Ser Tyr Leu  Arg Pro Gly
    2105                2110                2115

Asp Tyr  Arg Val Gln Val Asn  Ala Ser Asn Leu Val  Ser Phe Phe
    2120                2125                2130

Val Ala  Gln Ala Thr Val Thr  Val Gln Val Leu Ala  Cys Arg Glu
    2135                2140                2145

Pro Glu  Val Asp Val Val Leu  Pro Leu Gln Val Leu  Met Arg Arg
    2150                2155                2160

Ser Gln  Arg Asn Tyr Leu Glu  Ala His Val Asp Leu  Arg Asp Cys
    2165                2170                2175

Val Thr  Tyr Gln Thr Glu Tyr  Arg Trp Glu Val Tyr  Arg Thr Ala
    2180                2185                2190

Ser Cys  Gln Arg Pro Gly Arg  Pro Ala Arg Val Ala  Leu Pro Gly
    2195                2200                2205

Val Asp  Val Ser Arg Pro Arg  Leu Val Leu Pro Arg  Leu Ala Leu
    2210                2215                2220

Pro Val  Gly His Tyr Cys Phe  Val Phe Val Val Ser  Phe Gly Asp
    2225                2230                2235

Thr Pro  Leu Thr Gln Ser Ile  Gln Ala Asn Val Thr  Val Ala Pro
    2240                2245                2250

Glu Arg  Leu Val Pro Ile Ile  Glu Gly Gly Ser Tyr  Arg Val Trp
    2255                2260                2265

Ser Asp  Thr Arg Asp Leu Val  Leu Asp Gly Ser Glu  Ser Tyr Asp
    2270                2275                2280

Pro Asn  Leu Glu Asp Gly Asp  Gln Thr Pro Leu Ser  Phe His Trp
    2285                2290                2295

Ala Cys  Val Ala Ser Thr Gln  Arg Glu Ala Gly Gly  Cys Ala Leu
    2300                2305                2310
```

```
Asn Phe  Gly Pro Arg Gly Ser  Ser Thr Val Thr Ile  Pro Arg Glu
    2315                 2320                 2325

Arg Leu  Ala Ala Gly Val Glu  Tyr Thr Phe Ser Leu  Thr Val Trp
    2330                 2335                 2340

Lys Ala  Gly Arg Lys Glu Glu  Ala Thr Asn Gln Thr  Val Leu Ile
    2345                 2350                 2355

Arg Ser  Gly Arg Val Pro Ile  Val Ser Leu Glu Cys  Val Ser Cys
    2360                 2365                 2370

Lys Ala  Gln Ala Val Tyr Glu  Val Ser Arg Ser Ser  Tyr Val Tyr
    2375                 2380                 2385

Leu Glu  Gly Arg Cys Leu Asn  Cys Ser Ser Gly Ser  Lys Arg Gly
    2390                 2395                 2400

Arg Trp  Ala Ala Arg Thr Phe  Ser Asn Lys Thr Leu  Val Leu Asp
    2405                 2410                 2415

Glu Thr  Thr Thr Ser Thr Gly  Ser Ala Gly Met Arg  Leu Val Leu
    2420                 2425                 2430

Arg Arg  Gly Val Leu Arg Asp  Gly Glu Gly Tyr Thr  Phe Thr Leu
    2435                 2440                 2445

Thr Val  Leu Gly Arg Ser Gly  Glu Glu Glu Gly Cys  Ala Ser Ile
    2450                 2455                 2460

Arg Leu  Ser Pro Asn Arg Pro  Pro Leu Gly Gly Ser  Cys Arg Leu
    2465                 2470                 2475

Phe Pro  Leu Gly Ala Val His  Ala Leu Thr Thr Lys  Val His Phe
    2480                 2485                 2490

Glu Cys  Thr Gly Trp His Asp  Ala Glu Asp Ala Gly  Ala Pro Leu
    2495                 2500                 2505

Val Tyr  Ala Leu Leu Leu Arg  Arg Cys Arg Gln Gly  His Cys Glu
    2510                 2515                 2520

Glu Phe  Cys Val Tyr Lys Gly  Ser Leu Ser Ser Tyr  Gly Ala Val
    2525                 2530                 2535

Leu Pro  Pro Gly Phe Arg Pro  His Phe Glu Val Gly  Leu Ala Val
    2540                 2545                 2550

Val Val  Gln Asp Gln Leu Gly  Ala Ala Val Val Ala  Leu Asn Arg
    2555                 2560                 2565

Ser Leu  Ala Ile Thr Leu Pro  Glu Pro Asn Gly Ser  Ala Thr Gly
    2570                 2575                 2580

Leu Thr  Val Trp Leu His Gly  Leu Thr Ala Ser Val  Leu Pro Gly
    2585                 2590                 2595

Leu Leu  Arg Gln Ala Asp Pro  Gln His Val Ile Glu  Tyr Ser Leu
    2600                 2605                 2610

Ala Leu  Val Thr Val Leu Asn  Glu Tyr Glu Arg Ala  Leu Asp Val
    2615                 2620                 2625

Ala Ala  Glu Pro Lys His Glu  Arg Gln His Arg Ala  Gln Ile Arg
    2630                 2635                 2640

Lys Asn  Ile Thr Glu Thr Leu  Val Ser Leu Arg Val  His Thr Val
    2645                 2650                 2655

Asp Asp  Ile Gln Gln Ile Ala  Ala Ala Leu Ala Gln  Cys Met Gly
    2660                 2665                 2670

Pro Ser  Arg Glu Leu Val Cys  Arg Ser Cys Leu Lys  Gln Thr Leu
    2675                 2680                 2685

His Lys  Leu Glu Ala Met Met  Leu Ile Leu Gln Ala  Glu Thr Thr
    2690                 2695                 2700
```

```
Ala Gly  Thr Val Thr Pro Thr  Ala Ile Gly Asp Ser  Ile Leu Asn
    2705                 2710                 2715

Ile Thr  Gly Asp Leu Ile His  Leu Ala Ser Ser Asp  Val Arg Ala
    2720                 2725                 2730

Pro Gln  Pro Ser Glu Leu Gly  Ala Glu Ser Pro Ser  Arg Met Val
    2735                 2740                 2745

Ala Ser  Gln Ala Tyr Asn Leu  Thr Ser Ala Leu Met  Arg Ile Leu
    2750                 2755                 2760

Met Arg  Ser Arg Val Leu Asn  Glu Glu Pro Leu Thr  Leu Ala Gly
    2765                 2770                 2775

Glu Glu  Ile Val Ala Gln Gly  Lys Arg Ser Asp Pro  Arg Ser Leu
    2780                 2785                 2790

Leu Cys  Tyr Gly Gly Ala Pro  Gly Pro Gly Cys His  Phe Ser Ile
    2795                 2800                 2805

Pro Glu  Ala Phe Ser Gly Ala  Leu Ala Asn Leu Ser  Asp Val Val
    2810                 2815                 2820

Gln Leu  Ile Phe Leu Val Asp  Ser Asn Pro Phe Pro  Phe Gly Tyr
    2825                 2830                 2835

Ile Ser  Asn Tyr Thr Val Ser  Thr Lys Val Ala Ser  Met Ala Phe
    2840                 2845                 2850

Gln Thr  Gln Ala Gly Ala Gln  Ile Pro Ile Glu Arg  Leu Ala Ser
    2855                 2860                 2865

Glu Arg  Ala Ile Thr Val Lys  Val Pro Asn Asn Ser  Asp Trp Ala
    2870                 2875                 2880

Ala Arg  Gly His Arg Ser Ser  Ala Asn Ser Ala Asn  Ser Val Val
    2885                 2890                 2895

Val Gln  Pro Gln Ala Ser Val  Gly Ala Val Val Thr  Leu Asp Ser
    2900                 2905                 2910

Ser Asn  Pro Ala Ala Gly Leu  His Leu Gln Leu Asn  Tyr Thr Leu
    2915                 2920                 2925

Leu Asp  Gly His Tyr Leu Ser  Glu Glu Pro Glu Pro  Tyr Leu Ala
    2930                 2935                 2940

Val Tyr  Leu His Ser Glu Pro  Arg Pro Asn Glu His  Asn Cys Ser
    2945                 2950                 2955

Ala Ser  Arg Arg Ile Arg Pro  Glu Ser Leu Gln Gly  Ala Asp His
    2960                 2965                 2970

Arg Pro  Tyr Thr Phe Phe Ile  Ser Pro Gly Ser Arg  Asp Pro Ala
    2975                 2980                 2985

Gly Ser  Tyr His Leu Asn Leu  Ser Ser His Phe Arg  Trp Ser Ala
    2990                 2995                 3000

Leu Gln  Val Ser Val Gly Leu  Tyr Thr Ser Leu Cys  Gln Tyr Phe
    3005                 3010                 3015

Ser Glu  Glu Asp Met Val Trp  Arg Thr Glu Gly Leu  Leu Pro Leu
    3020                 3025                 3030

Glu Glu  Thr Ser Pro Arg Gln  Ala Val Cys Leu Thr  Arg His Leu
    3035                 3040                 3045

Thr Ala  Phe Gly Ala Ser Leu  Phe Val Pro Pro Ser  His Val Arg
    3050                 3055                 3060

Phe Val  Phe Pro Glu Pro Thr  Ala Asp Val Asn Tyr  Ile Val Met
    3065                 3070                 3075

Leu Thr  Cys Ala Val Cys Leu  Val Thr Tyr Met Val  Met Ala Ala
    3080                 3085                 3090

Ile Leu  His Lys Leu Asp Gln  Leu Asp Ala Ser Arg  Gly Arg Ala
```

```
    3095                3100                3105

Ile Pro  Phe Cys Gly Gln Arg  Gly Arg Phe Lys Tyr  Glu Ile Leu
    3110                3115                3120

Val Lys  Thr Gly Trp Gly Arg  Gly Ser Gly Thr Thr  Ala His Val
    3125                3130                3135

Gly Ile  Met Leu Tyr Gly Val  Asp Ser Arg Ser Gly  His Arg His
    3140                3145                3150

Leu Asp  Gly Asp Arg Ala Phe  His Arg Asn Ser Leu  Asp Ile Phe
    3155                3160                3165

Arg Ile  Ala Thr Pro His Ser  Leu Gly Ser Val Trp  Lys Ile Arg
    3170                3175                3180

Val Trp  His Asp Asn Lys Gly  Leu Ser Pro Ala Trp  Phe Leu Gln
    3185                3190                3195

His Val  Ile Val Arg Asp Leu  Gln Thr Ala Arg Ser  Ala Phe Phe
    3200                3205                3210

Leu Val  Asn Asp Trp Leu Ser  Val Glu Thr Glu Ala  Asn Gly Gly
    3215                3220                3225

Leu Val  Glu Lys Glu Val Leu  Ala Ala Ser Asp Ala  Ala Leu Leu
    3230                3235                3240

Arg Phe  Arg Arg Leu Leu Val  Ala Glu Leu Gln Arg  Gly Phe Phe
    3245                3250                3255

Asp Lys  His Ile Trp Leu Ser  Ile Trp Asp Arg Pro  Pro Arg Ser
    3260                3265                3270

Arg Phe  Thr Arg Ile Gln Arg  Ala Thr Cys Cys Val  Leu Leu Ile
    3275                3280                3285

Cys Leu  Phe Leu Gly Ala Asn  Ala Val Trp Tyr Gly  Ala Val Gly
    3290                3295                3300

Asp Ser  Ala Tyr Ser Thr Gly  His Val Ser Arg Leu  Ser Pro Leu
    3305                3310                3315

Ser Val  Asp Thr Val Ala Val  Gly Leu Val Ser Ser  Val Val Val
    3320                3325                3330

Tyr Pro  Val Tyr Leu Ala Ile  Leu Phe Leu Phe Arg  Met Ser Arg
    3335                3340                3345

Ser Lys  Val Ala Gly Ser Pro  Ser Pro Thr Pro Ala  Gly Gln Gln
    3350                3355                3360

Val Leu  Asp Ile Asp Ser Cys  Leu Asp Ser Ser Val  Leu Asp Ser
    3365                3370                3375

Ser Phe  Leu Thr Phe Ser Gly  Leu His Ala Glu Gln  Ala Phe Val
    3380                3385                3390

Gly Gln  Met Lys Ser Asp Leu  Phe Leu Asp Asp Ser  Lys Ser Leu
    3395                3400                3405

Val Cys  Trp Pro Ser Gly Glu  Gly Thr Leu Ser Trp  Pro Asp Leu
    3410                3415                3420

Leu Ser  Asp Pro Ser Ile Val  Gly Ser Asn Leu Arg  Gln Leu Ala
    3425                3430                3435

Arg Gly  Gln Ala Gly His Gly  Leu Gly Pro Glu Glu  Asp Gly Phe
    3440                3445                3450

Ser Leu  Ala Ser Pro Tyr Ser  Pro Ala Lys Ser Phe  Ser Ala Ser
    3455                3460                3465

Asp Glu  Asp Leu Ile Gln Gln  Val Leu Ala Glu Gly  Val Ser Ser
    3470                3475                3480

Pro Ala  Pro Thr Gln Asp Thr  His Met Glu Thr Asp  Leu Leu Ser
    3485                3490                3495
```

-continued

```
Ser Leu Ser Ser Thr Pro Gly Glu Lys Thr Glu Thr Leu Ala Leu
    3500                3505                3510

Gln Arg Leu Gly Glu Leu Gly Pro Pro Ser Pro Gly Leu Asn Trp
    3515                3520                3525

Glu Gln Pro Gln Ala Ala Arg Leu Ser Arg Thr Gly Leu Val Glu
    3530                3535                3540

Gly Leu Arg Lys Arg Leu Leu Pro Ala Trp Cys Ala Ser Leu Ala
    3545                3550                3555

His Gly Leu Ser Leu Leu Leu Val Ala Val Ala Val Ala Val Ser
    3560                3565                3570

Gly Trp Val Gly Ala Ser Phe Pro Pro Gly Val Ser Val Ala Trp
    3575                3580                3585

Leu Leu Ser Ser Ser Ala Ser Phe Leu Ala Ser Phe Leu Gly Trp
    3590                3595                3600

Glu Pro Leu Lys Val Leu Leu Glu Ala Leu Tyr Phe Ser Leu Val
    3605                3610                3615

Ala Lys Arg Leu His Pro Asp Glu Asp Asp Thr Leu Val Glu Ser
    3620                3625                3630

Pro Ala Val Thr Pro Val Ser Ala Arg Val Pro Arg Val Arg Pro
    3635                3640                3645

Pro His Gly Phe Ala Leu Phe Leu Ala Lys Glu Glu Ala Arg Lys
    3650                3655                3660

Val Lys Arg Leu His Gly Met Leu Arg Ser Leu Leu Val Tyr Met
    3665                3670                3675

Leu Phe Leu Leu Val Thr Leu Leu Ala Ser Tyr Gly Asp Ala Ser
    3680                3685                3690

Cys His Gly His Ala Tyr Arg Leu Gln Ser Ala Ile Lys Gln Glu
    3695                3700                3705

Leu His Ser Arg Ala Phe Leu Ala Ile Thr Arg Ser Glu Glu Leu
    3710                3715                3720

Trp Pro Trp Met Ala His Val Leu Leu Pro Tyr Val His Gly Asn
    3725                3730                3735

Gln Ser Ser Pro Glu Leu Gly Pro Pro Arg Leu Arg Gln Val Arg
    3740                3745                3750

Leu Gln Glu Ala Leu Tyr Pro Asp Pro Pro Gly Pro Arg Val His
    3755                3760                3765

Thr Cys Ser Ala Ala Gly Gly Phe Ser Thr Ser Asp Tyr Asp Val
    3770                3775                3780

Gly Trp Glu Ser Pro His Asn Gly Ser Gly Thr Trp Ala Tyr Ser
    3785                3790                3795

Ala Pro Asp Leu Leu Gly Ala Trp Ser Trp Gly Ser Cys Ala Val
    3800                3805                3810

Tyr Asp Ser Gly Gly Tyr Val Gln Glu Leu Gly Leu Ser Leu Glu
    3815                3820                3825

Glu Ser Arg Asp Arg Leu Arg Phe Leu Gln Leu His Asn Trp Leu
    3830                3835                3840

Asp Asn Arg Ser Arg Ala Val Phe Leu Glu Leu Thr Arg Tyr Ser
    3845                3850                3855

Pro Ala Val Gly Leu His Ala Ala Val Thr Leu Arg Leu Glu Phe
    3860                3865                3870

Pro Ala Ala Gly Arg Ala Leu Ala Ala Leu Ser Val Arg Pro Phe
    3875                3880                3885
```

Ala Leu Arg Arg Leu Ser Ala Gly Leu Ser Leu Pro Leu Leu Thr
3890 3895 3900

Ser Val Cys Leu Leu Leu Phe Ala Val His Phe Ala Val Ala Glu
3905 3910 3915

Ala Arg Thr Trp His Arg Glu Gly Arg Trp Arg Val Leu Arg Leu
3920 3925 3930

Gly Ala Trp Ala Arg Trp Leu Leu Val Ala Leu Thr Ala Ala Thr
3935 3940 3945

Ala Leu Val Arg Leu Ala Gln Leu Gly Ala Ala Asp Arg Gln Trp
3950 3955 3960

Thr Arg Phe Val Arg Gly Arg Pro Arg Arg Phe Thr Ser Phe Asp
3965 3970 3975

Gln Val Ala His Val Ser Ser Ala Ala Arg Gly Leu Ala Ala Ser
3980 3985 3990

Leu Leu Phe Leu Leu Leu Val Lys Ala Ala Gln His Val Arg Phe
3995 4000 4005

Val Arg Gln Trp Ser Val Phe Gly Lys Thr Leu Cys Arg Ala Leu
4010 4015 4020

Pro Glu Leu Leu Gly Val Thr Leu Gly Leu Val Val Leu Gly Val
4025 4030 4035

Ala Tyr Ala Gln Leu Ala Ile Leu Leu Val Ser Ser Cys Val Asp
4040 4045 4050

Ser Leu Trp Ser Val Ala Gln Ala Leu Leu Val Leu Cys Pro Gly
4055 4060 4065

Thr Gly Leu Ser Thr Leu Cys Pro Ala Glu Ser Trp His Leu Ser
4070 4075 4080

Pro Leu Leu Cys Val Gly Leu Trp Ala Leu Arg Leu Trp Gly Ala
4085 4090 4095

Leu Arg Leu Gly Ala Val Ile Leu Arg Trp Arg Tyr His Ala Leu
4100 4105 4110

Arg Gly Glu Leu Tyr Arg Pro Ala Trp Glu Pro Gln Asp Tyr Glu
4115 4120 4125

Met Val Glu Leu Phe Leu Arg Arg Leu Arg Leu Trp Met Gly Leu
4130 4135 4140

Ser Lys Val Lys Glu Phe Arg His Lys Val Arg Phe Glu Gly Met
4145 4150 4155

Glu Pro Leu Pro Ser Arg Ser Ser Arg Gly Ser Lys Val Ser Pro
4160 4165 4170

Asp Val Pro Pro Pro Ser Ala Gly Ser Asp Ala Ser His Pro Ser
4175 4180 4185

Thr Ser Ser Ser Gln Leu Asp Gly Leu Ser Val Ser Leu Gly Arg
4190 4195 4200

Leu Gly Thr Arg Cys Glu Pro Glu Pro Ser Arg Leu Gln Ala Val
4205 4210 4215

Phe Glu Ala Leu Leu Thr Gln Phe Asp Arg Leu Asn Gln Ala Thr
4220 4225 4230

Glu Asp Val Tyr Gln Leu Glu Gln Gln Leu His Ser Leu Gln Gly
4235 4240 4245

Arg Arg Ser Ser Arg Ala Pro Ala Gly Ser Ser Arg Gly Pro Ser
4250 4255 4260

Pro Gly Leu Arg Pro Ala Leu Pro Ser Arg Leu Ala Arg Ala Ser
4265 4270 4275

Arg Gly Val Asp Leu Ala Thr Gly Pro Ser Arg Thr Pro Leu Arg 4280 4285 4290

Ala Lys Asn Lys Val His Pro Ser Ser Thr
4295 4300

<210> SEQ ID NO 3
<211> LENGTH: 29
<212> TYPE: DNA
<213> ORGANISM: Artificial sequence
<220> FEATURE:
<223> OTHER INFORMATION: PCR primer BPF14

<400> SEQUENCE: 3
ccatccacct gctgtgtgac ctggtaaat 29

<210> SEQ ID NO 4
<211> LENGTH: 26
<212> TYPE: DNA
<213> ORGANISM: Artificial sequence
<220> FEATURE:
<223> OTHER INFORMATION: PCR primer BPR9

<400> SEQUENCE: 4
ccacctcatc gccccttcct aagcat 26

<210> SEQ ID NO 5
<211> LENGTH: 31
<212> TYPE: DNA
<213> ORGANISM: Artificial sequence
<220> FEATURE:
<223> OTHER INFORMATION: PCR primer BPF9

<400> SEQUENCE: 5
attttttgag atggagcttc actcttgcag g 31

<210> SEQ ID NO 6
<211> LENGTH: 20
<212> TYPE: DNA
<213> ORGANISM: Artificial sequence
<220> FEATURE:
<223> OTHER INFORMATION: PCR primer BPR4

<400> SEQUENCE: 6
cgctcggcag gcccctaacc 20

<210> SEQ ID NO 7
<211> LENGTH: 21
<212> TYPE: DNA
<213> ORGANISM: Artificial sequence
<220> FEATURE:
<223> OTHER INFORMATION: PCR primer BPF12

<400> SEQUENCE: 7
ccgcccccag gagcctagac g 21

<210> SEQ ID NO 8
<211> LENGTH: 27
<212> TYPE: DNA
<213> ORGANISM: Artificial sequence
<220> FEATURE:
<223> OTHER INFORMATION: PCR primer BPR5

<400> SEQUENCE: 8
catcctgttc atccgctcca cggttac 27

<210> SEQ ID NO 9

<211> LENGTH: 20
<212> TYPE: DNA
<213> ORGANISM: Artificial sequence
<220> FEATURE:
<223> OTHER INFORMATION: PCR primer F13

<400> SEQUENCE: 9
tggagggagg gacgccaatc 20

<210> SEQ ID NO 10
<211> LENGTH: 20
<212> TYPE: DNA
<213> ORGANISM: Artificial sequence
<220> FEATURE:
<223> OTHER INFORMATION: PCR primer R27

<400> SEQUENCE: 10
gtcaacgtgg gcctccaagt 20

<210> SEQ ID NO 11
<211> LENGTH: 21
<212> TYPE: DNA
<213> ORGANISM: Artificial sequence
<220> FEATURE:
<223> OTHER INFORMATION: PCR primer F26

<400> SEQUENCE: 11
agcgcaacta cttggaggcc c 21

<210> SEQ ID NO 12
<211> LENGTH: 28
<212> TYPE: DNA
<213> ORGANISM: Artificial sequence
<220> FEATURE:
<223> OTHER INFORMATION: PCR primer R2

<400> SEQUENCE: 12
gcagggtgag caggtggggc catcctac 28

<210> SEQ ID NO 13
<211> LENGTH: 26
<212> TYPE: DNA
<213> ORGANISM: Artificial sequence
<220> FEATURE:
<223> OTHER INFORMATION: PCR primer BPF15

<400> SEQUENCE: 13
gaggctgtgg gggtccagtc aagtgg 26

<210> SEQ ID NO 14
<211> LENGTH: 25
<212> TYPE: DNA
<213> ORGANISM: Artificial sequence
<220> FEATURE:
<223> OTHER INFORMATION: PCR primer BPR12

<400> SEQUENCE: 14
agggaggcag aggaaagggc cgaac 25

<210> SEQ ID NO 15
<211> LENGTH: 24
<212> TYPE: DNA
<213> ORGANISM: Artificial sequence
<220> FEATURE:
<223> OTHER INFORMATION: PCR primer BPF6

<400> SEQUENCE: 15
ccccgtcctc cccgtccttt tgtc 24

<210> SEQ ID NO 16
<211> LENGTH: 21
<212> TYPE: DNA
<213> ORGANISM: Artificial sequence
<220> FEATURE:
<223> OTHER INFORMATION: PCR primer BPR6

<400> SEQUENCE: 16
aagcgcaaaa gggctgcgtc g 21

<210> SEQ ID NO 17
<211> LENGTH: 22
<212> TYPE: DNA
<213> ORGANISM: Artificial sequence
<220> FEATURE:
<223> OTHER INFORMATION: PCR primer BPF13

<400> SEQUENCE: 17
ggccctccct gccttctagg cg 22

<210> SEQ ID NO 18
<211> LENGTH: 21
<212> TYPE: DNA
<213> ORGANISM: Artificial sequence
<220> FEATURE:
<223> OTHER INFORMATION: PCR primer KG8R25

<400> SEQUENCE: 18
gttgcagcca agcccatgtt a 21

<210> SEQ ID NO 19
<211> LENGTH: 19
<212> TYPE: DNA
<213> ORGANISM: Artificial sequence
<220> FEATURE:
<223> OTHER INFORMATION: PCR primer 1F1

<400> SEQUENCE: 19
ggtcgcgctg tggcgaagg 19

<210> SEQ ID NO 20
<211> LENGTH: 16
<212> TYPE: DNA
<213> ORGANISM: Artificial sequence
<220> FEATURE:
<223> OTHER INFORMATION: PCR primer 1R1

<400> SEQUENCE: 20
cggcgggcgg catcgt 16

<210> SEQ ID NO 21
<211> LENGTH: 16
<212> TYPE: DNA
<213> ORGANISM: Artificial sequence
<220> FEATURE:
<223> OTHER INFORMATION: PCR primer 1F2

<400> SEQUENCE: 21
acggcggggc catgcg 16

<210> SEQ ID NO 22
<211> LENGTH: 18
<212> TYPE: DNA

<213> ORGANISM: Artificial sequence
<220> FEATURE:
<223> OTHER INFORMATION: PCR primer 1R2

<400> SEQUENCE: 22
gcgtcctggc ccgcgtcc 18

<210> SEQ ID NO 23
<211> LENGTH: 20
<212> TYPE: DNA
<213> ORGANISM: Artificial sequence
<220> FEATURE:
<223> OTHER INFORMATION: PCR primer 2F

<400> SEQUENCE: 23
ttggggatgc tggcaatgtg 20

<210> SEQ ID NO 24
<211> LENGTH: 20
<212> TYPE: DNA
<213> ORGANISM: Artificial sequence
<220> FEATURE:
<223> OTHER INFORMATION: PCR primer 2R

<400> SEQUENCE: 24
gggattcggc aaagctgatg 20

<210> SEQ ID NO 25
<211> LENGTH: 20
<212> TYPE: DNA
<213> ORGANISM: Artificial sequence
<220> FEATURE:
<223> OTHER INFORMATION: PCR primer 3F

<400> SEQUENCE: 25
ccatcagctt tgccgaatcc 20

<210> SEQ ID NO 26
<211> LENGTH: 20
<212> TYPE: DNA
<213> ORGANISM: Artificial sequence
<220> FEATURE:
<223> OTHER INFORMATION: PCR primer 3R

<400> SEQUENCE: 26
agggcagaag ggatattggg 20

<210> SEQ ID NO 27
<211> LENGTH: 20
<212> TYPE: DNA
<213> ORGANISM: Artificial sequence
<220> FEATURE:
<223> OTHER INFORMATION: PCR primer 4F

<400> SEQUENCE: 27
agacccttcc caccagacct 20

<210> SEQ ID NO 28
<211> LENGTH: 19
<212> TYPE: DNA
<213> ORGANISM: Artificial sequence
<220> FEATURE:
<223> OTHER INFORMATION: PCR primer 4R

<400> SEQUENCE: 28
tgagccctgc ccagtgtct 19

<210> SEQ ID NO 29
<211> LENGTH: 21
<212> TYPE: DNA
<213> ORGANISM: Artificial sequence
<220> FEATURE:
<223> OTHER INFORMATION: PCR primer 5F1

<400> SEQUENCE: 29
gagccaggag gagcagaacc c 21

<210> SEQ ID NO 30
<211> LENGTH: 21
<212> TYPE: DNA
<213> ORGANISM: Artificial sequence
<220> FEATURE:
<223> OTHER INFORMATION: PCR primer 5R1

<400> SEQUENCE: 30
agagggacag gcaggcaaag g 21

<210> SEQ ID NO 31
<211> LENGTH: 18
<212> TYPE: DNA
<213> ORGANISM: Artificial sequence
<220> FEATURE:
<223> OTHER INFORMATION: PCR primer 5F2

<400> SEQUENCE: 31
cccagccctc cagtgcct 18

<210> SEQ ID NO 32
<211> LENGTH: 20
<212> TYPE: DNA
<213> ORGANISM: Artificial sequence
<220> FEATURE:
<223> OTHER INFORMATION: PCR primer 5R2

<400> SEQUENCE: 32
cccaggcagc acatagcgat 20

<210> SEQ ID NO 33
<211> LENGTH: 18
<212> TYPE: DNA
<213> ORGANISM: Artificial sequence
<220> FEATURE:
<223> OTHER INFORMATION: PCR primer 5F3

<400> SEQUENCE: 33
ccgaggtgga tgccgctg 18

<210> SEQ ID NO 34
<211> LENGTH: 21
<212> TYPE: DNA
<213> ORGANISM: Artificial sequence
<220> FEATURE:
<223> OTHER INFORMATION: PCR primer 5R3

<400> SEQUENCE: 34
gaaggggagt gggcagcaga c 21

<210> SEQ ID NO 35
<211> LENGTH: 21
<212> TYPE: DNA
<213> ORGANISM: Artificial sequence
<220> FEATURE:

<223> OTHER INFORMATION: PCR primer 6F

<400> SEQUENCE: 35
cactgaccgt tgacaccctc g                                             21

<210> SEQ ID NO 36
<211> LENGTH: 21
<212> TYPE: DNA
<213> ORGANISM: Artificial sequence
<220> FEATURE:
<223> OTHER INFORMATION: PCR primer 6R

<400> SEQUENCE: 36
tgccccagtg cttcagagat c                                             21

<210> SEQ ID NO 37
<211> LENGTH: 19
<212> TYPE: DNA
<213> ORGANISM: Artificial sequence
<220> FEATURE:
<223> OTHER INFORMATION: PCR primer 7F

<400> SEQUENCE: 37
ggagtgccct gagccccct                                                19

<210> SEQ ID NO 38
<211> LENGTH: 19
<212> TYPE: DNA
<213> ORGANISM: Artificial sequence
<220> FEATURE:
<223> OTHER INFORMATION: PCR primer 7R

<400> SEQUENCE: 38
cccctaacca cagccagcg                                                19

<210> SEQ ID NO 39
<211> LENGTH: 21
<212> TYPE: DNA
<213> ORGANISM: Artificial sequence
<220> FEATURE:
<223> OTHER INFORMATION: PCR primer 8F

<400> SEQUENCE: 39
tctgttcgtc ctggtgtcct g                                             21

<210> SEQ ID NO 40
<211> LENGTH: 21
<212> TYPE: DNA
<213> ORGANISM: Artificial sequence
<220> FEATURE:
<223> OTHER INFORMATION: PCR primer 8R

<400> SEQUENCE: 40
gcaggagggc aggttgtaga a                                             21

<210> SEQ ID NO 41
<211> LENGTH: 20
<212> TYPE: DNA
<213> ORGANISM: Artificial sequence
<220> FEATURE:
<223> OTHER INFORMATION: PCR primer 9F

<400> SEQUENCE: 41
ggtaggggga gtctgggctt                                               20

<210> SEQ ID NO 42
<211> LENGTH: 17
<212> TYPE: DNA
<213> ORGANISM: Artificial sequence
<220> FEATURE:
<223> OTHER INFORMATION: PCR primer 9R

<400> SEQUENCE: 42
gaggccaccc cgagtcc 17

<210> SEQ ID NO 43
<211> LENGTH: 20
<212> TYPE: DNA
<213> ORGANISM: Artificial sequence
<220> FEATURE:
<223> OTHER INFORMATION: PCR primer 10F

<400> SEQUENCE: 43
gttgggcatc tctgacggtg 20

<210> SEQ ID NO 44
<211> LENGTH: 20
<212> TYPE: DNA
<213> ORGANISM: Artificial sequence
<220> FEATURE:
<223> OTHER INFORMATION: PCR primer 10R

<400> SEQUENCE: 44
ggaaggtggc ctgaggagat 20

<210> SEQ ID NO 45
<211> LENGTH: 17
<212> TYPE: DNA
<213> ORGANISM: Artificial sequence
<220> FEATURE:
<223> OTHER INFORMATION: PCR primer 11F2

<400> SEQUENCE: 45
ggggtccacg ggccatg 17

<210> SEQ ID NO 46
<211> LENGTH: 20
<212> TYPE: DNA
<213> ORGANISM: Artificial sequence
<220> FEATURE:
<223> OTHER INFORMATION: PCR primer 11R2

<400> SEQUENCE: 46
aagcccagca gcacggtgag 20

<210> SEQ ID NO 47
<211> LENGTH: 17
<212> TYPE: DNA
<213> ORGANISM: Artificial sequence
<220> FEATURE:
<223> OTHER INFORMATION: PCR primer 11midF

<400> SEQUENCE: 47
gcttgcagcc acggaac 17

<210> SEQ ID NO 48
<211> LENGTH: 20
<212> TYPE: DNA
<213> ORGANISM: Artificial sequence
<220> FEATURE:
<223> OTHER INFORMATION: PCR primer 11midR

<400> SEQUENCE: 48
gcagtgctac cactgagaac 20

<210> SEQ ID NO 49
<211> LENGTH: 23
<212> TYPE: DNA
<213> ORGANISM: Artificial sequence
<220> FEATURE:
<223> OTHER INFORMATION: PCR primer 11F1

<400> SEQUENCE: 49
tgcccctggg agaccaacga tac 23

<210> SEQ ID NO 50
<211> LENGTH: 22
<212> TYPE: DNA
<213> ORGANISM: Artificial sequence
<220> FEATURE:
<223> OTHER INFORMATION: PCR primer 11R1

<400> SEQUENCE: 50
ggctgctgcc ctcactggga ag 22

<210> SEQ ID NO 51
<211> LENGTH: 18
<212> TYPE: DNA
<213> ORGANISM: Artificial sequence
<220> FEATURE:
<223> OTHER INFORMATION: PCR primer 12F

<400> SEQUENCE: 51
gaggcgacag gctaaggg 18

<210> SEQ ID NO 52
<211> LENGTH: 25
<212> TYPE: DNA
<213> ORGANISM: Artificial sequence
<220> FEATURE:
<223> OTHER INFORMATION: Primer for PCR

<400> SEQUENCE: 52
aggtcaacgt gggcctccaa gtagt 25

<210> SEQ ID NO 53
<211> LENGTH: 19
<212> TYPE: DNA
<213> ORGANISM: Artificial sequence
<220> FEATURE:
<223> OTHER INFORMATION: Forward nested primer F32

<400> SEQUENCE: 53
gccttgcgca gcttggact 19

<210> SEQ ID NO 54
<211> LENGTH: 20
<212> TYPE: DNA
<213> ORGANISM: Artificial sequence
<220> FEATURE:
<223> OTHER INFORMATION: Second specific primer 31R

<400> SEQUENCE: 54
acagtgtctt gagtccaagc 20

<210> SEQ ID NO 55
<211> LENGTH: 30

<212> TYPE: DNA
<213> ORGANISM: Artificial sequence
<220> FEATURE:
<223> OTHER INFORMATION: PCR primer

<400> SEQUENCE: 55
ctggtgacct acatggtcat ggccgagatc 30

<210> SEQ ID NO 56
<211> LENGTH: 30
<212> TYPE: DNA
<213> ORGANISM: Artificial sequence
<220> FEATURE:
<223> OTHER INFORMATION: PCR primer

<400> SEQUENCE: 56
ggttgtctat cccgtctacc tggccctcct 30

<210> SEQ ID NO 57
<211> LENGTH: 25
<212> TYPE: DNA
<213> ORGANISM: Artificial sequence
<220> FEATURE:
<223> OTHER INFORMATION: PCR primer

<400> SEQUENCE: 57
gtccccagcc ccagcccacc tggcc 25

<210> SEQ ID NO 58
<211> LENGTH: 7
<212> TYPE: PRT
<213> ORGANISM: Homo sapiens

<400> SEQUENCE: 58

Trp Asp Phe Gly Asp Gly Ser
1               5

<210> SEQ ID NO 59
<211> LENGTH: 4
<212> TYPE: PRT
<213> ORGANISM: Homo sapiens

<400> SEQUENCE: 59

His Leu Thr Ala
1

<210> SEQ ID NO 60
<211> LENGTH: 27
<212> TYPE: DNA
<213> ORGANISM: Artificial sequence
<220> FEATURE:
<223> OTHER INFORMATION: PCR primer

<400> SEQUENCE: 60
gcagggtgag caggtggggc catccta 27

<210> SEQ ID NO 61
<211> LENGTH: 19
<212> TYPE: DNA
<213> ORGANISM: Artificial sequence
<220> FEATURE:
<223> OTHER INFORMATION: PCR primer 12R-2

<400> SEQUENCE: 61
catgaagcag agcagaagg 19

-continued

<210> SEQ ID NO 62
<211> LENGTH: 20
<212> TYPE: DNA
<213> ORGANISM: Artificial sequence
<220> FEATURE:
<223> OTHER INFORMATION: PCR primer 13F

<400> SEQUENCE: 62
tggagggagg gacgccaatc 20

<210> SEQ ID NO 63
<211> LENGTH: 19
<212> TYPE: DNA
<213> ORGANISM: Artificial sequence
<220> FEATURE:
<223> OTHER INFORMATION: PCR primer 13R

<400> SEQUENCE: 63
gaggctgggg ctgggacaa 19

<210> SEQ ID NO 64
<211> LENGTH: 18
<212> TYPE: DNA
<213> ORGANISM: Artificial sequence
<220> FEATURE:
<223> OTHER INFORMATION: PCR primer 14F

<400> SEQUENCE: 64
cccggttcac tcactgcg 18

<210> SEQ ID NO 65
<211> LENGTH: 20
<212> TYPE: DNA
<213> ORGANISM: Artificial sequence
<220> FEATURE:
<223> OTHER INFORMATION: PCR primer 14R

<400> SEQUENCE: 65
ccgtgctcag agcctgaaag 20

<210> SEQ ID NO 66
<211> LENGTH: 18
<212> TYPE: DNA
<213> ORGANISM: Artificial sequence
<220> FEATURE:
<223> OTHER INFORMATION: PCR primer 15F16

<400> SEQUENCE: 66
cgggtgggga gcaggtgg 18

<210> SEQ ID NO 67
<211> LENGTH: 21
<212> TYPE: DNA
<213> ORGANISM: Artificial sequence
<220> FEATURE:
<223> OTHER INFORMATION: PCR primer 15R16

<400> SEQUENCE: 67
gctctgggtc aggacagggg a 21

<210> SEQ ID NO 68
<211> LENGTH: 18
<212> TYPE: DNA
<213> ORGANISM: Artificial sequence
<220> FEATURE:
<223> OTHER INFORMATION: PCR primer 15F15

<400> SEQUENCE: 68
cgcctggggg tgttcttt 18

<210> SEQ ID NO 69
<211> LENGTH: 18
<212> TYPE: DNA
<213> ORGANISM: Artificial sequence
<220> FEATURE:
<223> OTHER INFORMATION: PCR primer 15R15

<400> SEQUENCE: 69
acgtgatgtt gtcgcccg 18

<210> SEQ ID NO 70
<211> LENGTH: 18
<212> TYPE: DNA
<213> ORGANISM: Artificial sequence
<220> FEATURE:
<223> OTHER INFORMATION: PCR primer 15F14

<400> SEQUENCE: 70
gcccccgtgg tggtcagc 18

<210> SEQ ID NO 71
<211> LENGTH: 18
<212> TYPE: DNA
<213> ORGANISM: Artificial sequence
<220> FEATURE:
<223> OTHER INFORMATION: PCR primer 15R14

<400> SEQUENCE: 71
caggctgcgt ggggatgc 18

<210> SEQ ID NO 72
<211> LENGTH: 18
<212> TYPE: DNA
<213> ORGANISM: Artificial sequence
<220> FEATURE:
<223> OTHER INFORMATION: PCR primer 15F13

<400> SEQUENCE: 72
ctggaggtgc tgcgcgtt 18

<210> SEQ ID NO 73
<211> LENGTH: 18
<212> TYPE: DNA
<213> ORGANISM: Artificial sequence
<220> FEATURE:
<223> OTHER INFORMATION: PCR primer 15R13

<400> SEQUENCE: 73
ctggctccac gcagatgc 18

<210> SEQ ID NO 74
<211> LENGTH: 18
<212> TYPE: DNA
<213> ORGANISM: Artificial sequence
<220> FEATURE:
<223> OTHER INFORMATION: PCR primer 15F12

<400> SEQUENCE: 74
cgtgaacagg gcgcatta 18

<210> SEQ ID NO 75

<211> LENGTH: 21
<212> TYPE: DNA
<213> ORGANISM: Artificial sequence
<220> FEATURE:
<223> OTHER INFORMATION: PCR primer 15R12

<400> SEQUENCE: 75
gcagcagaga tgttgttgga c 21

<210> SEQ ID NO 76
<211> LENGTH: 21
<212> TYPE: DNA
<213> ORGANISM: Artificial sequence
<220> FEATURE:
<223> OTHER INFORMATION: PCR primer 15F11

<400> SEQUENCE: 76
ccaggctcct atcttgtgac a 21

<210> SEQ ID NO 77
<211> LENGTH: 21
<212> TYPE: DNA
<213> ORGANISM: Artificial sequence
<220> FEATURE:
<223> OTHER INFORMATION: PCR primer 15R11

<400> SEQUENCE: 77
tgaagtcacc tgtgctgttg t 21

<210> SEQ ID NO 78
<211> LENGTH: 19
<212> TYPE: DNA
<213> ORGANISM: Artificial sequence
<220> FEATURE:
<223> OTHER INFORMATION: PCR primer 15F10

<400> SEQUENCE: 78
ctacctgtgg gatctgggg 19

<210> SEQ ID NO 79
<211> LENGTH: 18
<212> TYPE: DNA
<213> ORGANISM: Artificial sequence
<220> FEATURE:
<223> OTHER INFORMATION: PCR primer 15R10

<400> SEQUENCE: 79
tgctgaagct cacgctcc 18

<210> SEQ ID NO 80
<211> LENGTH: 20
<212> TYPE: DNA
<213> ORGANISM: Artificial sequence
<220> FEATURE:
<223> OTHER INFORMATION: PCR primer 15F9

<400> SEQUENCE: 80
gggctcgtcg tcaatgcaag 20

<210> SEQ ID NO 81
<211> LENGTH: 20
<212> TYPE: DNA
<213> ORGANISM: Artificial sequence
<220> FEATURE:
<223> OTHER INFORMATION: PCR primer 15R9

<400> SEQUENCE: 81
caccacctgc agcccctcta 20

<210> SEQ ID NO 82
<211> LENGTH: 20
<212> TYPE: DNA
<213> ORGANISM: Artificial sequence
<220> FEATURE:
<223> OTHER INFORMATION: PCR primer 15F8

<400> SEQUENCE: 82
ccgcccagga cagcatcttc 20

<210> SEQ ID NO 83
<211> LENGTH: 18
<212> TYPE: DNA
<213> ORGANISM: Artificial sequence
<220> FEATURE:
<223> OTHER INFORMATION: PCR primer 15R8

<400> SEQUENCE: 83
cgctgcccag catgttgg 18

<210> SEQ ID NO 84
<211> LENGTH: 19
<212> TYPE: DNA
<213> ORGANISM: Artificial sequence
<220> FEATURE:
<223> OTHER INFORMATION: PCR primer 15F7

<400> SEQUENCE: 84
cggcaaaggc ttctcgctc 19

<210> SEQ ID NO 85
<211> LENGTH: 20
<212> TYPE: DNA
<213> ORGANISM: Artificial sequence
<220> FEATURE:
<223> OTHER INFORMATION: PCR primer 15R7

<400> SEQUENCE: 85
ccgggtgtgg ggaagctatg 20

<210> SEQ ID NO 86
<211> LENGTH: 21
<212> TYPE: DNA
<213> ORGANISM: Artificial sequence
<220> FEATURE:
<223> OTHER INFORMATION: PCR primer 15F6

<400> SEQUENCE: 86
cgagccattt accacccata g 21

<210> SEQ ID NO 87
<211> LENGTH: 19
<212> TYPE: DNA
<213> ORGANISM: Artificial sequence
<220> FEATURE:
<223> OTHER INFORMATION: PCR primer 15R6

<400> SEQUENCE: 87
gcccagcacc agctcacat 19

<210> SEQ ID NO 88
<211> LENGTH: 19
<212> TYPE: DNA

<213> ORGANISM: Artificial sequence
<220> FEATURE:
<223> OTHER INFORMATION: PCR primer 15F5

<400> SEQUENCE: 88
ccacgggcac caatgtgag 19

<210> SEQ ID NO 89
<211> LENGTH: 20
<212> TYPE: DNA
<213> ORGANISM: Artificial sequence
<220> FEATURE:
<223> OTHER INFORMATION: PCR primer 15R5

<400> SEQUENCE: 89
ggcagccagc aggatctgaa 20

<210> SEQ ID NO 90
<211> LENGTH: 18
<212> TYPE: DNA
<213> ORGANISM: Artificial sequence
<220> FEATURE:
<223> OTHER INFORMATION: PCR pimer 15F4

<400> SEQUENCE: 90
cagcagcaag gtggtggc 18

<210> SEQ ID NO 91
<211> LENGTH: 18
<212> TYPE: DNA
<213> ORGANISM: Artificial sequence
<220> FEATURE:
<223> OTHER INFORMATION: PCR primer 15R4

<400> SEQUENCE: 91
gcgtaggcga cccgagag 18

<210> SEQ ID NO 92
<211> LENGTH: 21
<212> TYPE: DNA
<213> ORGANISM: Artificial sequence
<220> FEATURE:
<223> OTHER INFORMATION: PCR primer 15F3

<400> SEQUENCE: 92
acgggcactg agaggaactt c 21

<210> SEQ ID NO 93
<211> LENGTH: 20
<212> TYPE: DNA
<213> ORGANISM: Artificial sequence
<220> FEATURE:
<223> OTHER INFORMATION: PCR primer 15R3

<400> SEQUENCE: 93
accagcgtgc ggttctcact 20

<210> SEQ ID NO 94
<211> LENGTH: 19
<212> TYPE: DNA
<213> ORGANISM: Artificial sequence
<220> FEATURE:
<223> OTHER INFORMATION: PCR primer 15F2

<400> SEQUENCE: 94
gccgcgacgt cacctacac 19

<210> SEQ ID NO 95
<211> LENGTH: 18
<212> TYPE: DNA
<213> ORGANISM: Artificial sequence
<220> FEATURE:
<223> OTHER INFORMATION: PCR primer 15R2

<400> SEQUENCE: 95
tcggccctgg gctcatct 18

<210> SEQ ID NO 96
<211> LENGTH: 20
<212> TYPE: DNA
<213> ORGANISM: Artificial sequence
<220> FEATURE:
<223> OTHER INFORMATION: PCR primer 15F1

<400> SEQUENCE: 96
gtcgccaggg caggacacag 20

<210> SEQ ID NO 97
<211> LENGTH: 21
<212> TYPE: DNA
<213> ORGANISM: Artificial sequence
<220> FEATURE:
<223> OTHER INFORMATION: PCR primer 15F1-1

<400> SEQUENCE: 97
acttggaggc ccacgttgac c 21

<210> SEQ ID NO 98
<211> LENGTH: 19
<212> TYPE: DNA
<213> ORGANISM: Artificial sequence
<220> FEATURE:
<223> OTHER INFORMATION: PCR primer 15R1-1

<400> SEQUENCE: 98
tgatgggcac caggcgctc 19

<210> SEQ ID NO 99
<211> LENGTH: 21
<212> TYPE: DNA
<213> ORGANISM: Artificial sequence
<220> FEATURE:
<223> OTHER INFORMATION: PCR primer 15F1-2

<400> SEQUENCE: 99
catccaggcc aatgtgacgg t 21

<210> SEQ ID NO 100
<211> LENGTH: 21
<212> TYPE: DNA
<213> ORGANISM: Artificial sequence
<220> FEATURE:
<223> OTHER INFORMATION: PCR primer 15R1-2

<400> SEQUENCE: 100
cctggtggca agctgggtgt t 21

<210> SEQ ID NO 101
<211> LENGTH: 20
<212> TYPE: DNA
<213> ORGANISM: Artificial sequence
<220> FEATURE:

<223> OTHER INFORMATION: PCR primer 16F

<400> SEQUENCE: 101
taaaactgga tggggctctc 20

<210> SEQ ID NO 102
<211> LENGTH: 18
<212> TYPE: DNA
<213> ORGANISM: Artificial sequence
<220> FEATURE:
<223> OTHER INFORMATION: PCR primer 16R

<400> SEQUENCE: 102
ggcctccacc agcactaa 18

<210> SEQ ID NO 103
<211> LENGTH: 20
<212> TYPE: DNA
<213> ORGANISM: Artificial sequence
<220> FEATURE:
<223> OTHER INFORMATION: PCR primer 17F

<400> SEQUENCE: 103
gggtccccca gtccttccag 20

<210> SEQ ID NO 104
<211> LENGTH: 17
<212> TYPE: DNA
<213> ORGANISM: Artificial sequence
<220> FEATURE:
<223> OTHER INFORMATION: PCR primer 17R

<400> SEQUENCE: 104
tccccagccc gcccaca 17

<210> SEQ ID NO 105
<211> LENGTH: 20
<212> TYPE: DNA
<213> ORGANISM: Artificial sequence
<220> FEATURE:
<223> OTHER INFORMATION: PCR primer 18F

<400> SEQUENCE: 105
gccccctcac caccccttct 20

<210> SEQ ID NO 106
<211> LENGTH: 18
<212> TYPE: DNA
<213> ORGANISM: Artificial sequence
<220> FEATURE:
<223> OTHER INFORMATION: PCR primer 18R

<400> SEQUENCE: 106
tcccgctgct ccccccac 18

<210> SEQ ID NO 107
<211> LENGTH: 18
<212> TYPE: DNA
<213> ORGANISM: Artificial sequence
<220> FEATURE:
<223> OTHER INFORMATION: PCR primer 19F

<400> SEQUENCE: 107
gatgccgtgg ggaccgtc 18

-continued

```
<210> SEQ ID NO 108
<211> LENGTH: 20
<212> TYPE: DNA
<213> ORGANISM: Artificial sequence
<220> FEATURE:
<223> OTHER INFORMATION: PCR primer 19R

<400> SEQUENCE: 108

gtgagcaggt ggcagtctcg                                                   20


<210> SEQ ID NO 109
<211> LENGTH: 21
<212> TYPE: DNA
<213> ORGANISM: Artificial sequence
<220> FEATURE:
<223> OTHER INFORMATION: PCR primer 20F

<400> SEQUENCE: 109

ccaccccctc tgctcgtagg t                                                 21


<210> SEQ ID NO 110
<211> LENGTH: 19
<212> TYPE: DNA
<213> ORGANISM: Artificial sequence
<220> FEATURE:
<223> OTHER INFORMATION: PCR primer 20R

<400> SEQUENCE: 110

ggtcccaagc acgcatgca                                                    19


<210> SEQ ID NO 111
<211> LENGTH: 22
<212> TYPE: DNA
<213> ORGANISM: Artificial sequence
<220> FEATURE:
<223> OTHER INFORMATION: PCR primer 21F

<400> SEQUENCE: 111

tgccggcctc ctgcgctgct ga                                                22


<210> SEQ ID NO 112
<211> LENGTH: 28
<212> TYPE: DNA
<213> ORGANISM: Artificial sequence
<220> FEATURE:
<223> OTHER INFORMATION: PCR primer TWR2-1

<400> SEQUENCE: 112

gtaggatggc cccacctgct caccctgc                                          28


<210> SEQ ID NO 113
<211> LENGTH: 20
<212> TYPE: DNA
<213> ORGANISM: Artificial sequence
<220> FEATURE:
<223> OTHER INFORMATION: PCR primer R27

<400> SEQUENCE: 113

aggtcaacgt gggcctccaa                                                   20
```

DETECTION AND TREATMENT OF POLYCYSTIC KIDNEY DISEASE

This application is a continuation application of U.S. application Ser. No. 11/485,062 filed Jul. 11, 2006, now pending; which is a continuation application of U.S. application Ser. No. 09/904,968 filed Jul. 13, 2001, now issued as U.S. Pat. No. 7,553,644; which claims the benefit under 35 USC §119(e) to U.S. Application Ser. No. 60/283,691 filed Apr. 13, 2001 and to U.S. Application Ser. No. 60/218,261 filed Jul. 13, 2000. The disclosure of each of the prior applications is considered part of and is incorporated by reference in the disclosure of this application.

This invention was made with government support under Grant Nos. DK48006, TW05393 and DK02562 awarded by the National Institutes of Health. The government has certain rights in the invention.

BACKGROUND OF THE INVENTION

Field of the Invention

The present invention relates generally to the diagnosis and treatment of polycystic kidney disease and more specifically to probes and agents useful in diagnosing and treating polycystic kidney disease and related disorders.

Background Information

Autosomal dominant polycystic kidney disease (ADPKD), also called adult-onset polycystic kidney disease, is one of the most common hereditary disorders in humans, affecting approximately one individual in a thousand. The prevalence in the United States is greater than 500,000, with 6,000 to 7,000 new cases detected yearly (Striker et al., Am. J. Nephrol. 6:161-164, 1986; Iglesias et al., Am. J. Kid. Dis. 2:630-639, 1983). The disease is considered to be a systemic disorder, characterized by cyst formation in the ductal organs such as kidney, liver, and pancreas, as well as by gastrointestinal, cardiovascular, and musculoskeletal abnormalities, including colonic diverticulitis, berry aneurysms, hernias, and mitral valve prolapse (Gabow et al., Adv. Nephrol. 18:19-32, 1989; Gabow, New Eng. J. Med. 329: 332-342, 1993).

The most prevalent and obvious symptom of ADPKD is the formation of kidney cysts, which result in grossly enlarged kidneys and a decrease in renal-concentrating ability. In approximately half of ADPKD patients, the disease progresses to end-stage renal disease, and ADPKD is responsible for 4-8% of the renal dialysis and transplantation cases in the United States and Europe (Proc. Eur. Dialysis and Transplant Assn., Robinson and Hawkins, eds., 17:20, 1981).

Few diagnostics are available for the identification and characterization of mutations of the PKD1 gene, which is located on human chromosome 16. A major factor contributing to the difficulty in identifying and characterizing mutations of the PKD1 gene is that greater than 70% of the length of the PKD1 gene is replicated on chromosome 16 and elsewhere, resulting in at least six PKD1 homologs. Significantly, the PKD1 homologs share a very high sequence identity with the PKD1 gene, including sequences having greater than 95% identity with the PKD1 gene. As such, oligonucleotides that have been examined for use as specific probes, or as primers for amplification, of PKD1 gene sequences have been found to cross-hybridize with the PKD1 homologs, and the inability to identify PKD1 locus specific probes has prevented accurate analysis of PKD1 gene mutations.

The identification and characterization of PKD1 gene mutations have been further hindered, in part, because transcription of the PKD1 gene results in production of a 14 kilobase (kb) mRNA, which is highly GC-rich. In addition, unlike the remainder of the PKD1 gene, which is extremely compact (approximately 13.5 kb mRNA coded within approximately 30 kb genomic DNA), exon 1 is separated from the rest of the gene by an intron of approximately 19 kb. Thus, previous investigators have simply placed the 5' anchor primer within the first intron and used it as a link to more 3' sequences. Exon 1 has several other features that have been major obstacles to its amplification, including an extremely high GC content (approximately 85%), and the ability to replicate with high fidelity in PKD1 gene homologs. Furthermore, no effective method for DNA based analysis of PKD1 gene exon 22, which is flanked on both ends by introns that contain lengthy polypyrimidine tracts. Accordingly, very few positions within the replicated segment and flanking exon 22 are suitable for the design of PKD1-specific primers.

A few oligonucleotides useful for examining regions of the human PKD1 gene, have been described. For example, the primer set forth below as SEQ ID NO:11 has been described in U.S. Pat. No. 6,017,717, and the primer set forth as SEQ ID NO:18 has been described by Watnick et al. (Hum. Mol. Genet. 6:1473-1481, 1997). Also, the primers set forth below as SEQ ID NOS:9, 10, 49 to 51, and 61 to 105 have been described by Watnick et al. (Am. J. Hum. Genet. 65:1561-1571, 1999). The primers set forth below as SEQ ID NOS: 9 and 10 and SEQ ID NOS: 11 and 12 also were more recently described by Phakdeekitcharoen et al. (Kidney International 58:1400-1412, 2000). In addition, a primer set forth as SEQ ID NO:13 in U.S. Pat. No. 6,071,717 has a nucleotide sequence that is substantially identical to that set forth below as SEQ ID NO:10, and a primer designated TWR2 by Watnick et al. (Mol. Cell 2:247-251, 1998) has a nucleotide sequence that is substantially identical to that set forth below as SEQ ID NO:12.

Despite the large number of families having diseases associated with PKD1 gene mutations, the potential clinical and scientific impact of mutation studies, and the availability of a genomic structure, the fact that only a relatively small number of PKD1 mutations have been described demonstrates the relative paucity of data due to the complicated genomic structure of the PKD1 gene. Thus, there exists a need for diagnostic methods suitable for examining the PKD1 gene and for identifying disorders related to PKD1 gene mutations. The present invention satisfies this need and provides additional advantages.

SUMMARY OF THE INVENTION

The present invention provides compositions and methods that allow for the selective examination of the human PKD1 gene, including the detection and identification of PKD1 gene mutations. For example, the compositions of the invention include oligonucleotide primers that are useful for selectively amplifying a region of a PKD1 gene, but not a corresponding region of a PKD1 homolog. Accordingly, the present invention relates to a PKD1 gene specific primer, which can be one of a primer pair. A primer of the invention includes a 5' region and adjacent PKD1-specific 3' region, wherein the 5' region has a nucleotide sequence that can hybridize to a PKD1 gene sequence and, optionally, to a PKD1 homolog sequence, and the 3' region has a nucleotide sequence that selectively hybridizes only to a PKD1 gene sequence, and particularly not to a PKD1 gene homolog sequence, except that a primer of the invention does not have a sequence as set forth in SEQ ID NO:11, SEQ ID NO:18, SEQ ID NO:52, or SEQ ID NO:60. A 5' region of a primer of the invention generally contains at least about ten contiguous nucleotides, and the 3' region contains at least one 3' terminal nucleotide, wherein the at least one 3' terminal nucleotide is identical to a nucleotide that is 5' and adjacent to the nucleotide sequence of the PKD1 gene to which the 5' region of the primer can hybridize, and is different from a nucleotide that is 5' and adjacent to a nucleotide sequence of the PKD1 homolog to which the 5' region of the primer can hybridize. Generally, the primer includes a 5' region of about 14 to 18 nucleotides and a 3' region of about 2 to 6 nucleotides, particularly about 2 to 4 nucleotides. For example, a primer of the invention can have a sequence as set forth in any of SEQ ID NOS:3 to 10, 12 to 17, 19 to 51 and 61 to 113.

The present invention also relates to an isolated mutant PKD1 polynucleotide, or an oligonucleotide portion thereof. The polynucleotides of the invention are exemplified by mutation of SEQ ID NO:1, which appear to be normal variants that are not associated with a PKD1-associated disorder, for example, a polynucleotide or oligonucleotide that includes nucleotide 474, wherein nucleotide 474 is a T; nucleotide 487, wherein nucleotide 487 is an A; nucleotide 9367, wherein nucleotide 9367 is a T; nucleotide 10143, wherein nucleotide 10143 is a G; nucleotide 10234, wherein nucleotide 10234 is a C; nucleotide 10255, wherein nucleotide 10255 is a T; or a combination thereof; and by mutations of SEQ ID NO:1 that are associated with a PKD1-associated disorder, for example, a polynucleotide or oligonucleotide that includes nucleotide 3110 of SEQ ID NO:1, wherein nucleotide 3110 is a C; nucleotide 8298 of SEQ ID NO:1, wherein nucleotide 8298 is a G; nucleotide 9164 of SEQ ID NO:1, wherein nucleotide 9164 is a G; nucleotide 9213 of SEQ ID NO:1, wherein nucleotide 9213 is an A; nucleotide 9326 of SEQ ID NO:1, wherein nucleotide 9326 is a T; nucleotide 10064 of SEQ ID NO:1, wherein nucleotide 10064 is an A; or a combination thereof. The invention also provides a vector containing such a polynucleotide, or an oligonucleotide portion thereof, and provides a host cell containing such a polynucleotide or oligonucleotide, or vector.

A PKD1-specific primer of the invention is exemplified by an oligonucleotide that can selectively hybridize to a nucleotide sequence that flanks and is within about fifty nucleotides of a nucleotide sequence selected from about nucleotides 2043 to 4209; nucleotides 17907 to 22489; nucleotides 22218 to 26363; nucleotides 26246 to 30615; nucleotides 30606 to 33957; nucleotides 36819 to 37140; nucleotides 37329 to 41258; and nucleotides 41508 to 47320 of SEQ ID NO:1. The primer, which can be one of a primer pair, can have a nucleotide sequence substantially identical to any of SEQ ID NOS: 3 to 18, provided that when the primer is not one of a primer pair, the primer does not have a sequence as set forth in SEQ ID NO:11, SEQ ID NO:18, SEQ ID NO:52, or SEQ ID NO:60. Accordingly, the present invention further relates to a primer pair that can amplify a portion of a PKD1 gene, for example, the wild type PKD1 gene set forth as SEQ ID NO:1, wherein the amplification product can include about nucleotides 2043 to 4209; nucleotides 17907 to 22489; nucleotides 22218 to 26363; nucleotides 26246 to 30615; nucleotides 30606 to 33957; nucleotides 36819 to 37140; nucleotides 37329 to 41258; nucleotides 41508 to 47320; or a combination thereof. A primer pair of the invention is useful for performing PKD1-specific amplification of a portion of a PKD1 gene.

Primer pairs of the invention are exemplified by a pair including at least one forward primer and at least one reverse primer of the oligonucleotides sequences set forth in SEQ ID NOS:3 to 18 or a sequence substantially identical thereto. In one embodiment, the primer pair includes SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; or SEQ ID NOS:9 and 113. Also provided are primer pairs useful for performing nested amplification of a PKD1-specific amplification product of a PKD1 gene, for example, the primer pairs set forth as SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS: 51 and 61; SEQ ID NOS:62 and 63; SEQ ID NOS:64 and 65; SEQ ID NOS:66 and 67; SEQ ID NOS:68 and 69; SEQ ID NOS:70 and 71; SEQ ID NOS:72 and 73; SEQ ID NOS:74 and 75; SEQ ID NOS:76 and 77; SEQ ID NOS:78 and 79; SEQ ID NOS:80 and 81; SEQ ID NOS:82 and 83; SEQ ID NOS:84 and 85; SEQ ID NOS:86 and 87; SEQ ID NOS:88 and 89; SEQ ID NOS:90 and 91; SEQ ID NOS:92 and 93; SEQ ID NOS:94 and 95; SEQ ID NOS:96 and 113; SEQ ID NOS:97 and 98; SEQ ID NOS:99 and 100; SEQ ID NOS:101 and 102; SEQ ID NOS:103 and 104; SEQ ID NOS: 105 and 106; SEQ ID NOS:107 and 108; SEQ ID NOS:109 and 110; or SEQ ID NOS:111 and 112. In another embodiment, the invention relates to a plurality of primer pairs, which can include two or more primer pairs that are useful for generating two or more PKD1-specific amplification products of a PKD1 gene; or can include two or more primer pairs that are useful for generating a PKD1-specific amplification product of a PKD1 gene and for generating a nested amplification product of the PKD1-specific amplification product.

The present invention also relates to a purified mutant PKD1 polypeptide, or a peptide portion thereof, comprising an amino acid sequence of a mutant of SEQ ID NO:2. A mutant PKD1 polypeptide, or peptide portion thereof can be substantially identical to a sequence of SEQ ID NO:2 and, for example, include amino acid residue 88 of SEQ ID NO:2, wherein residue 88 is a V; residue 967 of SEQ ID NO:2, wherein residue 967 is an R; residue 2696 of SEQ ID NO:2, wherein residue 2696 is an R; residue 2985 of SEQ ID NO:2, wherein residue 2985 is a G; residue 3039 of SEQ ID NO:2, wherein residue 3039 is a C; residue 3285 of SEQ ID NO:2, wherein residue 3285 is an I; or residue 3311 of SEQ ID NO:2, wherein residue 3311 is an R; or can include residue 3000 of a truncated mutant PKD1 polypeptide ending at amino acid residue 3000 with respect to SEQ ID NO:2, wherein residue 3001 is absent (and the mutant PKD1 polypeptide is truncated) due to the presence of a STOP codon in the encoding mutant PKD1 polynucleotide; or a combination of such mutations. Also provided is a purified antibody that specifically binds to a mutant PKD1 polypeptide, or to a peptide thereof.

The present invention further relates to a primer or an oligonucleotide of the invention immobilized to a solid support. In addition, the primer or oligonucleotide can be one of a plurality of primers, oligonucleotides, or a combination thereof, each of which is immobilized to a solid support. The solid support can be any support, including, for example, a microchip, in which case, the primers, oligonucleotides, or combination thereof can be arranged in array, particularly an addressable array. The primers, oligonucleotides, or combination thereof also can be degenerate with respect to each other, and specific for a wild type PKD1 polynucleotide, a mutant PKD1 polynucleotide, including a variant, or combinations thereof, and, therefore, provide a means for multiplex analysis. Accordingly, the present invention provides compositions comprising one or a plurality of immobilized primers or oligonucleotides of the invention, or combinations thereof.

The present invention also relates to a method of detecting a PKD1 polynucleotide in a sample, wherein the PKD1 polynucleotide is a wild type PKD1 polynucleotide having a sequence as set forth in SEQ ID NO:1, or a mutant PKD1 polynucleotide, which can be a variant PKD1 polynucleotide that has a sequence different from SEQ ID NO:1 but is not associated with a PKD1-associated disorder or can be a mutant PKD1 polynucleotide that is associated with a PKD1-associated disorder. A method of the invention can be performed, for example, by contacting nucleic acid molecules in a sample suspected of containing a PKD1 polynucleotide with at least one primer pair under conditions suitable for amplification of a PKD1 polynucleotide by the primer pair; and generating a PKD1-specific amplification product under said conditions, thereby detecting a PKD1 polynucleotide in the sample. The primer pair can be any primer pair as disclosed herein, for example, a primer pair such as SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; or SEQ ID NOS:9 and 113; or can be a combination of such primer pairs.

A method of detecting a PKD1 polynucleotide can further include, upon generating a PKD1-specific amplification product, contacting the amplification product with at least a second primer pair, under conditions suitable for nested amplification of the PKD1-specific amplification product by the second primer pair, and generating a nested amplification product. The second primer pair can be any primer pair that can produce a nested amplification product of the PKD1-specific amplification product, for example, a second primer pair such as SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; primer pairs formed using consecutive primers set forth in Table 2 as SEQ ID NOS:62 to 96, 113, and 97 to 112; or a combination thereof.

Upon detecting a PKD1 polynucleotide in a sample according to a method of the invention, an additional step of detecting the presence or absence of a mutation in an amplification product of the PKD1 polynucleotide in the sample as compared to a corresponding nucleotide sequence in SEQ ID NO:1. As such, a method of the invention provides a means to identify a PKD1 polynucleotide in a sample as a mutant PKD1 polynucleotide or a wild type PKD1 polynucleotide, wherein detecting the absence of a mutation in the amplification product identifies the PKD1 polynucleotide in the sample as a wild type PKD1 polynucleotide, and wherein detecting the presence of a mutation in the amplification product identifies the PKD1 polynucleotide in the sample as a mutant PKD1 polynucleotide, which can be a variant PKD1 polynucleotide, or can be mutant PKD1 polynucleotide associated with a PKD1-associated disorder, the latter of which are exemplified by a polynucleotide that is substantially identical to SEQ ID NO:1, and wherein at least nucleotide 474 is a T; nucleotide 487 is an A; nucleotide 3110 is a C; nucleotide 8298 is a G; nucleotide 9164 is a G; nucleotide 9213 is an A; nucleotide 9326 is a T; nucleotide 9367 is a T; nucleotide 10064 is an A; nucleotide 10143 is a G; nucleotide 10234 is a C; or nucleotide 10255 is a T.

The presence or absence of a mutation in an amplification product generated according to a method of the invention can be detected any method useful for detecting a mutation. For example, the nucleotide sequence of the amplification product can be determined, and can be compared to the corresponding nucleotide sequence of SEQ ID NO:1. The melting temperature of the amplification product also can be determined, and can be compared to the melting temperature of a corresponding double stranded nucleotide sequence of SEQ ID NO:1. The melting temperature can be determined using a method such as denaturing high performance liquid chromatography.

An advantage of a method of the invention is that a large number of samples can be examined serially or in parallel. Accordingly, a method of the invention can be performed with respect to a plurality of samples, and can be performed using a high throughput format, for example, by organizing the samples of a plurality of samples in an array such as in an array is on a microchip. The method can further include detecting the presence or absence of a mutation in an amplification product of the samples of the plurality of samples, for example, by determining the melting temperature of the amplification product and comparing it to the melting temperature of a corresponding nucleotide sequence of SEQ ID NO:1 using a method such as denaturing high performance liquid chromatography, or the presence or absence of a mutation can be performed using any method useful for such a purpose, for example, matrix-assisted laser desorption time of flight mass spectrometry or high throughput conformation-sensitive gel electrophoresis, each of which is readily adaptable to a high throughput analysis foimat.

In another embodiment, the presence or absence of a mutation in an amplification product can be detected by contacting the amplification product with the oligonucleotide of the invention, under condition suitable for selective hybridization of the oligonucleotide to an identical nucleotide sequence; and detecting the presence or absence of selective hybridization of the oligonucleotide to the amplification product. Using such a method detecting the presence of selective hybridization identifies the PKD1 polynucleotide in the sample as a mutant PKD1 polynucleotide, and detecting the absence of selective hybridization identifies the PKD1 polynucleotide as a wild type PKD1 polynucleotide. Where an absence of a mutation is detected, the PKD1 polynucleotide in the sample is identified as a wild type PKD1 polynucleotide. In comparison, where the presence of a mutation is identified, the mutant PKD1 polynucleotide so identified can be further examined to determine whether the mutant PKD1 polynucleotide is a variant PKD1 polynucleotide, which is associated with a normal phenotype with respect to PKD1, for example, where the amplification product has a nucleotide sequence substantially identical to SEQ ID NO:1, and including C474T, G487A, G4885A; C6058T; G6195A; T7376C; C7696T; G8021A; C9367T, A10143G, T10234C, or a combination thereof, or is a mutant PKD1 polynucleotide associated with a PKD1-associated disorder, for example, where the amplification product has a nucleotide sequence substantially identical to SEQ ID NO:1, and including T3110C, G3707A; T6078A;

C7433T; T8298G; A9164G; G9213A, C9326T; G10064A; an insertion of GCG between nucleotides G7535 and A7536; or a combination thereof, each of which is associated with ADPKD (see Example 2; see, also, Phakdeekitcharoen et al., Kidney International 58:1400-1412, 2000, which is incorporated herein by reference).

The present invention further relates to a method of detecting the presence of a mutant PKD1 polynucleotide in a sample. In one embodiment, a method of the invention is performed by amplifying a nucleic acid sequence in a sample suspected of containing a mutant PKD1 polynucleotide using a primer pair of the invention, for example, a primer pair selected from SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; or SEQ ID NOS:9 and 113, thereby obtaining a PKD1-specific amplification product of a PKD1 gene sequence; and detecting a mutant PKD1 polynucleotide in the amplification product. The mutant PKD1 nucleotide in the amplification product can be detected using any method useful for detecting a mutation in a polynucleotide, for example, using denaturing high performance liquid chromatograph. In another embodiment, a method of the invention is performed by contacting a sample suspected of containing a mutant PKD1 polynucleotide with a probe comprising an isolated polynucleotide of the invention, or an oligonucleotide portion thereof, under conditions such that the probe selectively hybridizes to a mutant PKD1 polynucleotide, and detecting specific hybridization of the probe and a PKD1 polynucleotide, thereby detecting the presence of a mutant PKD1 polynucleotide sequence in the sample.

The present invention further relates to a method of identifying a subject having or is at risk of having a PKD1-associated disorder. Such a method can be performed, for example, by contacting nucleic acid molecules in a sample from a subject with at least one primer pair of the invention under conditions suitable for amplification of a PKD1 polynucleotide by the primer pair, thereby generating an amplification product; and testing an amplification product for the presence or absence of a mutation indicative of a PKD1-associated disorder. As disclosed herein, the absence of such a mutation identifies the subject as not having or at risk of the having a PKD1-associated disorder, wherein the presence of such a mutation identifies the subject as having or is at risk of having a PKD1-associated disorder, for example, ADPKD or acquired cystic disease.

A primer pair useful in a diagnostic method of the invention can include at least one primer pair selected from SEQ ID NO:3 and 4; SEQ ID NO:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; and SEQ ID NOS:9 and 113. The subject can be any subject having a PKD1 gene and susceptible to a PKD1-associated disorder, including a vertebrate subject, and particularly a mammalian subject such as a cat or a human. In addition, the diagnostic method can be performed in a high throughput format, thereby allowing the examination of a large number samples in a cost-effective manner.

The diagnostic method can further include contacting the amplification product generated as described above with at least a second primer pair, under conditions suitable for nested amplification of the amplification product by a second primer pair, thereby generating a nested amplification product. The second primer pair can be, for example, a primer pair selected from SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; a primer pair formed using two consecutive primers set forth in Table 2 as SEQ ID NOS:62 to 96, 113, and 97 to 112 (i.e., SEQ ID NOS: 62 and 63, SEQ ID NOS:64 and 65, and so on); and a combination thereof, in which case, the step of testing the amplification product for the presence or absence of a mutation comprises testing the nested amplification product. It should be recognized that the selection of a primer pair for nested amplification is based, in part, on the sequence of the PKD1-specific amplification product that is to be used as a template for the nested amplification, i.e., nested primer pairs are selected such that they can hybridize to a target PKD1-specific amplification product and can amplify the target sequence.

An amplification product can be tested for the presence or absence of the mutation, for example, by determining the nucleotide sequence of the amplification product, and comparing it to a corresponding nucleotide sequence of SEQ ID NO:1; by determining the melting temperature of the amplification product, and comparing it to the melting temperature of a corresponding nucleotide sequence of SEQ ID NO:1, for example, using a method such as denaturing high performance liquid chromatography; or by contacting the amplification product with an oligonucleotide probe containing nucleotide 474 of SEQ ID NO:1, wherein nucleotide 474 is a T; nucleotide 487 of SEQ ID NO:1, wherein nucleotide 487 is an A; nucleotide 3110 of SEQ ID NO:1, wherein nucleotide 3110 is a C; nucleotide 8298 of SEQ ID NO:1, wherein nucleotide 8298 is a G; nucleotide 9164 of SEQ ID NO:1, wherein nucleotide 9164 is a G; nucleotide 9213 of SEQ ID NO:1, wherein nucleotide 9213 is an A; nucleotide 9326 of SEQ ID NO:1, wherein nucleotide 9326 is a T; nucleotide 9367 of SEQ ID NO:1, wherein nucleotide 9367 is a T; nucleotide 10064 of SEQ ID NO:1, wherein nucleotide 10064 is an A; nucleotide 10143 of SEQ ID NO:1, wherein nucleotide 10143 is a G; nucleotide 10234 of SEQ ID NO:1, wherein nucleotide 10234 is a C; and nucleotide 10255 of SEQ ID NO:1, wherein nucleotide 10255 is a T, under conditions suitable for selective hybridization of the probe to a mutant PKD1 polypeptide, which can be a normal variant or can be a mutant PKD1 polynucleotide associated with a PKD1-associated disorder.

The present invention also relates to a method of diagnosing a PKD1-associated disorder in a subject suspected of having a PKD1-associated disorder. Such a method is performed by amplifying a nucleic acid sequence in a sample obtained from the subject using a primer pair suitable for PKD1-specific amplification of a PKD1 gene sequence, for example, a primer pair such as SEQ ID NO:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18, or SEQ ID NOS:9 and 113, thereby obtaining a PKD1-specific first amplification product; and detecting a mutation of a PKD1 gene sequence in the PKD1-specific first amplification product, wherein the mutation is indicative of a PKD1-associated disorder, thereby diagnosing a PKD1-associated disorder in the subject.

In one embodiment, the diagnostic method includes a step of further amplifying the first amplification product using a second set of primer pairs to obtain a nested amplification product; and detecting a PKD1 gene mutation in the nested amplification product. The second set of primer pairs can be any primer pairs useful for amplifying the PKD1-specific first amplification product, including, for example, the primer pairs exemplified by SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; or any of the primer pairs formed using consecutive primers set forth in Table 2 as SEQ ID NOS:62 to 96, 113, and 97 to 112.

In another method, the diagnostic method includes a step of contacting the PKD1-specific first amplification product or second amplification product with a probe comprising an isolated polynucleotide, or an oligonucleotide portion thereof, comprising a mutant of SEQ ID NO:1, under conditions such that the probe can selectively hybridize to a mutant PKD1 polynucleotide; and detecting selective hybridization of the probe to the first amplification product, thereby diagnosing a PKD1-associated disorder in the subject. The probe can be, for example, an oligonucleotide portion of SEQ ID NO:1 that includes one or more of nucleotide 474 is a T; nucleotide 487 is an A; nucleotide 3110 is a C; nucleotide 8298 is a G; nucleotide 9164 is a G; nucleotide 9213 is an A; nucleotide 9326 is a T; nucleotide 9367 is a T; nucleotide 10064 is an A; nucleotide 10143 is a G; nucleotide 10234 is a C; or nucleotide 10255 is a T.

The present invention also relates to a method of detecting the presence of a mutant PKD1 polypeptide in a sample. Such a method can be performed, for example, by contacting a sample suspected of containing a mutant PKD1 polypeptide with an antibody that specifically binds to a mutant PKD1 polypeptide, under conditions which allow the antibody to bind to the mutant PKD1 polypeptide and detecting specific binding of the antibody and the mutant PKD1 polypeptide in the sample. The detection of an immunocomplex of the antibody and a mutant PKD1 polypeptide, for example, indicates the presence of a mutant PKD1 polypeptide in the sample. In one embodiment, the method is performed by contacting a tissue sample from a subject suspected of containing a PKD1 polypeptide with the antibody that specifically binds a mutant PKD1 polypeptide under conditions that allow the antibody interact with a PKD1 polypeptide and detecting specific binding of the antibody and the PKD1 polypeptide in the tissue.

The present invention further relates to a kit for detecting a mutant PKD1 polynucleotide, which can be a variant PKD1 polynucleotide or a mutant PKD1 polynucleotide associated with a PKD1-associated disorder. The kit can contain, for example, a carrier means containing therein one or more containers wherein a first container contains a nucleotide sequence useful for detecting a wild type or mutant PKD1 polynucleotide. As such, a nucleotide sequence useful in a kit of the invention can be an oligonucleotide comprising at least ten contiguous nucleotides of SEQ ID NO:1, including at least one of nucleotide 474, wherein nucleotide 474 is a T; nucleotide 487, wherein nucleotide 487 is an A; nucleotide 3110, wherein nucleotide 3110 is a C; a position corresponding to nucleotide 3336, wherein nucleotide 3336 is deleted; nucleotide 3707, wherein nucleotide 3707 is an A; nucleotide 4168, wherein nucleotide 4168 is a T; nucleotide 4885, wherein nucleotide 4885 is an A; nucleotide 5168, wherein nucleotide 5168 is a T; nucleotide 6058, wherein nucleotide 6058 is a T; nucleotide 6078, wherein nucleotide 6078 is an A; nucleotide 6089, wherein nucleotide 6089 is a T; nucleotide 6195, wherein nucleotide 6195 is an A; nucleotide 6326, wherein nucleotide 6326 is a T; a position corresponding to nucleotides 7205 to 7211, wherein nucleotides 7205 to 7211 are deleted; nucleotide 7376, wherein nucleotide 7376 is a C; a nucleotide sequence corresponding to nucleotides 7535 to 7536, wherein a GCG nucleotide sequence is inserted between nucleotides 7535 and 7536; nucleotide 7415, wherein nucleotide 7415 is a T; nucleotide 7433, wherein nucleotide 7433 is a T; nucleotide 7696, wherein nucleotide 7696 is a T; nucleotide 7883, wherein nucleotide 7883 is a T; nucleotide 8021, wherein nucleotide 8021 is an A; a nucleotide sequence corresponding to nucleotide 8159 to 8160, wherein nucleotides 8159 to 8160 are deleted; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T. A nucleotide sequence useful in a kit of the invention also can comprise one or both primers of a primer pair, particularly at least a forward primer and a reverse primer as set forth in SEQ ID NOS: 3 to 18; and the kit can further include at least a second primer pair, including a forward and reverse primer as set forth in SEQ ID NOS: 19 to 51 and 61 to 113. In another aspect, the present invention relates to a kit containing an antibody that specifically binds to a mutant PKD1 polypeptide or peptide portion thereof.

DETAILED DESCRIPTION OF THE INVENTION

The present invention provides compositions and methods for identifying polycystic kidney disease-associated protein-1 (PKD1) gene variants and mutants, and for diagnosing PKD1-associated disorders in a subject. Prior to the present disclosure, the ability to selectively examine the entire PKD1 gene for mutations was precluded due to the high sequence homology of the PKD1 gene and the PKD1 gene homologs, including those present with the PKD1 gene on human chromosome 16. As disclosed herein, polynucleotide sequences have now been developed that are useful as probes and primers for examining the entire PKD1 gene. Accordingly, the present invention provides polynucleotides, and oligonucleotide portions thereof, of a PKD1 gene and of PKD1 gene mutants that are useful for detecting PKD1 mutations, and that can be diagnostic of a PKD1-associated disorder.

Autosomal dominant polycystic kidney disease (ADPKD) exhibits a transmission pattern typical of autosomal dominant inheritance, where typically each offspring of an affected individual has a 50% chance of inheriting the causative gene. Linkage studies indicated that a causative gene is present on the short arm of chromosome 16, near the I globin cluster; this locus was designated PKD1 (Reeders et al., Nature, 317:542, 1985.) Though other PKD-associated genes exist (for example, PKD2), defects in PKD1 appear to cause ADPKD in about 85-90% of affected families (Parfrey et al., New Eng. J. Med. 323:1085-1090, 1990; Peters et al., Contrib. Nephrol. 97:128-139, 1992).

The PKD1 gene has been localized to chromosomal position 16p13.3, specifically to an interval of approximately 600 kb between the markers ATPL and CMM65 (D16S84). This region is rich in CpG islands that often flank transcribed sequences; it has been estimated that this interval contains at least 20 genes. The precise location of the PKD1 gene was pinpointed by the finding of an ADPKD family whose affected members carry a translocation that disrupts a 14 kb RNA transcript associated with this region (European PKD Consortium, Cell, 77:881, 1994).

Figure 1:
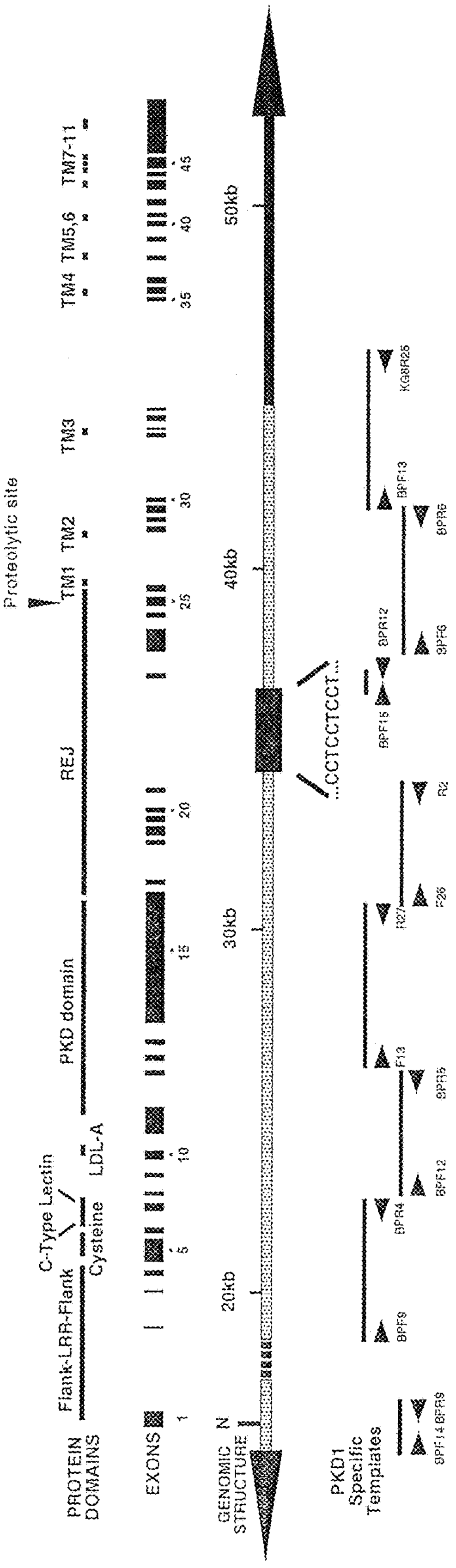
FIG. 1 is a schematic showing the genomic structure of the PKD1 gene (SEQ ID NO:1) and the relative position of locus-specific templates and primers.

The genomic structure of the PKD1 gene, which is illustrated in FIG. 1 (SEQ ID NO:1; see Appendix A; see, also, GenBank Accession No. L39891, which is incorporated herein by reference), extends over approximately 50 kb, contains 46 exons, and is bisected by two large polypyrimidine tracts of approximately 2.5 kb and 0.5 kb, respectively, in introns 21 and 22 (indicated by " . . . CCTCC TCCT . . . " in FIG. 1). The replicated portion of the gene, which begins prior to the 5'UTR and is believed to end in exon 34 (FIG. 1; stippled region), covers approximately two thirds of the 5' end of the gene and is duplicated several times in a highly similar, transcribed fashion elsewhere in the human genome (Germino et al., Genomics 13:144-151, 1992; European Chromosome 16 Tuberous Sclerosis Consortium, 1993, Cell 75:1305-1315). The encoded PKD1 polypeptide is shown as SEQ ID NO:2 (see Appendix A; see, also, GenBank Accession No. P98161, which is incorporated herein by reference). It should be recognized that SEQ ID NO:2 is not the same amino acid sequence as that shown to be encoded by GenBank Accession No. L39891 (see, also, GenBank AAB59488), presumably due to errors in predicting the encoded PKD1 polypeptide from the PKD1 gene sequence. Instead, the wild type PKD1 polypeptide sequence is shown in SEQ ID NO:2 (GenBank Accession No. P98161).

The present invention provides a PKD1 gene specific primer, which can be one of a primer pair. A primer of the invention includes a 5' region and adjacent PKD1-specific 3' region, wherein the 5' region has a nucleotide sequence that can hybridize to a PKD1 gene sequence or to a PKD1 gene sequence and a PKD1 gene homolog sequence, and the 3' region has a nucleotide sequence that selectively hybridizes only to a PKD1 gene sequence, and particularly not to a PKD1 gene homolog sequence, except that a primer of the invention does not have a sequence as set forth in SEQ ID NO:11, SEQ ID NO:18, SEQ ID NO:52, or SEQ ID NO:60. Thus, a primer of the invention can have a sequence as set forth in any of SEQ ID NOS:3, 4, 5, 6, 7, 8, 9, 10, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112 and 113, as well as a sequence that is substantially identical to any of SEQ ID NOS:3 to 51 and 61 to 113, provided the sequence comprises a 5' region that can hybridize to a PKD1 gene sequence or to a PKD1 gene sequence and a PKD1 gene homolog sequence, and a 3' region that selectively hybridizes to a PKD1 gene sequence, but not to a PKD1 gene homolog sequence; and provided the sequence is not otherwise specifically excluded herein.

As disclosed herein, a primer of the invention can be prepared by aligning SEQ ID NO:1 with the PKD1 gene homologs contained in GenBank Accession Nos. AC002039, AC010488, AC040158, AF320593 and AF320594 (each of which is incorporated herein by reference; see, also, Bogdanova et al., Genomics 74:333-341, 2001, which is incorporated herein by reference) and identifying regions having potential sequence differences, then selecting as PKD1-specific primers those sequences that match over at least about ten nucleotides and that have a mismatch at or adjacent to the 3' terminus of the matched regions (see Example 1; see, also, Phakdeekitcharoen et al., supra, 2000). Such primers are referred to as "PKD1-specific primers" because, while they can hybridize to a PKD1 gene and a PKD1 gene homologue, an extension product only can be generated upon hybridization to a PKD1 gene due to the mismatch of one or more nucleotides in the 3' region when the primer hybridizes to a PKD1 gene homologue. Confirmation that a selected oligonucleotide is a PKD1-specific primer can be made using methods as disclosed herein (Example 1) or otherwise known in the art. For example, a simple and straightforward method for determining that a primer is a PKD1-specific primer of the invention is to perform a primer extension or an amplification reaction using the putative PKD1-specific primer and templates including a PKD1 gene sequence and PKD1 gene homolog sequences, and detecting a single extension product or amplification product generated from the PKD1 gene template, but not the PKD1 gene homolog templates. Sequences identified as PKD1-specific primers using this or another method can be confirmed by performing various control experiments as described by Watnick et al. (supra, 1999), for example, by comparing an amplification product obtained in a cell having a PKD1 gene with the products, if any, produced using the radiation hybrid cell line, 145.19, which lacks the PKD1 gene but contains PKD1 gene homologs.

A nucleotide sequence suspected of being useful as a PKD1-specific primer also can be compared against a human genomic DNA database using, for example, a BLAST search or other algorithm, to confirm that the nucleotide sequence meets the requirements of a PKD1-specific primer as defined herein. For example, a putative PKD1-specific primer can be examined at the National Center for Biotechnology Information (NCBI), which can be accessed on the world wide web, by selecting the "Blast" option, thereafter selecting the "Search for short nearly exact matches," entering in the sequence to be examined, and, using the default search algorithms (word size 7), searching the "nr" database, which include all non-redundant GenBank+EMBL+DDBJ+PDB sequences, but no EST, SST, GSS or HTGS sequences; output can be restricted to showing only the top ten matches.

In a PKD1-specific primer of the invention, the 5' region contains at least about ten contiguous nucleotides, generally at least about 12 nucleotides, and usually about 14 to 18 nucleotides. In addition, the 3' region of the primer contains at least one 3' terminal nucleotide, and can include a sequence of at least about 2 to 6 nucleotides, particularly about 2 to 4 nucleotides. Where the 3' region consists of a single 3' terminal nucleotide, the primer is selected such that the 3' terminal nucleotide is identical to a nucleotide that is 5' and adjacent to the nucleotide sequence of the PKD1 gene to which the 5' region of the primer can hybridize, and is different from a nucleotide that is 5' and adjacent to a nucleotide sequence of the PKD1 homolog to which the 5' region of the primer can hybridize, i.e., provides a mismatched nucleotide. Where the 3' region of the PKD1-specific primer contains two or more nucleotides, one or more of the nucleotides can be mismatched, and the mismatched nucleotide can, but need not include the 3' terminal nucleotide, provided that when the mismatched nucleotide or nucleotides do not include the 3' terminal nucleotide, the primer cannot be extended when hybridized to a PKD1 gene homolog.

PKD1-specific primers of the invention are exemplified by primers that can selectively hybridize to a nucleotide sequence that flanks and is within about fifty nucleotides of a nucleotide sequence of SEQ ID NO:1 selected from about nucleotides 2043 to 4209; nucleotides 17907 to 22489; nucleotides 22218 to 26363; nucleotides 26246 to 30615; nucleotides 30606 to 33957; nucleotides 36819 to 37140; nucleotides 37329 to 41258; and nucleotides 41508 to 47320. A primer of the invention is exemplified by any of SEQ ID NOS: 3 to 10, 12 to 17, 19 to 51, and 61 to 113, and can have a sequence substantially identical to any of SEQ ID NOS:3 to 51 and 61 to 113, provided the sequence meets the requirements of a PKD1-specific primer as disclosed herein, and provided the sequence is not a sequence as set forth in any of SEQ ID NO:11, SEQ ID NO:18, SEQ ID NO:52, and SEQ ID NO:60.

A primer is considered to be "substantially identical" to any of SEQ ID NOS:3 to 51 and 61 to 113 if the primer has at least about 80% or 85%, generally at least about 90%, usually at least about 95%, and particularly at least about 99% sequence identity with one of SEQ ID NOS:3 to 51 and 61 to 113, and has a 5' region and adjacent PKD1-specific 3' region, wherein the 5' region has a nucleotide sequence that can hybridize to a PKD1 gene sequence or to a PKD1 gene sequence and a PKD1 gene homolog sequence, and the 3' region has a nucleotide sequence that selectively hybridizes only to a PKD1 gene sequence, and particularly not to a PKD1 gene homolog sequence, as defined herein, except that a primer of the invention does not have a sequence as set forth in SEQ ID NO:11, SEQ ID NO:18, SEQ ID NO:52, or SEQ ID NO:60. As such, a primer of the invention can include one or a few, but no more than about four or five, more or fewer nucleotide than a primer as set forth in SEQ ID NOS:3 to 51 and 61 to 113, provided the primer meets the functional requirements as defined herein.

The present invention also provides primer pairs. In one embodiment, a primer pair of the invention comprising a forward and reverse PKD1-specific primer as disclosed herein. As such, a primer pair of the invention can amplify a portion of SEQ ID NO:1 including about nucleotides 2043 to 4209; nucleotides 17907 to 22489; nucleotides 22218 to 26363; nucleotides 26246 to 30615; nucleotides 30606 to 33957; nucleotides 36819 to 37140; nucleotides 37329 to 41258; nucleotides 41508 to 47320; or a combination thereof. In general, a primer pair of the invention can produce an amplification product of about ten kilobases or shorter, generally about 7500 bases or shorter, and particularly about six kilobases or shorter. Primer pairs of the invention are exemplified by a forward primer and a reverse primer selected from SEQ ID NOS:3 to 18, for example, by any of SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; and SEQ ID NOS:9 and 113, which can be used to produce PKD1-specific amplification products of about 0.3 kilobases to about 5.8 kilobases.

As disclosed herein, a set of eight polymerase chain reaction (PCR) primer pairs can be used to prepare PKD1-specific amplification products that encompass all of the exons and their flanking introns within the replicated region of the PKD1 gene. In view of the disclosed nucleotide sequences of the primers and of SEQ ID NO:1, it will be recognized that additional PCR primer pairs useful for a preparing PKD1-specific first amplification product can be based on the exemplified primers and primer pairs, but can include one or few additional nucleotides (based on SEQ ID NO:1) at one or both ends of the exemplified primers, or can have one or a few nucleotides of an exemplified primer deleted, and their usefulness can be determined by comparing an amplification product generated using the derived or modified primer with a PKD1-specific amplification product as disclosed herein. As such, a primer pair based, for example, on SEQ ID NOS: 3 and 4 can be used to generate a PKD-1 specific amplification product containing about nucleotides 2043 to 4209 of SEQ ID NO:2, where in reference to "about" nucleotides 2043 to 4209 of SEQ ID NO:2 accounts for the disclosure that a primer pair used for amplification can be identical or substantially identical to SEQ ID NOS: 3 and 4.

Accordingly, the present invention provides primer pairs comprising a forward primer and a reverse primer having nucleotide sequences as set forth in SEQ ID NOS:3 to 18; primer pairs exemplified by SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; and SEQ ID NOS:9 and 113; and substantially identical primer pairs that comprise primers based on or derived from the exemplified primers, such primer pairs being useful for preparing a PKD1-specific amplification product. The primer pairs shown as SEQ ID NOS: 9 and 10 and SEQ ID NOS: 11 and 12 have been described by Phakdeekitcharoen et al. (supra, 2000), as have the PKD1 specific amplification products generated using these primers.

It should be recognized that certain primers and certain primer pairs exemplified herein are not considered to be encompassed within the present invention. For example, the primer set forth in SEQ ID NO:11 has been described in U.S. Pat. No. 6,017,717 (which is incorporated herein by reference; column 24, SEQ ID NO:15); and the primer set forth in SEQ ID NO:18 has been described by Watnick et al. (Hum. Mol. Genet. 6:1473-1481, 1997, which is incorporated herein by reference; see page 1479; KG8R25), and, therefore, neither of these primers is considered to be a primer of the invention. Nevertheless, the primers set forth as SEQ ID NOS: 11 and 18 can be encompassed within the primer pairs of the invention, including within various disclosed and exemplified primer pairs, for example, the primer pairs set forth as SEQ ID NOS:11 and 12 and as SEQ ID NOS:17 and 18, as well as within combinations of two or more primer pairs, for example, a combination comprising SEQ ID NOS:11 and 12 and SEQ ID NOS:13 and 14.

The primers set forth in SEQ ID NO:9 and SEQ ID NO:10 have been described by Watnick et al. (Am. J. Hum. Genet. 65:1561-1571, 1999, which is incorporated herein by reference) and, therefore, can be specifically excluded from certain embodiments of the invention, as desired, for example, as encompassed within the primers of the invention. It should be recognized, however, that the combination of SEQ ID NOS:9 and 10 as a primer pair is not described by Watnick et al. (supra, 1999). SEQ ID NOS:49 to 51 and 61 to 105 also have been described by Watnick et al. (supra, 1999) and, therefore, can be specifically excluded from certain embodiments of the invention, as desired.

Except as provided herein, a primer of the invention is exemplified by any of SEQ ID NOS:3 to 51 and 61 to 113, as well as substantially identical oligonucleotide primers that are based on or derived from SEQ ID NOS:3 to 51 and 61 to 113. It should be recognized, however, that the primer set forth as SEQ ID NO:12 is substantially similar to the primer designated TWR2 by Watnick et al. (Mol. Cell 2:247-251, 1998, which is incorporated herein by reference; page 250; 5'-GCAGGGTGAGCAGGTGGGGCCATCCTA-3'; SEQ ID NO:60), and that the primer set forth as SEQ ID NO:10 is substantially identical to SEQ ID NO:13 in U.S. Pat. No. 6,071,717 (5'-AGGTCAACGTGGGCCTCCAAG-TAGT-3; SEQ ID NO:52). As such, a primer having the nucleotide sequence of SEQ ID NO:52 or of SEQ ID NO:60 is specifically excluded from the primers that otherwise would be encompassed within the scope of primers that have a sequence substantially identical to the sequence of the primer set forth as SEQ ID NO:12 or SEQ ID NO:10, respectively.

The present invention also provides an isolated mutant PKD1 polynucleotide, or an oligonucleotide portion thereof comprising a mutation as disclosed herein. As used herein, the term "isolated" or "purified," when used in reference to a polynucleotide, oligonucleotide, or polypeptide, means that the material is in a form other than that in which it normally is found in nature. Thus, where a polynucleotide or polypeptide occurs in a cell in nature, an isolated polynucleotide or purified polypeptide can be one that separated, at least in part, from the materials with which it is normally associated. In general, an isolated polynucleotide or a purified polypeptide is present in a form in which it constitutes at least about 5 to 10% of a composition, usually 20% to 50% of a composition, particularly about 50% to 75% of a composition, and preferably about 90% to 95% or more of a composition. Methods for isolating a polynucleotide or polypeptide are well known and routine in the art.

As part of or following isolation, a polynucleotide can be joined to other polynucleotides, such as DNA molecules, for example, for mutagenesis studies, to form fusion proteins, or for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, nevertheless are considered "isolated" because they are not in a form in which they exist in nature. Similarly, the polynucleotides, oligonucleotides, and polypeptides can be present in a composition such as a media formulation (solutions for introduction of polynucleotides, oligonucleotides, or polypeptides, for example, into cells or compositions or solutions for chemical or enzymatic reactions which are not naturally occurring compositions) and, therein remain isolated polynucleotides, oligonucleotides, or polypeptides within the meaning of that term as it is employed herein. An isolated polynucleotide can be a polynucleotide that is not immediately contiguous with nucleotide sequences with which it is immediately contiguous in a genome or other naturally occurring cellular DNA molecule in nature. Thus, a recombinant polynucleotide, which can comprise a polynucleotide incorporated into a vector, an autonomously replicating plasmid, or a virus; or into the genomic DNA of a prokaryote or eukaryote, which does not normally express a PKD1 polypeptide.

As used herein, the term "polynucleotide" or "oligonucleotide" or "nucleotide sequence" or the like refers to a polymer of two or more nucleotides or nucleotide analogs. The polynucleotide can be a ribonucleic acid (RNA) or deoxyribonucleic acid (DNA) molecule, and can be single stranded or double stranded DNA or RNA, or a double stranded DNA:RNA hybrid. A polynucleotide or oligonucleotide can contain one or more modified bases, for example, inosine or a tritylated base. The bonds linking the nucleotides in a polymer generally are phosphodiester bonds, but can be other bonds routinely used to link nucleotides including, for example, phosphorothioate bonds, thioester bonds, and the like. A polynucleotide also can be a chemically, enzymatically or metabolically modified form.

As used herein, the term "mutant PKD1 polynucleotide" means a nucleotide sequence that has one or a few nucleotide changes as compared to the nucleotide sequence set forth as SEQ ID NO:1. The nucleotide change can be a deletion, insertion or substitution, and can be silent such that there is no change in the reading frame of a polypeptide encoded by the PKD1 polynucleotide, or can be a change that results in an amino acid change or in the introduction of a STOP codon into the polynucleotide, or a change in a nucleotide sequence involved in transcription or translation of the PKD1 polynucleotide, for example, a change that results in altered splicing of a PKD1 gene transcript into an mRNA (see Example 2). As disclosed herein, a mutant PKD1 polynucleotide can be a polymorphic variant, which, other than one or a few nucleotide changes with respect to SEQ ID NO:1, encodes a PKD1 polypeptide and does not correlate with a PKD1 associated disorder, particularly ADPKD, or can be a mutant PKD1 polynucleotide that contains one or more mutations that correlate with a PKD1 associated disorder such as ADPKD (see Example 2).

For convenience of discussion and for use as a frame of reference, the PKD1 nucleotide sequence set forth in SEQ ID NO:1 is referred to as a "wild type PKD1 polynucleotide" or a "wild type PKD1 gene" sequence, and, similarly, the polypeptide set forth as SEQ ID NO:2 is referred to as a "wild type PKD1 polypeptide." However, while the presence of the wild type PKD1 gene sequence (i.e., SEQ ID NO:1) in an individual correlates to the absence of ADPKD in the individual, it should be recognized that polymorphic variants of SEQ ID NO:1 also are found in individuals that do not exhibit ADPKD or other PKD1-associated disorder. The term "variants" or "polymorphic variants" is used herein to refer to mutant PKD1 polynucleotide sequences (with respect to SEQ ID NO:1) that do not correlate with the signs or symptoms characteristic of a PKD1 associated disorder such as ADPKD. Variant PKD1 polynucleotides include, for example, nucleotide substitutions that do not result in a change in the encoded amino acid, i.e., silent mutations, such as G4885A, in which the wild type and mutant codons both encode a threonine (T1558T), and C6058T, in which the wild type and mutant codons both, encode a serine (S1949S; see Example 2; see, also, Phakdeekitcharoen et al., supra, 2000); those that do not segregate with the disease, or those that are found in a panel of unaffected individuals. As such, it should be recognized that the term "mutant PKD1 polynucleotide" broadly encompasses PKD1 variants, which do not correlate with a PKD1 associated disorder, as well as mutant PKD1 polynucleotides that correlate or are associated with a PKD1 associated disorder.

Examples of mutant PKD1 polynucleotide sequences, including variant PKD1 polynucleotide sequence, include sequences substantially as set forth in SEQ ID NO:1, but having a mutation at nucleotide 474, wherein nucleotide 474 is a T; nucleotide 487, wherein nucleotide 487 is an A;

nucleotide 3110, wherein nucleotide 3110 is a C; a position corresponding to nucleotide 3336, wherein nucleotide 3336 is deleted; nucleotide 3707, wherein nucleotide 3707 is an A; nucleotide 4168, wherein nucleotide 4168 is a T; nucleotide 4885, wherein nucleotide 4885 is an A; nucleotide 5168, wherein nucleotide 5168 is a T; nucleotide 6058, wherein nucleotide 6058 is a T; nucleotide 6078, wherein nucleotide 6078 is an A; nucleotide 6089, wherein nucleotide 6089 is a T; nucleotide 6195, wherein nucleotide 6195 is an A; nucleotide 6326, wherein nucleotide 6326 is a T; a position corresponding to nucleotides 7205 to 7211, wherein nucleotides 7205 to 7211 are deleted; nucleotide 7376, wherein nucleotide 7376 is a C; a nucleotide sequence corresponding to nucleotides 7535 to 7536, wherein a GCG nucleotide sequence is inserted between nucleotides 7535 and 7536; nucleotide 7415, wherein nucleotide 7415 is a T; nucleotide 7433, wherein nucleotide 7433 is a T; nucleotide 7696, wherein nucleotide 7696 is a T; nucleotide 7883, wherein nucleotide 7883 is a T; nucleotide 8021, wherein nucleotide 8021 is an A; a nucleotide sequence corresponding to nucleotide 8159 to 8160, wherein nucleotides 8159 to 8160 are deleted; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T; or a combination thereof (see Example 2; see, also, Tables 3 and 4). Examples of a mutant PKD1 polynucleotide of the invention also include a polynucleotide that encodes a PKD1 polypeptide having substantially as set forth in SEQ ID NO:2, but having an A88V, W967R, G1166S; V1956E; R1995H; R2408C; D2604N; L2696R, R2985G, R3039C, V3285I, H3311R mutation, or a combination thereof, as well as polypeptides that have, for example, an addition of a Gly residue between amino acid residues 2441 and 2442 of SEQ ID NO:2 due to an insertion, or that terminate with amino acid 3000 of SEQ ID NO:2 due to the presence of a STOP codon at the position in SEQ ID NO:1 that would otherwise encode amino acid 3001 (see, also, Table 4; Example 2).

Additional examples of mutant PKD1 polynucleotides of the invention include polynucleotide sequences that selectively hybridize to the complements of the polynucleotide sequences, or oligonucleotide portions thereof, as disclosed herein, under highly stringent hybridization conditions, e.g., hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel et al., Current Protocols in Molecular Biology, (Green Publishing Associates, Inc., and John Wiley & Sons, Inc., New York 1989), and supplements; see p. 2.10.3; Sambrook et al., Molecular Cloning: A laboratory manual (Cold Spring Harbor Laboratory Press, 1989), which are incorporated herein by reference), as well as polynucleotides that encode a PKD1 polypeptide substantially as set forth in SEQ ID NO:2, but having one or more mutations; or an RNA corresponding to such a polynucleotide.

A polynucleotide or polypeptide sequence that is "substantially identical" to a PKD1 polynucleotide of SEQ ID NO:1 or a polypeptide sequence of SEQ ID NO:2 generally is at least 80% or 85%, usually at least about 90%, and particularly at least about 95%, and preferably at least about 99% identical to the nucleotide sequence or amino acid sequence as set forth in SEQ ID NO:1 or SEQ ID NO:2, respectively. It should be recognized, however, that a mutation in a PKD1 gene sequence can result in the expression of a truncated PKD1 polypeptide, or even a complete loss of expression of the PKD1 polypeptide. As such, while a mutant PKD1 polynucleotide is identified as being substantially identical to SEQ ID NO:1, it may not always be possible to make the same comparison with respect to the encoded polypeptides. In one aspect of the invention, a polynucleotide or polypeptide sequence that is substantially identical to SEQ ID NO:1 or 2 will vary at one or more sites having a mutation, for example, a mutation present in a mutant PKD1 polynucleotide as set forth in the preceding paragraph. Sequence identity can be measured using sequence analysis software (e.g., Sequence Analysis Software Package of the Genetics Computer Group, University of Wisconsin Biotechnology Center, 1710 University Avenue, Madison Wis. 53705).

A polynucleotide or oligonucleotide portion thereof of the invention can be useful, for example, as a probe or as a primer for an amplification reaction. Reference to an "oligonucleotide portion" of a mutant PKD1 polynucleotide means a nucleotide sequence of the mutant PKD1 polynucleotide that is less than the full length polynucleotide. Generally, a polynucleotide useful as a probe or a primer contains at least about 10 nucleotides, and usually contains about 15 to 30 nucleotides or more (see, for example, Tables 1 and 2). Polynucleotides can be prepared by any suitable method, including, for example, by restriction enzyme digestion of an appropriate polynucleotide, by direct chemical synthesis using a method such as the phosphotriester method (Narang et al., 1979, Meth. Enzymol., 68:90-99); the phosphodiester method (Brown et al., 1979, Meth. Enzymol., 68:109-151); the diethylphosphoramidite method (Beaucage et al., 1981, Tetrahedron Lett., 22:1859-1862); the triester method (Matteucci et al., 1981, J. Am. Chem. Soc., 103:3185-3191), including by automated synthesis methods; or by a solid support method (see, for example, U.S. Pat. No. 4,458,066). In addition, a polynucleotide or oligonucleotide can be prepared using recombinant DNA methods as disclosed herein or otherwise known in the art.

An oligonucleotide of the invention can include a portion of a mutant PKD1 polynucleotide, including, for example, a sequence substantially identical to that of SEQ ID NO:1, except wherein nucleotide 474 is a T; or wherein nucleotide 487 is an A; or wherein nucleotide 3110 is a C; or wherein nucleotide 8298 is a G; or wherein nucleotide 9164 is a G; or wherein nucleotide 9213 is an A; or wherein nucleotide 9326 is a T; or wherein nucleotide 9367 is a T; or wherein nucleotide 10064 is an A; or wherein nucleotide 10143 is a G; or wherein nucleotide 10234 is a C; or wherein nucleotide 10255 is a T; or wherein the oligonucleotide contains a combination of such substitutions with respect to SEQ ID NO:1. Thus, as disclosed herein, the oligonucleotide can be any length and can encompass one or more of the above mutations.

An oligonucleotide of the invention can selectively hybridize to a mutant PKD1 polynucleotide sequence as disclosed herein. As such, the oligonucleotide does not hybridize substantially, if at all, to a wild type PKD1 polynucleotide (i.e., to SEQ ID NO:1). As used herein, the term "selectively hybridize" refers to the ability of an oligonucleotide (or polynucleotide) probe to hybridize to a selected sequence, but not to a highly related nucleotide sequence. For example, a oligonucleotide of the invention selectively hybridizes to a mutant PKD1 polynucleotide, but not substantially to a corresponding sequence of SEQ ID NO:1. As such, hybridization of the oligonucleotide to SEQ ID NO:1 generally is not above background, or, if some hybridization occurs, is at least about ten-fold less than the amount of hybridization that occurs with respect to the mutant PKD1 polynucleotide.

In addition, the term "hybridize" is used herein to have its commonly understood meaning of two nucleotide sequences that can associate due to shared complementarity. As disclosed herein, a primer of the invention can hybridize to PDK1 gene and may also hybridize to a PDK1 gene homolog, but generally does not substantially hybridize to a nucleotide sequence other than a PKD1 gene or PKD1 gene homolog. Desired hybridization conditions, including those that allow for selective hybridization, can be obtained by varying the stringency of the hybridization conditions, based, in part, on the length of the sequences involved, the relative G:C content, the salt concentration, and the like (see Sambrook et al., supra, 1989). Hybridization conditions that are highly stringent conditions are used for selective hybridization and can be used for hybridization of a primer or primer pair of the invention to a PKD1 gene or PKD1 gene homolog, and include, for example, washing in 6×SSC/0.05% sodium pyrophosphate at about 37° C. (for 14 nucleotide DNA probe), about 48° C. (for 17 nucleotide probe), about 55° C. (for a 20 nucleotide probe), and about 60° C. (for a 23 nucleotide probe). As disclosed herein, polynucleotides that selectively hybridize to a mutant PKD1 polynucleotide provide a means to distinguish the mutant PKD1 polynucleotide from a wild type PKD1 polynucleotide.

A polynucleotide or oligonucleotide of the invention can be used as a probe to screen for a particular PKD1 variant or mutant of interest. In addition, the oligonucleotides of the invention include a PKD1 antisense molecule, which can be useful, for example, in PKD1 polynucleotide regulation and amplification reactions of PKD1 polynucleotide sequences, including mutant PKD1 polynucleotide sequences. Further, such oligonucleotides can be used as part of ribozyme or triple helix sequence for PKD1 gene regulation. Still further, such oligonucleotides can be used as a component of diagnostic method, whereby the level of PKD1 transcript can be determined or the presence of an ADPKD-causing allele can be detected. Further, such oligonucleotides can be used, for example, to screen for and identify PKD1 homologs from other species.

The term "primer" or "PCR primer" refers to an isolated natural or synthetic oligonucleotide that can act as a point of initiation of DNA synthesis when placed under conditions suitable for primer extension. Synthesis of a primer extension product is initiated in the presence of nucleoside triphosphates and a polymerase in an appropriate buffer at a suitable temperature. A primer can comprise a plurality of primers, for example, where there is some ambiguity in the information regarding one or both ends of the target region to be synthesized. For instance, if a nucleic acid sequence is determined from a protein sequence, a primer generated to synthesize nucleic acid sequence encoding the protein sequence can comprise a collection of primers that contains sequences representing all possible codon variations based on the degeneracy of the genetic code. One or more of the primers in this collection will be homologous with the end of the target sequence or a sequence flanking a target sequence. Likewise, if a conserved region shows significant levels of polymorphism in a population, mixtures of primers can be prepared that will amplify adjacent sequences.

During PCR amplification, primer pairs flanking a target sequence of interest are used to amplify the target sequence. A primer pair typically comprises a forward primer, which hybridizes to the 5' end of the target sequence, and a reverse primer, which hybridizes to the 3' end of the target sequence. Except as otherwise provided herein, primers of the present invention are exemplified by those having the sequences set forth as SEQ ID NOS:3 to 51 and 61 to 113 (see Tables 1 and 2). Forward primers are exemplified by SEQ ID NOS:3, 5, 7, 9, 11, 13, 15, 17, 19, 21, 23, 25, 27, 29, 31, 33, 35, 37, 39, 41, 43, 45, 47 and 49; and reverse primers are exemplified by SEQ ID NOS:4, 6, 8, 10, 12, 14, 16, 18, 20, 22, 24, 26, 28, 30, 32, 34, 36, 38, 40, 42, 44, 46, 48, and 50. A primer pair of the invention includes at least one forward primer and at least one reverse primer that allows for generation of an amplification product, which can be a long range PKD1-specific amplification product or a nested amplification product of such an amplification product, including a forward and reverse primer as set forth in SEQ ID NOS:3 to 18 and of SEQ ID NOS:19 to 51 and 61 to 113, provided that the forward primer is 5' (or upstream) of the reverse primer with reference to a target polynucleotide sequence, and that the primers are in sufficient proximity such that an amplification product can be generated.

Nucleic acid sequences that encode a fusion protein can be produced and can be operatively linked to expression control sequences. Such fusion proteins and compositions are useful in the development of antibodies or to generate and purify peptides and polypeptides of interest. As used herein, the term "operatively linked" refers to a juxtaposition, wherein the components so described are in a relationship permitting them to function in their intended manner. For example, an expression control sequence operatively linked to a coding sequence is ligated such that expression of the coding sequence is achieved under conditions compatible with the expression control sequences, whereas two operatively linked coding sequences can be ligated such that they are in the same reading frame and, therefore, encode a fusion protein.

As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon ATG) in front of a protein-encoding gene, splicing signals for introns, maintenance of the correct reading frame of that gene to permit proper translation of the mRNA, and STOP codons. Control sequences include, at a minimum, components whose presence can influence expression, and can also include additional components whose presence is advantageous, for example, leader sequences and fusion partner sequences. Expression control sequences can include a promoter.

A polynucleotide of the invention can comprise a portion of a recombinant nucleic acid molecule, which, for example, can encode a fusion protein. The polynucleotide, or recombinant nucleic acid molecule, can be inserted into a vector, which can be an expression vector, and can be derived from a plasmid, a virus or the like. The expression vector generally contains an origin of replication, a promoter, and one or more genes that allow phenotypic selection of transformed cells containing the vector. Vectors suitable for use in the present invention include, but are not limited to the T7-based expression vector for expression in bacteria (Rosenberg et al., Gene 56:125, 1987), the pMSXND expression vector for expression in mammalian cells (Lee and Nathans, J. Biol. Chem. 263:3521, 1988); baculovirus-derived vectors for expression in insect cells; and the like.

The choice of a vector will also depend on the size of the polynucleotide sequence and the host cell to be employed in the methods of the invention. Thus, the vector used in the invention can be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequence to be analyzed or modified is large because these vectors are able to stably propagate large polynucleotides. Cosmids and phagemids are particularly suited for the expression or manipulation of the PKD1 polynucleotide of SEQ ID NO:1 or a mutant PKD1 polynucleotide.

In yeast, a number of vectors containing constitutive or inducible promoters can be used (see Ausubel et al., supra, 1989; Grant et al., Meth. Enzymol. 153:516-544, 1987; Glover, DNA Cloning, Vol. II, IRL Press, Washington D.C., Ch. 3, 1986; and Bitter, Meth. Enzymol. 152:673-684, 1987; and The Molecular Biology of the Yeast *Saccharomyces*, Eds. Strathern et al., Cold Spring Harbor Press, Vols. I and II, 1982). A constitutive yeast promoter such as ADH or LEU2 or an inducible promoter such as GAL can be used ("Cloning in Yeast," Ch. 3, Rothstein, In "DNA Cloning" Vol. 11, A Practical ively hybridize to SEQ ID NO:1 and amplify portions of SEQ ID NO:1 comprising about nucleotides 2043 to 4290; nuclNA sequences into the yeast chromosome. The construction of expression vectors and the expression of genes in transfected cells involves the use of molecular cloning techniques also well known in the art (see Sambrook et al., supra, 1989; Ausubel et al., supra, 1989). These methods include in vitro recombinant DNA techniques, synthetic techniques and in vivo recombination/genetic recombination.

A polynucleotide or oligonucleotide can be contained in a vector and can be introduced into a cell by transformation or transfection of the cell. By "transformation" or "transfection" is meant a permanent (stable) or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell can be any prokaryotic or eukaryotic cell into which (or into an ancestor of which) has been introduced, by means of recombinant DNA techniques, a polynucleotide sequence of the invention or fragment thereof. Transformation of a host cell can be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art, or using $MgCl_2$ or RbCl. Transformation can also be performed after forming a protoplast of the host cell or by electroporation.

When the host is a eukaryote, such methods of transfection include the use of calcium phosphate co-precipitates, conventional mechanical procedures such as microinjection, electroporation, insertion of a plasmid encased in liposomes, or the use of virus vectors, or other methods known in the art. One method uses a eukaryotic viral vector, such as simian virus 40 (SV40) or bovine papillomavirus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. The eukaryotic cell can be a yeast cell (e.g., *Saccharomyces cerevisiae*), or can be a mammalian cell, including a human cell.

A variety of host-expression vector systems can be utilized to express a PKD1 polynucleotide sequence such as SEQ ID NO:1, a coding sequence of SEQ ID NO:1 or a mutant PKD1 polynucleotide. Such host-expression systems represent vehicles by which the nucleotide sequences of interest can be produced and subsequently purified, and also represent cells that, when transformed or transfected with the appropriate nucleotide coding sequences, can express a PKD1 protein, including a PKD1 variant or mutant polypeptide or peptide portion thereof in situ. Such cells include, but are not limited to, microorganisms such as bacteria (e.g., *E. coli, B. subtilis*) transformed with recombinant bacteriophage DNA, plasmid DNA or cosmid DNA expression vectors containing a PKD1 polynucleotide, or oligonucleotide portion thereof (wild type, variant or other mutant); yeast (e.g., *Saccharomyces, Pichia*) transformed with recombinant yeast expression vectors containing a PKD1 polynucleotide, or oligonucleotide portions thereof (wild type, variant or other PKD1 mutant); insect cell systems infected with recombinant virus expression vectors (e.g., baculovirus) containing a PKD1 polynucleotide, or oligonucleotide portion thereof (wild type, PKD1 variant or other mutant); plant cell systems infected with recombinant virus expression vectors (e.g., cauliflower mosaic virus or tobacco mosaic virus) or transformed with recombinant plasmid expression vectors (e.g., Ti plasmid) containing a mutant PKD1 polynucleotide, or oligonucleotide portion thereof; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the PKD1 protein (wild type, variant or other PKD1 mutant) being expressed. For example, when a large quantity of such a protein is to be produced, for the generation of antibodies, which can be used to identify or diagnose PKD1-associated diseases or disorders, or to screen peptide libraries, vectors that direct the expression of high levels of fusion protein products that are readily purified can be desirable. Such vectors include, but are not limited to, the *E. coli* expression vector pUR278 (Ruther et al., 1983, EMBO J. 2:1791), in which a PKD1 polynucleotide, or oligonucleotide portion thereof (wild type, variant or other mutant) can be ligated individually into the vector in frame with the lac Z coding region so that a fusion protein is produced; pIN vectors (Inouye and Inouye, Nucl. Acids Res. 13:3101-3109, 1985; Van Heeke and Schuster, J. Biol. Chem. 264:5503-5509, 1989); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned PKD1 protein, variant or mutant can be released from the GST moiety.

In an insect system, *Autographa californica* nuclear polyhedrosis virus (AcNPV) is used as a vector to express foreign genes. The virus grows in *Spodoptera frugiperda* cells. A PKD1 polynucleotide, or oligonucleotide portion thereof can be cloned individually into non-essential regions (for example the polyhedrin gene) of the virus and placed under control of an AcNPV promoter (for example the polyhedrin promoter). Successful insertion of a PKD1 polynucleotide, or oligonucleotide portion thereof will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (see Smith et al., 1983, J. Virol. 46:584; U.S. Pat. No. 4,215,051).

In mammalian host cells, a number of viral-based expression systems can be utilized. In cases where an adenovirus is used as an expression vector, a PKD1 polynucleotide, or oligonucleotide portion thereof, can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome such as the E1 or E3 region results in a recombinant virus that is viable and capable of expressing a PKD1 protein (e.g., wild-type, variants or mutants thereof) in infected hosts (Logan and Shenk, Proc. Natl. Acad. Sci., USA 81:3655-3659, 1984). Specific initiation signals can also be required for efficient translation of an inserted PKD1 sequence. These signals include the ATG initiation codon and adjacent sequences. Where an entire PKD1 polynucleotide, including its own initiation codon and adjacent sequences, is inserted into the appropriate expression vector, no additional translational control signals can be needed. However, where only a portion of a PKD1 sequence is inserted, exogenous translational control signals, including, for example, an ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, and the like (see Bittner et al., Meth. Enzymol. 153:516-544, 1987).

In addition, a host cell strain can be chosen which modulates the expression of the inserted sequences, or modifies and processes the expressed polypeptide in a specific fashion. Such modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein being expressed. To this end, eukaryotic host cells which possess the cellular machinery for proper processing of the primary transcript, glycosylation, and phosphorylation of the polypeptide can be used. Such mammalian host cells include, but are not limited to, CHO, VERO, BHK, HeLa, COS, MDCK, 293, 3T3, WI38, and the like.

For long term, high yield production of recombinant proteins, stable expression is preferred. For example, cell lines that stably express a PKD1 protein, including wild-type, variants or mutants of PKD1, can be engineered. Rather than using expression vectors which contain viral origins of replication, host cells can be transformed with DNA controlled by appropriate expression control elements (e.g., promoter and/or enhancer sequences, transcription terminators, polyadenylation sites, and the like), and a selectable marker. Following the introduction of the foreign DNA, engineered cells can be grown for 1-2 days in an enriched media, then switched to selective media. The selectable marker in the recombinant plasmid confers resistance to the selection and allows cells to stably integrate the plasmid into their chromosomes and grow to form foci, which can be cloned and expanded into cell lines. This method can advantageously be used to engineer cell lines that express a PKD1 variant or mutant polypeptide. Such engineered cell lines can be particularly useful in screening and evaluation of compounds that affect the endogenous activity of a variant or mutant PKD1 polypeptide. Such engineered cell lines also can be useful to discriminate between factors that have specific vs. non-specific effects. In particular, mutant cell lines should lack key functions, and various mutations can be used to identify key functional domains using in vivo assays.

A number of selection systems can be used, including but not limited to the herpes simplex virus thymidine kinase (Wigler et al., Cell 11:223, 1977), hypoxanthine-guanine phosphoribosyltransferase (Szybalska and Szybalski, Proc. Natl. Acad. Sci. USA 48:2026, 1962), and adenine phosphoribosyltransferase (Lowy et al., Cell 22:817, 1980) genes can be employed in $tk^-$, $hgprt^-$ or $aprt^-$ cells, respectively. Also, antimetabolite resistance can be used as the basis of selection for dhfr, which confers resistance to methotrexate (Wigler et al., Proc. Natl. Acad. Sci. USA 77:3567, 1980; O'Hare et al., Proc. Natl. Acad. Sci. USA 78:1527, 1981); gpt, which confers resistance to mycophenolic acid Mulligan and Berg, Proc. Natl. Acad. Sci. USA 78:2072, 1981); neo, which confers resistance to the aminoglycoside G-418 (Colberre-Garapin et al., J. Mol. Biol. 150:1, 1981); and hygro, which confers resistance to hygromycin (Santerre et al., Gene 30:147, 1984) genes. Accordingly, the invention provides a vector that contains a mutant PKD1 polynucleotide, or oligonucleotide portion thereof, or one or more primers or their complements, including an expression vector that contains any of the foregoing sequences operatively associated with a regulatory element that directs the expression of a coding sequence or primer; and also provides a host cell that contains any of the foregoing sequences, alone or operatively associated with a regulatory element, which can directs expression of a polypeptide encoded the polynucleotide, as appropriate.

In addition to mutant PKD1 polynucleotide sequences disclosed herein, homologs of mutant PKD1 polynucleotide of the invention, including a non-human species, can be identified and isolated by molecular biological techniques well known in the art. Further, mutant PKD1 alleles and additional normal alleles of the human PKD1 polynucleotide, can be identified using the methods of the invention. Still further, there can exist genes at other genetic loci within the human genome that encode proteins having extensive homology to one or more domains of the PKD1 polypeptide (SEQ ID NO:2). Such genes can also be identified including associated variants and mutants by the methods of the invention.

A homolog of a mutant PKD1 polynucleotide sequence can be isolated by performing a polymerase chain reaction (PCR; see U.S. Pat. No. 4,683,202, which is incorporated herein by reference) using two oligonucleotide primers, which can be selected, for example, from among SEQ ID NOS:3 to 51, preferably from among SEQ ID NOS: 3 to 18, or can be degenerate primer pools designed on the basis of the amino acid sequences of a PKD1 polypeptide such as that set forth in SEQ ID NO:2 or a mutant thereof as disclosed herein. The template for the reaction can be cDNA obtained by reverse transcription of mRNA prepared from human or non-human cell lines or tissue known to express a PKD1 allele or PKD1 homologue. The PCR product can be subcloned and sequenced or manipulated in any number of ways (e.g., further manipulated by nested PCR) to insure that the amplified sequences represent the sequences of a PKD1 or a PKD mutant polynucleotide sequence. The PCR fragment can then be used to isolate a full length PKD1 cDNA clone (including clones containing a mutant PKD1 polynucleotide sequence) by labeling the amplified fragment and screening a nucleic acid library (e.g., a bacteriophage cDNA library). Alternatively, the labeled fragment can be used to screen a genomic library (for review of cloning strategies, see, for example, Sambrook et al., supra, 1989; Ausubel et al., supra, 1989).

The present invention also provides a purified mutant PKD1 polypeptide, or a peptide portion thereof. As disclosed herein, a mutant PKD1 polypeptide has an amino acid sequence substantially identical to SEQ ID NO:2, and includes a mutation resulting in the deletion, addition (insertion), or substitution of an amino acid of SEQ ID NO:2, or is truncated with respect to SEQ ID NO:2. Examples of such mutations include, with respect to SEQ ID NO:2, an A88V, W967R, G1166S; V1956E; R1995H; R2408C; D2604N; L2696R, R2985G, R3039C, V3285I, or H3311R mutation, an addition of a Gly residue between amino acid residues 2441 and 2442 of SEQ ID NO:2 due to an insertion, or a truncated PKD1 polypeptide terminates with amino acid 3000 of SEQ ID NO:2 due to the presence of a STOP codon at the position in SEQ ID NO:1 that would otherwise encode amino acid 3001; as well as mutant PKD1 polypeptides having a combination of such mutations (see Table 4).

A mutant PKD1 polypeptide or peptide portion thereof can contain one or more of the exemplified mutations. As used herein, reference to a peptide portion of SEQ ID NO:2 or of a mutant PKD1 polypeptide refers to a contiguous amino acid sequence of SEQ ID NO:2 or of SEQ ID NO:2 including a mutation as disclosed herein, respectively, that contains fewer amino acids than full length wild type PKD1 polypeptide. Generally, a peptide portion of a PKD1 polypeptide or a mutant PKD1 polypeptide contains at least about five amino acids (or amino acid derivatives or modified amino acids), each linked by a peptide bond or a modified form thereof, usually contains at least about eight amino acids, particularly contains about ten amino acids, and can contain twenty or thirty or more amino acids of SEQ ID NO:2. In particular, where the peptide is a peptide portion of a mutant PKD1 polypeptide, the peptide includes a mutant amino acid with respect to SEQ ID NO:2.

The mutant PKD1 polypeptides and peptide fragments thereof of the invention include a PKD1 polypeptide or peptide having a sequence substantially identical to that set forth in SEQ ID NO:2, and having one or a combination of the following mutations: A88V, W967R, L2696R, R2985G, R3039C, V3285I, or H3311R, or a mutation resulting in termination of the mutant PKD1 polypeptide at amino acid 3000 (with respect to SEQ ID NO:2) due to the presence of a STOP codon at the position that otherwise would encode amino acid 3001. The wild type PKD1 polypeptide (SEQ ID NO:2) contains 4303 amino acid residues and has a predicted molecular mass of approximately 467 kilodaltons (kDa). Further encompassed by the present invention are mutant PKD1 polypeptides that are truncated with respect to SEQ ID NO:2, for example, a mutation of SEQ ID NO:1 resulting in a G9213A, which results in premature termination of the encoded PKD1 polypeptide (see Example 2). Such truncated products can be associated with PKD1-associated disorders such as ADPKD (see, also, Table 4).

PKD1 polypeptides that are functionally equivalent to a wild type PKD1 polypeptide, including variant PKD1 polypeptides, which can contain a deletion, insertion or substitution of one or more amino acid residues with respect to SEQ ID NO:2, but that nevertheless result in a phenotype that is indistinguishable from that conferred by SEQ ID NO:2, are encompassed within the present invention. Such amino acid substitutions, for example, generally result in similarity in polarity, charge, solubility, hydrophobicity, hydrophilicity, amphipatic nature or the like of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine, glycine, alanine, asparagine, glutamine, serine, threonine, phenylalanine and tyrosine. In many cases, however, a nucleotide substitution can be silent, resulting in no change in the encoded PKD1 polypeptide (see Example 2). Such variant PKD1 polynucleotides are exemplified by those encoded by the variant PKD1 polynucleotide sequences substantially identical to SEQ ID NO:1 (SEQ ID NO:2), but containing (encoding) G487A (A92A), C9367T (G3052G), T10234C (L3341L), and G10255T (R3348R) as shown in Table 3 (see, also, Example 2), and by C9494T (L3095L).

Mutant PKD1 polypeptides and peptide portions thereof that are substantially identical to the PKD1 polypeptide SEQ ID NO:2 or peptide portions thereof, which cause ADPKD symptoms, are encompassed within the scope of the invention. Such mutant PKD1 polypeptides and peptide portions thereof can include dominant mutant PKD1 polypeptides, or PKD1 related polypeptides functionally equivalent to such mutant PKD1 polypeptides. Examples of mutant PKD1 polypeptide sequences include a polypeptide sequences substantially identical to SEQ ID NO:2 having one or more amino acid substitutions such as A88V, W967R, L2696R, R2985G, R3039C, V3285I, or H3311R, or truncated after amino acid 3000. A peptide portion of a mutant PKD1 polypeptide can be 3, 6, 9, 12, 20, 50, 100 or more amino acid residues in length, and includes at least one of the mutations identified above.

A PKD1 wild type or mutant polypeptide, or peptide portions thereof, can be purified from natural sources, as discussed below; can be chemically synthesized; or can be recombinantly expressed. For example, one skilled in the art can synthesize peptide fragments corresponding to a mutated portion of the PKD1 polypeptide as set forth in SEQ ID NO:2 (e.g., including residue 3110) and use the synthesized peptide fragment to generate polyclonal and monoclonal antibodies. Synthetic polypeptides or peptides can be prepared by chemical synthesis, for example, solid-phase chemical peptide synthesis methods, which are well known (see, for example, Merrifield, J. Am. Chem. Soc., 85:2149-2154, 1963; Stewart and Young, Solid Phase Peptide Synthesis, 2d ed., Pierce Chemical Co., Rockford Ill., pages 11-12), and have been employed in commercially available laboratory peptide design and synthesis kits (Cambridge Research Biochemicals). Such commercially available laboratory kits have generally utilized the teachings of Geysen et al., Proc. Natl. Acad. Sci., USA, 81:3998 (1984) and provide for synthesizing peptides upon the tips of a multitude of rods or pins, each of which is connected to a single plate. When such a system is utilized, a plate of rods or pins is inverted and inserted into a second plate of corresponding wells or reservoirs, which contain solutions for attaching or anchoring an appropriate amino acid to the tips of the pins or rods. By repeating such a process step, i.e., inverting and inserting the tips of the rods or pins into appropriate solutions, amino acids are built into desired peptides.

A number of available FMOC peptide synthesis systems are available. For example, assembly of a polypeptide or fragment can be carried out on a solid support using an Applied Biosystems, Inc., Model 431A automated peptide synthesizer. Such equipment provides ready access to the peptides of the invention, either by direct synthesis or by synthesis of a series of fragments that can be coupled using other known techniques. Accordingly, methods for the chemical synthesis of polypeptides and peptides are well-known to those of ordinary skill in the art, e.g., peptides can be synthesized by solid phase techniques, cleaved from the resin and purified by preparative high performance liquid chromatography (see, e.g., Creighton, 1983, Proteins: Structures and Molecular Principles, W. H. Freeman & Co., N.Y., pp. 50-60). The composition of the synthetic peptides can be confirmed by amino acid analysis or sequencing; e.g., using the Edman degradation procedure (see e.g., Creighton, 1983, supra at pp. 34-49). Thus, fragments of the PKD1 polypeptide, variant, or mutant can be chemically synthesized. Peptides can then be used, for example, to generate antibodies useful in the detection of PKD1 variants and mutants, as well as the diagnosis of PKD1-associated disorder (e.g., ADPKD).

A PKD1 polypeptide or peptide, including variants or mutants of the invention, can be substantially purified from natural sources (e.g., purified from cells) using protein separation techniques, well known in the art. Such methods can separate the PKD1 polypeptide away from at least about 90% (on a weight basis), and from at least about 99% of other proteins, glycoproteins, and other macromolecules normally found in such natural sources. Such purification techniques can include, but are not limited to ammonium sulfate precipitation, molecular sieve chromatography, and/or ion exchange chromatography. Alternatively, or additionally, the PKD1 polypeptide, variant, or mutant can be purified by immunoaffinity chromatography using an immunoabsorbent column to which an antibody is immobilized that is capable of specifically binding the PKD1 polypeptide, variant, or mutant. Such an antibody can be monoclonal or polyclonal in origin. For example, an antibody that specifically binds to a mutant PKD1 polypeptide does not bind to a wild-type PKD1 polypeptide or peptide thereof. If the PKD1 polypeptide is glycosylated, the glycosylation pattern can be utilized as part of a purification scheme via, for example, lectin chromatography.

The cellular sources from which the PKD1 polypeptide, variant, or mutants thereof can be purified include, for example, those cells that are shown by northern and/or western blot analysis to express a PKD1 polynucleotide, variant, or mutant sequence. Preferably, such cellular sources are renal cells including, for example, renal tubular epithelial cells, as well as biliary duct cells, skeletal muscle cells, lung alveolar epithelial cell, placental cells, fibroblasts, lymphoblasts, intestinal epithelial cells, and endothelial cells. Other sources include biological fluids, fractionated cells such as organelle preparations, or tissues obtained from a subject. Examples of biological fluids of use with the invention are blood, serum, plasma, urine, mucous, and saliva. Tissue or cell samples can also be used with the invention. The samples can be obtained by many methods such as cellular aspiration, or by surgical removal of a biopsy sample.

PKD1 polypeptides, variants, or mutants of the invention can be secreted out of the cell. Such extracellular font's of the PKD1 polypeptide or mutants thereof can preferably be purified from whole tissue rather than cells, utilizing any of the techniques described above. PKD1 expressing cells such as those described above also can be grown in cell culture, under conditions well known to those of skill in the art. PKD1 polypeptide or mutants thereof can then be purified from the cell media using any of the techniques discussed above.

A PKD1 polypeptide, variant, or mutant can additionally be produced by recombinant DNA technology using the PKD1 nucleotide sequences, variants and mutants described above coupled with techniques well known in the art. Alternatively, RNA capable of encoding PKD1 polypeptides, or peptide fragments thereof, can be chemically synthesized using, for example, automated or semi-automated synthesizers (see, for example, "Oligonucleotide Synthesis", 1984, Gait, ed., IRL Press, Oxford, which is incorporated herein by reference).

When used as a component in the assay systems described herein, the mutant PKD1 polypeptide or peptide can be labeled, either directly or indirectly, to facilitate detection of a complex formed between the PKD1 polypeptide and an antibody or nucleic acid sequence, for example. Any of a variety of suitable labeling systems can be used including, but not limited to, radioisotopes such as $^{125}I$, enzyme labeling systems such as biotin-avidin or horseradish peroxidase, which generates a detectable colorimetric signal or light when exposed to substrate, and fluorescent labels.

The present invention also provides antibodies that specifically bind a PKD1 mutant or PKD1 variant, except that, if desired, an antibody of the invention can exclude an antibody as described in U.S. Pat. No. 5,891,628, which is incorporated herein by reference, or an antibody that that specifically binds a PKD1 mutant as described in U.S. Pat. No. 5,891,628. Antibodies that specifically bind a mutant PKD1 polypeptide are useful as diagnostic or therapeutic reagents and, therefore, can be used, for example, in a diagnostic assay for identifying a subject having or at risk of having ADPKD, and are particularly convenient when provided as a kit.

As used herein, the term "specifically binds," when used in reference to an antibody and an antigen or epitopic portion thereof, means that the antibody and the antigen (or epitope) have a dissociation constant of at least about $1\times10^{-7}$, generally at least about $1\times10^{-8}$, usually at least about $1\times10^{-9}$, and particularly at least about $1\times10^{-10}$ or less. Methods for identifying and selecting an antibody having a desired specificity are well known and routine in the art (see, for example, Harlow and Lane, "Antibodies: A Laboratory Manual" (Cold Spring Harbor Pub. 1988), which is incorporated herein by reference.

Methods for producing antibodies that can specifically bind one or more PKD1 polypeptide epitopes, particularly epitopes unique to a mutant PKD1 polypeptide, are disclosed herein or otherwise well known and routine in the art. Such antibodies can be polyclonal antibodies or monoclonal antibodies (mAbs), and can be humanized or chimeric antibodies, single chain antibodies, anti-idiotypic antibodies, and epitope-binding fragments of any of the above, including, for example, Fab fragments, $F(ab')_2$ fragments or fragments produced by a Fab expression library. Such antibodies can be used, for example, in the detection of PKD1 polypeptides, or mutant PKD1 polypeptides, including variant PKD1 polypeptides, which can be in a biological sample, or can be used for the inhibition of abnormal PKD1 activity. Thus, the antibodies can be utilized as part of ADPKD treatment methods, as well as in diagnostic methods, for example, to detect the presence or amount of a PKD1 polypeptide.

For the production of antibodies that bind to PKD1, including a PKD1 variant or PKD1 mutant, various host animals can be immunized by injection with a PKD1 polypeptide, mutant polypeptide, variant, or a portion thereof. Such host animals can include but are not limited to, rabbits, mice, and rats. Various adjuvants can be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacillus Calmette-Guerin) or *Corynebacterium parvum.*

Antibodies that bind to a mutant PKD1 polypeptide, or peptide portion thereof, of the invention can be prepared using an intact polypeptide or fragments containing small peptides of interest as the immunizing antigen. The polypeptide or a peptide used to immunize an animal can be derived from translated cDNA or chemical synthesis, and can be conjugated to a carrier protein, if desired. Such commonly used carriers that can be chemically coupled to the peptide include keyhole limpet hemocyanin, thyroglobulin, bovine serum albumin, tetanus toxoid and others as described above or otherwise known in the art. The coupled polypeptide or peptide is then used to immunize the animal and antiserum can be collected. If desired, polyclonal or monoclonal antibodies can be purified, for example, by binding to and elution from a matrix to which the polypeptide or a peptide to which the antibodies were raised is bound. Any of various techniques commonly used in immunology for purification and/or concentration of polyclonal antibodies, as well as monoclonal antibodies, can be used (see for example, Coligan, et al., Unit 9, Current Protocols in Immunology, Wiley Interscience, 1991, which is incorporated herein by reference).

Anti-idiotype technology can be used to produce monoclonal antibodies that mimic an epitope. For example, an anti-idiotypic monoclonal antibody made to a first monoclonal antibody will have a binding domain in the hypervariable region that is the image of the epitope bound by the first monoclonal antibody. Antibodies of the invention include polyclonal antibodies, monoclonal antibodies, and fragments of polyclonal and monoclonal antibodies that specifically bind to a mutant PKD1 polypeptide or peptide portion thereof.

The preparation of polyclonal antibodies is well known to those skilled in the art (see, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are incorporated herein by reference). The preparation of monoclonal antibodies likewise is conventional (see, for example, Kohler and Milstein, Nature, 256:495, 1975, which is incorporated herein by reference; see, also Coligan et al., supra, sections 2.5.1-2.6.7; and Harlow et al., supra, 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992)). Methods of in vitro and in vivo multiplication of hybridoma cells expressing monoclonal antibodies is well-known to those skilled in the art. Multiplication in vitro can be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, e.g., syngeneic mice, to cause growth of antibody-producing tumors. Optionally, the animals are primed with a hydrocarbon, especially oils such as pristane tetramethylpentadecane prior to injection. After one to three weeks, the desired monoclonal antibody is recovered from the body fluid of the animal.

Therapeutic applications for antibodies disclosed herein are also part of the present invention. For example, antibodies of the present invention can be derived from subhuman primate antibodies. General techniques for raising therapeutically useful antibodies in baboons can be found, for example, in Goldenberg et al., International Application Publication No. WO 91/11465, 1991; Losman et al., Int. J. Cancer, 46:310, 1990, which are incorporated herein by reference.

An anti-PKD1 antibody also can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Natl. Acad. Sci. USA 86:3833, 1989, which is incorporated herein by reference. Techniques for producing humanized monoclonal antibodies are described, for example, by Jones et al., Nature, 321:522, 1986; Riechmann et al., Nature 332:323, 1988; Verhoeyen et al., Science 239:1534, 1988; Carter et al., Proc. Natl. Acad. Sci. USA, 89:4285, 1992; Sandhu, Crit. Rev. Biotech. 12:437, 1992; and Singer et al., J. Immunol. 150:2844, 1993, which are incorporated herein by reference.

Antibodies of the invention also can be derived from human antibody fragments isolated from a combinatorial immunoglobulin library (see, for example, Barbas et al., Methods: A Companion to Methods in Enzymology, Vol. 2, page 119, 1991; Winter et al., Ann. Rev. Immunol. 12:433, 1994, which are incorporated herein by reference). Cloning and expression vectors that are useful for producing a human immunoglobulin phage library can be obtained, for example, from Stratagene (La Jolla Calif.).

In addition, antibodies of the present invention can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet., 7:13 (1994); Lonberg et al., Nature, 368:856 (1994); Taylor et al., Int. Immunol., 6:579 (1994), each of which is incorporated herein by reference.

Antibody fragments of the invention can be prepared by proteolytic hydrolysis of an antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, each of which in incorporated herein by reference (see, also, Nisonhoff et al., Arch. Biochem. Biophys, 89:230, 1960; Porter, Biochem. J. 73:119, 1959; Edelman et al., Meth. Enzymol. 1:422, 1967; and Coligan et al., at sections 2.8.1-2.8.10 and 2.10.1-2.10.4). Other methods of cleaving antibodies, such as separation of heavy chains to form monovalent light-heavy chain fragments, further cleavage of fragments, or other enzymatic, chemical, or genetic techniques can also be used, provided the fragments bind to the antigen that is recognized by the intact antibody.

Fv fragments comprise an association of $V_H$ and $V_L$ chains, for example, which can be noncovalent (see Inbar et al., Proc. Natl. Acad. Sci. USA 69:2659, 1972). The variable chains also can be linked by an intermolecular disulfide bond, can be crosslinked by a chemical such as glutaraldehyde (Sandhu, supra, 1992), or $F_v$ fragments comprising $V_H$ and $V_L$ chains can be connected by a peptide linker. These single chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: A Companion to Meth. Enzymol., 2:97, 1991; Bird et al., Science 242:423, 1988; Ladner et al., U.S. Pat. No. 4,946,778; Pack et al., BioTechnology 11:1271, 1993; and Sandhu, supra, 1992).

Another form of an antibody fragment is a peptide coding for a single complementarity determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., Methods: A Companion to Meth. Enzymol., 2:106, 1991).

A variety of methods can be employed utilizing reagents such as a mutant PKD1 polynucleotide, or oligonucleotide portion thereof and antibodies directed against a mutant PKD1 polypeptide or peptide. Specifically, such reagents can be used for the detection of the presence of PKD1 mutations, e.g., molecules present in diseased tissue but absent from, or present in greatly reduced levels compared or relative to the corresponding non-diseased tissue.

The methods described herein can be performed, for example, by utilizing pre-packaged kits, which can be diagnostic kits, comprising at least one specific oligonucleotide portion of a PKD1 gene or mutant PKD1 polynucleotide, a primer pair, or an anti-PKD1 antibody reagent as disclosed herein, which can be conveniently used, for example, in a clinical setting to diagnose subjects exhibiting PKD1 abnormalities or to detect PKD1-associated disorders, including ADPKD. Any tissue in which a PKD1 polynucleotide is expressed can be utilized in a diagnostic method of the invention.

Nucleic acids from a tissue to be analyzed can be isolated using procedures that are well known in the art, or a diagnostic procedures can be performed directly on a tissue section (fixed or frozen), which can be obtained from a subject by biopsy or resection, without further purification. Oligonucleotide sequences of the invention can be used as probes or primers for such in situ procedures (Nuovo, 1992, PCR in situ hybridization: protocols and applications, Raven Press, N.Y.). For example, oligonucleotide probes useful in the diagnostic methods of the invention include nucleotide sequences having at least 10 contiguous nucleotides and having a sequence substantially identical to a portion of SEQ ID NO:1, and including nucleotide 474, wherein nucleotide 474 is a T; nucleotide 487, wherein nucleotide 487 is an A; nucleotide 3110, wherein nucleotide 3110 is a C; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; nucleotide 10255, wherein nucleotide 10255 is a T, or a combination thereof. Primers useful in the present invention include those set forth in SEQ ID NOS:3 to 18 and SEQ ID NOS: 19 to 51 and 61 to 112. Such primers flank and can be used to amplify sequences containing one or more mutated nucleotides of a mutant PKD1 polynucleotide.

PKD1 polynucleotide sequences, either RNA or DNA, can be used in hybridization or amplification assays of biological samples to detect abnormalities of PKD1 expression; e.g., Southern or northern blot analysis, single stranded conformational polymorphism (SSCP) analysis including in situ hybridization assays, or polymerase chain reaction analyses, including detecting abnormalities by a methods such as denaturing high performance liquid chromatography (DHPLC; also referred to as temperature-modulated heteroduplex chromatography) or conformation sensitive gel electrophoresis (CSGE), both of which are readily adaptable to high throughput analysis (see, for example, Kristensen et al., BioTechniques 30:318-332, 2001; Leung et al., BioTechniques 30:334-340, 2001, which are incorporated herein by reference). Such analyses can reveal quantitative abnormalities in the expression pattern of the PKD1 polynucleotide, and, if the PKD1 mutation is, for example, an extensive deletion, or the result of a chromosomal rearrangement, can reveal more qualitative aspects of the PKD1 abnormality.

Diagnostic methods for detecting a mutant PKD1 polynucleotide can involve, for example, contacting and incubating nucleic acids derived from a tissue sample being analyzed, with one or more labeled oligonucleotide probes of the invention or with a primer or primer pair of the invention, under conditions favorable for the specific annealing of these reagents to their complementary sequences within the target molecule. After incubation, non-annealed oligonucleotides are removed, and hybridization of the probe or primer, if any, to a nucleic acid from the target tissue is detected. Using such a detection scheme, the target tissue nucleic acid can be immobilized, for example, to a solid support such as a membrane, or a plastic surface such as that on a microtiter plate or polystyrene beads. In this case, after incubation, non-annealed, labeled nucleic acid reagents are easily removed. Detection of the remaining, annealed, labeled nucleic acid reagents is accomplished using standard techniques well known to those in the art.

Oligonucleotide probes or primers of the invention also can be associated with a solid matrix such as a chip in an array, thus providing a means for high throughput methods of analysis. Microfabricated arrays of large numbers of oligonucleotide probes (DNA chips) are useful for a wide variety of applications. Accordingly, methods of diagnosing or detecting a PKD1 variant or mutant can be implemented using a DNA chip for analysis of a PKD1 polynucleotide and detection of mutations therein. A methodology for large scale analysis on DNA chips is described by Hacia et al. (Nature Genet. 14:441-447, 1996; U.S. Pat. No. 6,027,880, which are incorporated herein by reference; see, also, Kristensen et al., supra, 2001). As described in Hacia et al., high density arrays of over 96,000 oligonucleotides, each about 20 nucleotides in length, are immobilized to a single glass or silicon chip using light directed chemical synthesis. Contingent on the number and design of the oligonucleotide probe, potentially every base in a sequence can be examined for alterations.

Polynucleotides or oligonucleotides applied to a chip can contain sequence variations, which can be used to identify mutations that are not yet known to occur in the population, or they can only those mutations that are known to occur, including those disclosed herein (see Example 2). Examples of oligonucleotides that can be applied to the chip include oligonucleotides containing at least 10 contiguous nucleotides and having a sequence substantially identical to a portion of SEQ ID NO:1, and including nucleotide 474, wherein nucleotide 474 is a T; nucleotide 487, wherein nucleotide 487 is an A; nucleotide 3110, wherein nucleotide 3110 is a C; a position corresponding to nucleotide 3336, wherein nucleotide 3336 is deleted; nucleotide 3707, wherein nucleotide 3707 is an A; nucleotide 4168, wherein nucleotide 4168 is a T; nucleotide 4885, wherein nucleotide 4885 is an A; nucleotide 5168, wherein nucleotide 5168 is a T; nucleotide 6058, wherein nucleotide 6058 is a T; nucleotide 6078, wherein nucleotide 6078 is an A; nucleotide 6089, wherein nucleotide 6089 is a T; nucleotide 6195, wherein nucleotide 6195 is an A; nucleotide 6326, wherein nucleotide 6326 is a T; a position corresponding to nucleotides 7205 to 7211, wherein nucleotides 7205 to 7211 are deleted; nucleotide 7376, wherein nucleotide 7376 is a C; a nucleotide sequence corresponding to nucleotides 7535 to 7536, wherein a GCG nucleotide sequence is inserted between nucleotides 7535 and 7536; nucleotide 7415, wherein nucleotide 7415 is a T; nucleotide 7433, wherein nucleotide 7433 is a T; nucleotide 7696, wherein nucleotide 7696 is a T; nucleotide 7883, wherein nucleotide 7883 is a T; nucleotide 8021, wherein nucleotide 8021 is an A; a nucleotide sequence corresponding to nucleotide 8159 to 8160, wherein nucleotides 8159 to 8160 are deleted; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; nucleotide 10255, wherein nucleotide 10255 is a T; or a combination thereof.

Prior to hybridization with oligonucleotide probes on the chip, the test sample is isolated, amplified and labeled (e.g. fluorescent markers). The test polynucleotide sample is then hybridized to the immobilized oligonucleotides. The intensity of sequence-based techniques of the target polynucleotide to the immobilized probe is quantitated and compared to a reference sequence. The resulting genetic information can be used in molecular diagnosis. A common utility of the DNA chip in molecular diagnosis is screening for known mutations.

In addition to DNA chip methodology, methods using machinery adapted to DNA analysis can allow for commercialization of the disclosed methods of detection of PKD1 mutations and diagnosis of ADPKD. For example, genotyping by mass spectrometry can be used, or matrix-assisted laser desorption/ionization-time-of-flight (MALDI-TOF) mass spectrometry can be used for mass genotyping of single-base pair and short tandem repeat mutant and variant sequences. For example, PCR amplification of the region of the mutation with biotin attached to one of the primers can be conducted, followed by immobilization of the amplified DNA to streptavidin beads. Hybridization of a primer adjacent to the variant or mutant site is performed, then extension with DNA polymerase past the variant or mutant site in the presence of dNTPs and ddNTPs is performed. When suitably designed according to the sequence, this results in the addition of only a few additional bases (Braun, Little, Koster, 1997). The DNA is then processed to remove unused nucleotides and salts, and the short primer plus mutant site is removed by denaturation and transferred to silicon wafers using a piezoelectric pipette. The mass of the primer+variant or mutant site is then determined by delayed extraction MALDI-TOF mass spectrometry. Single base pair and tandem repeat variations in sequence are easily determined by their mass. This final step is very rapid, requiring only 5 sec per assay, and all of these steps can be automated, providing the potential of performing up to 20,000 genotypings per day. This technology is rapid, extremely accurate, and adaptable to any variant or mutation, can identify both single base pair and short tandem repeat variants, and adding or removing variant or mutant sequences to be tested can be done in a few seconds at trivial cost.

Another diagnostic methods for the detection of mutant PKD1 polynucleotides involves amplification, for example, by PCR (see U.S. Pat. No. 4,683,202), ligase chain reaction (Barany, Proc. Natl. Acad. Sci. USA 88:189-193, 1991a), self sustained sequence replication (Guatelli et al., Proc. Natl. Acad. Sci. USA 87:1874-1878, 1990), transcriptional amplification system (Kwoh et al., Proc. Natl. Acad. Sci. USA 86:1173-1177, 1989), Q-Beta Replicase (Lizardi et al., Bio/Technology 6:1197, 1988), or any other RNA amplification method, followed by the detection of the amplification products. The present invention provides reagents, methods and compositions that can be used to overcome prior difficulties with diagnosing ADPKD.

Using the primer pairs and methods described herein, the entire replicated segment of the PKD1 gene, including exons 1 and 22, can be amplified from genomic DNA to generate a set of eight long range amplification products, which range in size from about 0.3 kb to 5.8 kb (Table 1; see, also, FIG. 1). The availability of widely scattered PKD1-specific primers provides a means to anchor PKD1-specific amplification, and the ability to use various primer combinations provides a means to produce longer or shorter amplification products as desired. For example, the largest PKD1 fragment, which is amplified by primers BPF13 and KG8R25 (see Table 1; SEQ ID NOS: 17 and 18, respectively), can be divided into two shorter segments by using the PKD1-specific primer, KG85R25 (SEQ ID NO:18), with forward nested primer F32 (5'-GCCTTGCGCAGCTTGGACT-3'; SEQ ID NO:53), and using BPF13 (SEQ ID NO:17) and a second specific primer, 31R (5'-ACAGTGTCTTGAGTCCAAGC-3'; SEQ ID NO:54).

It should be recognized that, while many of the primers disclosed herein are positioned with intronic sequences of the PKD1 gene, others such as SEQ ID NO:16 are positioned in coding sequences. As such, a cDNA molecule can obtained from a target RNA molecule, for example, by reverse transcription of the RNA molecule using a primer such as SEQ ID NO:16 and an appropriate second primer positioned 5' or 3' to SEQ ID NO:16. In this embodiment, a PKD1 RNA can be isolated from any tissue in which wild type PKD1 is known to be expressed, including, for example, kidney tissue, nucleated peripheral blood cells, and fibroblasts. A target sequence within the cDNA is then used as the template for a nucleic acid amplification reaction, such as a PCR amplification reaction, or the like. An amplification product can be detected, for example, using radioactively or fluorescently labeled nucleotides or the like and an appropriate detection system, or by generating a sufficient amount of the amplification product such that it can be visualized by ethidium bromide staining and gel electrophoresis.

Genomic DNA from a subject, including from a cell or tissue sample, can be used as the template for generating a long range PKD1-specific amplification product. Methods of isolating genomic DNA are well known and routine (see Sambrook et al., supra, 1989). Amplification of the genomic PKD1 DNA has advantages over the cDNA amplification process, including, for example, allowing for analysis of exons and introns of the PKD1 gene. As such, a target sequence of interest associated with either an intron or exon sequence of a PKD1 gene can be amplified and characterized. A target sequence of interest is any sequence or locus of a PKD1 gene that contains or is thought to contain a mutation, including those mutations that correlate to a PKD1-associated disorder or disease.

Using primers flanking the target sequence, a sufficient number of PCR cycles is performed to provide a PKD1-specific amplification product corresponding to the target sequence. If desired, additional amplification can be performed, for example, by performing a nested PCR reaction. Examples of primers useful for generating a PKD1-specific first amplification product from genomic DNA include the primer pairs having sequences as exemplified in SEQ ID NO:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; and SEQ ID NOS:17 and 18. The PKD1-specific first amplification product can be further amplified using nested primers specific for a target sequence, including the primer pairs exemplified as SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; and the primer pairs formed using consecutive primers set forth in Table 2 as SEQ ID NOS:62 to 96, 113, and 97 to 112.

The amplified target sequences can be examined for changes (i.e., mutations) with respect to SEQ ID NO:1 using any of various well known methods as disclosed herein or otherwise known in the art. For example, the amplification products can simply be sequenced using routine DNA sequencing methods, particularly where only one or few amplification products are to be examined. However, DNA sequencing will be more valuable as a method of detecting mutations according to a method of the invention as sequencing technology improves and becomes more adaptable to high throughput screening assays. In addition, methods that are useful for detecting the presence of a mutation in a DNA sequence include, for example, DHPLC (Huber et al., Nucl. Acids Res. 21:1061-10666, 1993; Liu et al., Nucl. Acids Res. 26:1396-1400, 1998; Choy et al., Ann. Hum. Genet. 63:383-391, 1999; Ellis et al., Hum. Mutat. 15:556-564, 2000; which are incorporated herein by reference; see, also, Kristensen et al., supra, 2001); CSGE (Leung et al., supra, 2001); single-stranded conformation analysis (SSCA; Orita et al., Proc. Natl. Acad. Sci., USA 86:2766-2770, 1989); denaturing gradient gel electrophoresis (DGGE; Sheffield et al., Proc. Natl. Acad. Sci., USA 86:232-236, 1989); RNase protection assays; allele-specific oligonucleotides (ASOs; Handelin and Shuber, Current Protocols in Human Genetics, Suppl. 16 (John Wiley & Sons, Inc. 1998), 9:9.4.1-9.4.8); the use of proteins that recognize nucleotide mismatches, such as the *E. coli* mutS protein; and allele-specific PCR.

For allele-specific PCR, primers are used that hybridize at their 3' ends to a particular mutations. Examples of primers that can be used for allele specific PCR include an oligonucleotide of at least 10 nucleotide of SEQ ID NO:1 and that has at its 3' end nucleotide 474, wherein nucleotide 474 is a T; nucleotide 487, wherein nucleotide 487 is an A; nucleotide 3110, wherein nucleotide 3110 is a C; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T. If the particular mutation is not present, an amplification product is not observed. Amplification Refractory Mutation System (ARMS) can also be used (see European Patent Application Publ. No. 0332435; Newton et al., Nucl. Acids. Res. 17:2503-2516, 1989).

In the SSCA, DGGE and RNase protection methods, a distinctive electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed that detects a specific sequence, and the assay is performed by detecting the presence or absence of a hybridization signal. In the mutS assay, the protein binds only to sequences that contain a nucleotide mismatch in a heteroduplex between mutant and wild-type sequences.

Denaturing gradient gel electrophoresis is based on the melting behavior of the DNA fragments and the use of denaturing gradient gel electrophoresis as shown by Fischer and Lerman, Proc. Natl. Acad. Sci. USA 80:1579-83, 1983; Myers et al.; Nucl. Acids Res. 13:3111-3129, 1985; Lerman et al., in Molecular Biol. of *Homo Sapiens*, Cold Spring Harbor Lab. (1986) pp. 285-297. DNA fragments differing by single base substitutions can be separated from each other by electrophoresis in polyacrylamide gels containing an ascending gradient of the DNA denaturants urea and formamide. Two identical DNA fragments differing by only one single base pair, will initially move through the polyacrylamide gel at a constant rate. As they migrate into a critical concentration of denaturant, specific domains within the fragments melt to produce partially denatured DNA. Melting of a domain is accompanied by an abrupt decrease in mobility. The position in the denaturant gradient gel at which the decrease in mobility is observed corresponds to the melting temperature of that domain. Since a single base substitution within the melting domain results in a melting temperature difference, partial denaturation of the two DNA fragments will occur at different positions in the gel. DNA molecules can therefore be separated on the basis of very small differences in the melting temperature. Additional improvements to this DGGE have been made as disclosed by Borresen in U.S. Pat. No. 5,190,856. In addition, after a first DGGE analysis, an identified product can be cloned, purified and analyzed a second time by DGGE.

Denaturing high performance liquid chromatography (DHPLC; Kristensen et al., supra, 2001) and high throughput conformation sensitive gel electrophoresis (HTCSGD; Leung et al., supra, 2001) are particularly useful methods for detecting a mutant PKD1 polynucleotide sequence because the methods are readily adaptable to high throughput analysis. In addition, these methods are suitable for detecting known mutations as well as identifying previously unknown mutations. As such, these methods of detection can be adopted for use in clinical diagnostic settings. DHPLC, for example, can be used to rapidly screen a large number of samples, for example, 96 samples prepared using a 96 well microtiter plate format, to identify those showing a change in the denaturation properties. Where such a change is identified, confirmation that the PKD1 polynucleotide in the sample showing the altered denaturation property is a mutant PKD1 polynucleotide can be confirmed by DNA sequence analysis, if desired.

An oligonucleotide probe specific for a mutant PKD1 polynucleotide also can be used to detect a mutant PKD1 polynucleotide in a biological sample, including in a biological fluid, in cells or tissues obtained from a subject, or in a cellular fraction such as an organelle preparation. Cellular sources useful as samples for identifying a mutant PKD1 polynucleotide include, for example, renal cells including renal tubular epithelial cells, bile duct cells, skeletal muscle cells, lung alveolar epithelial cells, placental cells, fibroblasts and lymphocytes. Biological fluids useful as samples for identifying a mutant PKD1 polynucleotide include, for example, whole blood or serum or plasma fractions, urine, mucous, and saliva. A biological sample such as a tissue or cell sample can be obtained by any method routinely used in a clinical setting, including, for example, by cellular aspiration, biopsy or other surgical procedure.

The oligonucleotide probe can be labeled with a compound that allows detection of binding to a mutant PKD1 polynucleotide in the sample. A detectable compound can be, for example, a radioactive label, which provides a highly sensitive means for detection, or a non-radioactive label such as a fluorescent, luminescent, chemiluminescent, or enzymatically detectable label or the like (see, for example, Matthews et al., Anal. Biochem. 169:1-25, 1988).

The method of detection can be a direct or indirect method. An indirect detection process can involve, for example, the use of an oligonucleotide probe that is labeled with a hapten or ligand such as digoxigenin or biotin. Following hybridization, the target-probe duplex is detected by the formation of an antibody or streptavidin complex, which can further include an enzyme such as horseradish peroxidase, alkaline phosphatase, or the like. Such detection systems can be prepared using routine methods, or can be obtained from a commercial source. For example, the GENIUS detection system (Boehringer Mannheim) is useful for mutational analysis of DNA, and provides an indirect method using digoxigenin as a tag for the oligonucleotide probe and an anti-digoxigenin-antibody-alkaline phosphatase conjugate as the reagent for identifying the presence of tagged probe.

Direct detection methods can utilize, for example, fluorescent labeled oligonucleotides, lanthanide chelate labeled oligonucleotides or oligonucleotide-enzyme conjugates. Examples of fluorescent labels include fluorescein, rhodamine and phthalocyanine dyes. Examples of lanthanide chelates include complexes of europium ($Eu^{3+}$) or terbium ($Tb^{3+}$). Oligonucleotide-enzyme conjugates are particularly useful for detecting point mutations when using target-specific oligonucleotides, as they provide very high sensitivities of detection. Oligonucleotide-enzyme conjugates can be prepared by a number of methods (Jablonski et al., Nucl. Acids Res. 14:6115-6128, 1986; Li et al., Nucl. Acids. Res. 15:5275-5287, 1987; Ghosh et al., Bioconjugate Chem. 1:71-76, 1990). The detection of target nucleic acids using these conjugates can be carried out by filter hybridization methods or by bead-based sandwich hybridization (Ishii et al., Bioconjugate Chem. 4:34-41, 1993).

Methods for detecting a labeled oligonucleotide probe are well known in the art and will depend on the particular label. For radioisotopes, detection is by autoradiography, scintillation counting or phosphor imaging. For hapten or biotin labels, detection is with antibody or streptavidin bound to a reporter enzyme such as horseradish peroxidase or alkaline phosphatase, which is then detected by enzymatic means. For fluorophor or lanthanide chelate labels, fluorescent signals can be measured with spectrofluorimeters, with or without time-resolved mode or using automated microtiter plate readers. For enzyme labels, detection is by color or dye deposition, for example, p-nitrophenyl phosphate or 5-bromo-4-chloro-3-indolyl phosphate/nitroblue tetrazolium for alkaline phosphatase, and 3,3'-diaminobenzidine-$NiCl_2$ for horseradish peroxidase, fluorescence by 4-methyl umbelliferyl phosphate for alkaline phosphatase, or chemiluminescence by the alkaline phosphatase dioxetane substrates LumiPhos 530 (Lumigen Inc., Detroit Mich.) or AMPPD and CSPD (Tropix, Inc.). Chemiluminescent detection can be carried out with X-ray or Polaroid film, or by using single photon counting luminometers, which also is a useful detection format for alkaline phosphatase labeled probes.

Mutational analysis can also be carried out by methods based on ligation of oligonucleotide sequences that anneal immediately adjacent to each other on a target DNA or RNA molecule (Wu and Wallace, Genomics 4:560-569, 1989; Landren et al., Science 241:1077-1080, 1988; Nickerson et al., Proc. Natl. Acad. Sci. USA 87:8923-8927, 1990; Barany, supra, 1991a). Ligase-mediated covalent attachment occurs only when the oligonucleotides are correctly base-paired. The ligase chain reaction (LCR) and the oligonucleotide ligation assay (OLA), which utilize the thermostable Taq ligase for target amplification, are particularly useful for interrogating mutation loci. The elevated reaction temperatures permit the ligation reaction to be conducted with high stringency (Barany, PCR Methods and Applications 1:5-16, 1991b; Grossman et al., Nucl. Acids. Res. 22:4527-4534, 1994, which are incorporated herein by reference).

Analysis of point mutations in DNA can also be carried out by using PCR and variations thereof. Mismatches can be detected by competitive oligonucleotide priming under hybridization conditions where binding of the perfectly matched primer is favored (Gibbs et al., Nucl. Acids. Res. 17:2437-2448, 1989). In the amplification refractory mutation system technique (ARMS), primers can be designed to have perfect matches or mismatches with target sequences either internal or at the 3' residue (Newton et al., supra, 1989). Under appropriate conditions, only the perfectly annealed oligonucleotide can function as a primer for the PCR reaction, thus providing a method of discrimination between normal and mutant sequences.

Detection of single base mutations in target nucleic acids can be conveniently accomplished by differential hybridization techniques using sequence-specific oligonucleotides (Suggs et al., Proc. Natl. Acad. Sci. USA 78:6613-6617, 1981; Conner et al., Proc. Natl. Acad. Sci. USA 80:278-282, 1983; Saiki et al., Proc. Natl. Acad. Sci. USA 86:6230-6234, 1989). Mutations can be diagnosed on the basis of the higher thermal stability of the perfectly matched probes as compared to the mismatched probes. The hybridization reactions can be carried out in a filter-based format, in which the target nucleic acids are immobilized on nitrocellulose or nylon membranes and probed with oligonucleotide probes. Any of the known hybridization formats can be used, including Southern blots, slot blots, reverse dot blots, solution hybridization, solid support based sandwich hybridization, bead-based, silicon chip-based and microtiter well-based hybridization formats.

An alternative strategy involves detection of the mutant sequences by sandwich hybridization methods. In this strategy, the mutant and wild type target nucleic acids are separated from non-homologous DNA/RNA using a common capture oligonucleotide immobilized on a solid support and detected by specific oligonucleotide probes tagged with reporter labels. The capture oligonucleotides can be immobilized on microtiter plate wells or on beads (Gingeras et al., J. Infect. Dis. 164:1066-1074, 1991; Richen et al., Proc. Natl. Acad. Sci. USA 88:11241-11245, 1991).

Another method for analysis of a biological sample for specific mutations in a PKD1 polynucleotide sequence (e.g., mutant PKD1 polynucleotides, or oligonucleotide portions thereof) is a multiplexed primer extension method. In this method primer is hybridized to a nucleic acid suspected of containing a mutation such that the primer is hybridized 3' to the suspected mutation. The primer is extended in the presence of a mixture of one to three deoxynucleoside triphosphates and one of three chain terminating deoxynucleoside triphosphates selected such that the wild-type extension product, the mutant DNA-derived extension product and the primer each are of different lengths. These steps can be repeated, such as by PCR or RT-PCR, and the resulting primer extended products and primer are then separated on the basis of molecular weight to thereby enable identification of mutant DNA-derived extension product.

In one aspect of the invention, the OLA is applied for quantitative mutational analysis of PKD1 polynucleotide sequences (Grossman, et al., supra, 1994). In this embodiment of the invention, a thermostable ligase-catalyzed reaction is used to link a fluorescently labeled common probe with allele-specific probes. The latter probes are sequence-coded with non-nucleotide mobility modifiers that confer unique electrophoretic mobilities to the ligation products.

Oligonucleotides specific for wild type or mutant PKD1 sequences can be synthesized with different oligomeric nucleotide or non-nucleotide modifier tails at their 5' termini. Examples of nucleotide modifiers are inosine or thymidine residues, whereas examples of non-nucleotide modifiers include pentaethyleneoxide (PEO) and hexaethyleneoxide (HEO) monomeric units. The non-nucleotide modifiers are preferred and most preferably PEO is used to label the probes. When a DNA template is present, a thermostable DNA ligase catalyzes the ligation of normal and mutant probes to a common probe bearing a fluorescent label. The PEO tails modify the mobilities of the ligation products in electrophoretic gels. The combination of PEO tails and fluorophor labels (TET and FAM (5-carboxy-fluorescein derivatives)), HEX and JOE (6-carboxy-fluorescein derivatives), ROX (6-carboxy-x-rhodamine), or TAMRA (N,N,N',N'-tetramethyl-6-carboxy-rhodamine; Perkin-Elmer, ABI Division, Foster City Calif.) allow multiplex analysis based on size and color by providing unique electrophoretic signatures to the ligation products. The products are separated by electrophoresis, and fluorescence intensities associated with wild type and mutant products are used to quantitate heteroplasmy. Thus, wild type and mutant, including variant, sequences are detected and quantitated on the basis of size and fluorescence intensities of the ligation products. This method further can be configured for quantitative detection of multiple PKD1 polynucleotide mutations in a single ligation reaction.

Mismatch detection or mutation analysis can also be performed using mismatch specific DNA intercalating agents. Such agents intercalate at a site having a mismatch followed by visualization on a polyacrylamide or agarose gel or by electrocatalysis. Accordingly, PKD1 polynucleotide sequences can be contacted with probes specific for a PKD1 mutation or probes that are wild type for an area having a specific mutation under conditions such that the PKD1 polynucleotide and probe hybridize. The hybridized sequences are then contacted with a mismatch intercalating agent and, for example, separated on a gel. Visualized bands on the gel correspond to a sequence having a mismatch. If the probes are wild-type probes mismatches will occur if the target PKD1 sequence contains a mismatch. If the probes are specific for a mutated sequence mismatches will be present where the target PKD1 sequence is wild type, but the hybridized or duplex sequences will not contain mismatches where the probe sequence hybridizes to a PKD1 sequence containing the same mutation.

For quantitative analysis of PKD1 mutations using OLA, oligonucleotide probes are preferably labeled with fluorophor labels that provide spectrally distinguishable characteristics. In one embodiment, oligonucleotides are labeled with 5' oligomeric PEO tails. Synthesis of such 5' labeled oligonucleotides can be carried out, for example, using an automated synthesizer using standard phosphoramidite chemistry. Following cleavage from resin and deprotection with ammonium hydroxide, the $(PEO)_n$-oligonucleotides can be purified by reverse phase HPLC. Oligonucleotides with 3'-FAM or TET dyes (Perkin Elmer) and 5'-phosphates can be synthesized and purified by the procedure of Grossman et al., supra, 1994. The 5'-PEO-labeled probes can be synthesized to have 5'-PEO-tails of differing lengths to facilitate distinguishing the ligated probe products both electrophoretically by size and by spectral characteristics of the fluorophor labels.

The oligonucleotide probes are used for identifying mutant PKD1 polynucleotides, which can be indicative of a PKD1-associated disorder such as ADPKD. Preferably, the probes are specific for one or more PKD1 nucleotide positions of SEQ ID NO:1 selected from nucleotide 474, wherein nucleotide 474 is a T; nucleotide 487, wherein nucleotide 487 is an A; nucleotide 3110, wherein nucleotide 3110 is a C; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T. The oligonucleotide probes for the OLA assay are typically designed to have calculated melting temperatures of about 40° C. to 50° C., generally about 48° C., by the nearest neighbor method (Breslaur et al., Proc. Natl. Acad. Sci. USA 83:9373-9377, 1986) so that the ligation reaction can be performed at a temperature range of about 40° C. to 60° C., typically from about 45° C. to about 55° C. The wild type and mutant, including variant, oligonucleotide probes can be synthesized with various combinations of PEO oligomeric tails and fluorescein dyes such as TET and FAM. These combinations of mobility modifiers and fluorophor labels furnish electrophoretically unique ligation products that can enable the monitoring of two or more PKD1 nucleotide sites in a single ligation reaction.

In one embodiment, a method of diagnosing a PKD1-associated disorder in a subject is performed by amplifying a portion of a PKD1 polynucleotide in a nucleic acid sample from a subject suspected of having a PKD1-associated disorder with at least a first primer pair to obtain a first amplification product, wherein said first primer pair is a primer pair of claim 3; amplifying the first amplification product with at least a second primer pair to obtain a nested amplification product, wherein the second primer pair is suitable for performing nested amplification of the first amplification product; and determining whether the nested amplification product has a mutation associated with a PKD1-associated disorder, wherein the presence of a mutation associated with a PKD1-associated disorder is indicative of a PKD1-associated disorder, thereby diagnosing a PKD1-associated disorder in the subject. The method can be performed using a first primer pair selected from SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; and a combination thereof, and a second primer pair selected from SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; SEQ ID NOS:62 and 63; SEQ ID NOS:64 and 65; SEQ ID NOS:66 and 67; SEQ ID NOS:68 and 69; SEQ ID NOS:70 and 71; SEQ ID NOS:72 and 73; SEQ ID NOS:74 and 75; SEQ ID NOS:76 and 77; SEQ ID NOS:78 and 79; SEQ ID NOS:80 and 81; SEQ ID NOS:82 and 83; SEQ ID NOS:84 and 85; SEQ ID NOS:86 and 87; SEQ ID NOS:88 and 89; SEQ ID NOS:90 and 91; SEQ ID NOS:92 and 93; SEQ ID NOS:94 and 95; SEQ ID NOS:96 and 113; SEQ ID NOS:97 and 98; SEQ ID NOS:99 and 100; SEQ ID NOS:101 and 102; SEQ ID NOS:103 and 104; SEQ ID NOS: 105 and 106; SEQ ID NOS:107 and 108; SEQ ID NOS:109 and 110; or SEQ ID NOS:111 and 112; and a combination thereof.

In another embodiment, a method of diagnosing a PKD1-associated disorder in a subject is performed by amplifying a portion of PKD1 polynucleotide in a nucleic acid sample from a subject suspected of having a PKD1-associated disorder with a first primer pair to obtain a first amplification product; amplifying the first amplification product using a second primer pair to obtain a second amplification product; and detecting a mutation in the second amplification product, wherein the mutation comprises SEQ ID NO:1 wherein nucleotide 3110 is a C; nucleotide 3336 is deleted; nucleotide 3707 is an A; nucleotide 5168 is a T; nucleotide 6078 is an A; nucleotide 6089 is a T; nucleotide 6326 is a T; nucleotides 7205 to 7211 are deleted; nucleotide 7415 is a T; nucleotide 7433 is a T; nucleotide 7883 is a T; or nucleotides 8159 to 8160 are deleted; nucleotide 8298 is a G; nucleotide 9164 is a G; nucleotide 9213 is an A; or nucleotide 9326 is a T; nucleotide 10064 is an A; or wherein a GCG nucleotide sequence is inserted between nucleotides 7535 and 7536; or a combination thereof, thereby diagnosing a PKD1-associated disorder in the subject.

The present invention also provides a method of identifying a subject having or at risk of having a PKD1-associated disorder. Such a method can be performed, for example, by comprising contacting nucleic acid molecules in a sample from a subject with at least one primer pair of the invention under conditions suitable for amplification of a PKD1 polynucleotide by the primer pair, thereby generating a PKD1-specific amplification product; and testing an amplification product for the presence or absence of a mutation indicative of a PKD1-associated disorder, wherein the absence of the mutation identifies the subject a not having or at risk of the having a PKD1-associated disorder, and wherein the presence of the mutation identifies the subject as having or is at risk of having a PKD1-associated disorder. The primer pair can be, for example, selected from SEQ ID NO:3 and 4; SEQ ID NO:5 and 6; SEQ ID NOS:7 and 8; SEQ ID NOS:9 and 10; SEQ ID NOS:11 and 12; SEQ ID NOS:13 and 14; SEQ ID NOS:15 and 16; or SEQ ID NOS:17 and 18. The PKD1-associated disorder can be autosomal dominant polycystic kidney disease, acquired cystic disease, or any other PKD-1 associated disorder, and the subject can be, for example, a vertebrate, particularly a human subject.

Such a method is particularly adaptable to a high throughput format, and, if desired, can include a step of contacting the PKD1-specific amplification product with at least a second primer pair, under conditions suitable for nested amplification of the PKD1-specific amplification product by a second primer pair, thereby generating a nested amplification product, then testing the nested amplification product for the presence or absence of a mutation indicative of a PKD1-associated disorder. The second primer pair can be any primer pair suitable for nested amplification of the PKD1-specific amplification product, for example, a primer pair selected from SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; SEQ ID NOS:62 and 63; SEQ ID NOS:64 and 65; SEQ ID NOS:66 and 67; SEQ ID NOS:68 and 69; SEQ ID NOS:70 and 71; SEQ ID NOS:72 and 73; SEQ ID NOS:74 and 75; SEQ ID NOS:76 and 77; SEQ ID NOS:78 and 79; SEQ ID NOS:80 and 81; SEQ ID NOS:82 and 83; SEQ ID NOS:84 and 85; SEQ ID NOS:86 and 87; SEQ ID NOS:88 and 89; SEQ ID NOS:90 and 91; SEQ ID NOS:92 and 93; SEQ ID NOS:94 and 95; SEQ ID NOS:96 and 113; SEQ ID NOS:97 and 98; SEQ ID NOS:99 and 100; SEQ ID NOS:101 and 102; SEQ ID NOS:103 and 104; SEQ ID NOS: 105 and 106; SEQ ID NOS:107 and 108; SEQ ID NOS:109 and 110; or SEQ ID NOS:111 and 112; and a combination thereof.

Testing an amplification product for the presence or absence of the mutation can be performed using any of various well known methods for examining a nucleic acid molecule. For example, nucleotide sequence of the amplification product can be determined, and compared with the nucleotide sequence of a corresponding nucleotide sequence of SEQ ID NO:1. The amplification product also can be tested by determining the melting temperature of the amplification product, and comparing the melting temperature to the melting temperature of a corresponding nucleotide sequence of SEQ ID NO:1. The melting temperature can be determined, for example, using denaturing high performance liquid chromatography.

Where a nested amplification is to be performed, the method can include a step directed to reducing contamination of the PKD1-specific amplification product by genomic DNA prior to contacting the PKD1-specific amplification product with the at least second set of primer pairs. For example, contamination of the PKD1-specific amplification product can be reduced by diluting the PKD1-specific amplification product.

The mutation indicative of a of PKD1 associated disorder can be, for example, a nucleotide sequence substantially identical to SEQ ID NO:1, wherein nucleotide 3110 is a C; nucleotide 8298 is a G; nucleotide 9164 is a G; nucleotide 9213 is an A; nucleotide 9326 is a T; or nucleotide 10064 is an A; or can be a nucleotide sequence substantially identical to SEQ ID NO:1, wherein nucleotide 3336 is deleted; nucleotide 3707 is an A; nucleotide 5168 is a T; nucleotide 6078 is an A; nucleotide 6089 is a T; nucleotide 6326 is a T; nucleotides 7205 to 7211 are deleted; nucleotide 7415 is a T; nucleotide 7433 is a T; nucleotide 7883 is a T; or nucleotides 8159 to 8160 are deleted; or wherein a GCG nucleotide sequence is inserted between nucleotides 7535 and 7536.

Data that is collected pursuant to a step of detecting the presence or absence of a mutation indicative of a PKD1-associated disorder in an amplification product, which can be an amplification product generated according to a method of the invention, including, for example, a PKD1-specific amplification product or a nested amplification product, can be accumulated, and can be formatted into a form that facilitates determining, for example, whether a subject is at risk of a PKD1-associated disorder. As such, the data can be formatted into a report that indicates whether a subject is at risk of a PKD1-associate disorder. The report can be in any of various forms, including, for example, contained in a computer random access or read-only memory, or stored on a diskette, CD, DVD, magnetic tape; presented on a visual display such as a computer monitor or other cathode ray tube or liquid crystal display; or printed on paper. Furthermore, the data, which can be formatted into a report, can be transmitted to a user interested in or privy to the information. The data or report can be transmitted using any convenient medium, for example, via the internet, by facsimile or by mail, depending on the form of the data or report.

Also provided is a method of detecting the presence of a mutant PKD1 polynucleotide in a sample by contacting a sample suspected of containing a mutant PKD1 polynucleotide with an oligonucleotide of the invention under conditions that allow the oligonucleotide to selectively hybridize with a mutant PKD1 polynucleotide; and detecting selective hybridization of the oligonucleotide and a mutant PKD1 polynucleotide, thereby detecting the presence of a mutant PKD1 polynucleotide sequence in the sample. In another embodiment, a method of detecting the presence of a mutant PKD1 polypeptide in a sample is provided, for example, by contacting a sample suspected of containing a mutant PKD1 polypeptide with an antibody of the invention under conditions that allow the antibody to specifically bind a mutant PKD1 polypeptide; and detecting specific binding of the antibody and the mutant PKD1 polypeptide in the sample, thereby detecting the presence of a mutant PKD1 polypeptide in a sample. The mutant PKD1 polypeptide can have a sequence, for example, substantially as set forth in SEQ ID NO:2, and having a mutation of A88V, W967R, L2696R, R2985G, W3001X, R3039C, V3285I, H3311R, or a combination thereof (see, also, Table 4).

Antibodies that can specifically bind wild type or mutant PKD1 polypeptides, or peptide portions thereof, can also be used as ADPKD diagnostic reagents. Such reagents provide a diagnostic method that can detect the expression of abnormal PKD1 proteins or of abnormal levels of PKD1 protein expression, including the detection of mutant PKD1 polypeptides or aberrant cellular localization of a PKD1 protein. For example, differences in the size, electronegativity, or antigenicity of the mutant PKD1 protein relative to a wild type PKD1 protein can be detected.

Diagnostic methods for the detection of mutant PKD1 polypeptides or peptide portions thereof can involve, for example, immunoassays wherein epitopes of a mutant PKD1 polypeptide are detected by their interaction with an anti-PKD1 specific antibody (e.g., an anti-mutant PKD1 specific antibody). For example, an antibody that specifically binds to a mutant PKD1 polypeptide does not bind to a wild-type PKD1 polypeptide or peptide thereof. Particular epitopes of PKD1 to which antibodies can be developed include peptides that are substantially identical to SEQ ID NO:2, and having at least five amino acids, including amino acid residue 88, wherein residue 88 is a V; residue 967, wherein residue 967 is an R; residue 2696, wherein residue 2696 is an R; residue 2985, wherein residue 2985 is a G; residue 3039, wherein residue 3039 is a C; residue 3285, wherein residue 3285 is an I; or residue 3311, wherein residue 3311 is an R; or a C-terminal peptide including amino acid residue 3000, where residue 3001 is absent and the mutant PKD1 polypeptide is truncated due to the presence of a STOP codon in the encoding mutant PKD1 polynucleotide.

Antibodies, or fragments of antibodies, such as those described, above, are useful in the present invention and can be used to quantitatively or qualitatively detect the presence of wild type or mutant PKD1 polypeptides or peptide portions thereof, for example. This can be accomplished, for example, by immunofluorescence techniques employing a fluorescently labeled antibody (see below) coupled with light microscopic, flow cytometric, or fluorimetric detection.

The antibodies (or fragments thereof) useful in the present invention can, additionally, be employed histologically, as in immunofluorescence or immunoelectron microscopy, for in situ detection of PKD1 polypeptide, peptides, variants or mutants thereof. Detection can be accomplished by removing a histological specimen from a subject, and applying thereto a labeled antibody of the present invention. The histological sample can be taken from a tissue suspected of exhibiting ADPKD. The antibody (or fragment) is preferably applied by overlaying the labeled antibody (or fragment) onto a biological sample. Through the use of such a procedure, it is possible to determine not only the presence of PKD1 polypeptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant PKD1 polypeptide or peptide portions thereof typically comprise incubating a biological sample, such as a biological fluid, a tissue extract, freshly harvested cells, or cells that have been incubated in tissue culture, in the presence of a detectably labeled antibody capable of identifying a PKD1 polypeptide, mutant PKD1 polypeptide and peptide portions thereof, and detecting the bound antibody by any of a number of techniques well-known in the art. The biological sample can be brought in contact with and immobilized onto a solid phase support or carrier such as nitrocellulose, or other solid support that is capable of immobilizing cells, cell particles or soluble proteins. The support can then be washed with suitable buffers followed by treatment with the detectably labeled mutant PKD1 specific antibody, preferably an antibody that recognizes a developed include peptides that are substantially identical to SEQ ID NO:2, and having at least five amino acids, including amino acid residue 88, wherein residue 88 is a V; residue 967, wherein residue 967 is an R; residue 2696, wherein residue 2696 is an R; residue 2985, wherein residue 2985 is a G; residue 3039, wherein residue 3039 is a C; residue 3285, wherein residue 3285 is an I; or residue 3311, wherein residue 3311 is an R; or a C-terminal peptide including amino acid residue 3000, where residue 3001 is absent and the mutant PKD1 polypeptide is truncated due to the presence of a STOP codon in the encoding mutant PKD1 polynucleotide (see, also, Table 4). The solid phase support can then be washed with the buffer a second time to remove unbound antibody, and the amount of bound label on solid support can be detected by conventional means specific for the label.

A "solid phase support" or "carrier" can be any support capable of binding an antigen or an antibody. Well-known supports or carriers include glass, polystyrene, polypropylene, polyethylene, dextran, nylon, amylases, natural and modified celluloses, polyacrylamides, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, or the like. Those skilled in the art will know many other suitable carriers for binding antibody or antigen, or will be able to ascertain the same by use of routine experimentation.

The binding activity of a given lot of an anti-mutant PKD1 antibody can be determined according to well known methods. Those skilled in the art will be able to determine operative and optimal assay conditions for each determination by employing routine experimentation. One of the ways in which the mutant PKD1-specific antibody can be detectably labeled is by linking the antibody to an enzyme and use the enzyme labeled antibody in an enzyme immunoassay (EIA; Voller, "The Enzyme Linked Immunosorbent Assay (ELISA): Diagnostic Horizons 2:1-7, 1978; Microbiological Associates Quarterly Publication, Walkersville, Md.); Voller et al., J. Clin. Pathol. 31:507-520, 1978; Butler, Meth. Enzymol. 73:482-523, 1981; Maggio (ed.), "Enzyme Immunoassay", CRC Press, Boca Raton Fla., 1980; Ishikawa et al., (eds.), "Enzyme Immunoassay", Kgaku Shoin, Tokyo, 1981). The enzyme that is bound to the antibody will react with an appropriate substrate, preferably a chromogenic substrate, in such a manner as to produce a chemical moiety that can be detected, for example, by spectrophotometric, fluorimetric or by visual means.

Enzymes that can be used to detectably label the antibody include, but are not limited to, malate dehydrogenase, staphylococcal nuclease, delta-5-steroid isomerase, yeast alcohol dehydrogenase, 1-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection can also be accomplished by visual comparison of the extent of enzymatic reaction of a substrate in comparison with similarly prepared standards. In addition, detection can be accomplished using any of a variety of other immunoassays, including, for example, by radioactively labeling the antibodies or antibody fragments and detecting PKD1 wild type or mutant peptides using a radioimmunoassay (RIA; see, for example, Weintraub, Principles of Radioimmunoassays, Seventh Training Course on Radioligand Assay Techniques, The Endocrine Society, March, 1986, which is incorporated herein by reference). The radioactive isotope can be detected by such means as the use of a gamma counter or a scintillation counter or by autoradiography.

The antibody also can be labeled with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In vitro systems can be designed to identify compounds capable of binding a mutant PKD1 polynucleotide of the invention (e.g., a polynucleotide having a sequence substantially identical to SEQ ID NO:1 and having a mutation such as C474T; G487A; T3110C; T8298G; A9164G; G9213A; C9326T; C9367T; G10064A; A10143G; T10234C; or G10255T). Such compounds can include, but are not limited to, peptides made of D- and/or L-configuration amino acids in, for example, the form of random peptide libraries (see, e.g., Lam et al., Nature 354:82-84, 1981), phosphopeptides in, for example, the form of random or partially degenerate, directed phosphopeptide libraries (see, e.g., Songyang et al., Cell 72:767-778, 1993), antibodies, and small or large organic or inorganic molecules. Compounds identified can be useful, for example, in modulating the activity of PKD1 proteins, variants or mutants. For example, mutant PKD1 polypeptides of the invention can be useful in elaborating the biological function of the PKD1 protein. Such mutants can be utilized in screens for identifying compounds that disrupt normal PKD1 interactions, or can in themselves disrupt such interactions.

The principle of the assays used to identify compounds that bind to a mutant PKD1 protein involves preparing a reaction mixture of the PKD1 protein, which can be a mutant, including a variant, and the test compound under conditions and for a time sufficient to allow the two components to interact, then isolating the interaction product (complex) or detecting the complex in the reaction mixture. Such assays can be conducted in a heterogeneous or homogeneous format. Heterogeneous assays involve anchoring PKD1 or the test substance onto a solid phase and detecting PKD1 test substance complexes anchored on the solid phase at the end of the reaction. In homogeneous assays, the entire reaction is carried out in a liquid phase. In either approach, the order of addition of reactants can be varied to obtain different information about the compounds being tested.

In addition, methods suitable for detecting protein-protein interactions can be employed for identifying novel PKD1 cellular or extracellular protein interactions based upon the mutant or variant PKD1 polypeptides of the invention. For example, some traditional methods that can be employed are co-immunoprecipitation, crosslinking and copurification through gradients or chromatographic columns. Additionally, methods that result in the simultaneous identification of the genes coding for the protein interacting with a target protein can be employed. These methods include, for example, probing expression libraries with labeled target protein, using this protein in a manner similar to antibody probing of Egt libraries. One such method for detecting protein interactions in vivo is the yeast two hybrid system. One version of this system has been described (Chien et al., Proc. Natl. Acad. Sci. USA 88:9578-9582, 1991) and can be performed using commercially available reagents (Clontech; Palo Alto Calif.).

A PKD1 polypeptide (e.g., a variant or mutant) of the invention can interact with one or more cellular or extracellular proteins in vivo. Such cellular proteins are referred to herein as "binding partners". Compounds that disrupt such interactions can be useful in regulating the activity of a PKD1 polypeptide, especially mutant PKD1 polypeptides. Such compounds include, for example, molecules such as antibodies, peptides, peptidomimetics and the like.

In instances whereby ADPKD symptoms are associated with a mutation within the PKD1 polynucleotide (e.g., SEQ ID NO:1 having a mutation at T3110C; T8298G; A9164G; G9213A; C9326T; G10064A or the like; see Example 2), which produces PKD1 polypeptides having aberrant activity, compounds identified that disrupt such activity can therefore inhibit the aberrant PKD1 activity and reduce or treat ADPKD1-associated symptoms or ADPKD disease, respectively (see Table 4). For example, compounds can be identified that disrupt the interaction of mutant PKD1 polypeptides with cellular or extracellular proteins, for example, the PKD2 gene product, but do not substantially effect the interactions of the normal PKD1 protein. Such compounds can be identified by comparing the effectiveness of a compound to disrupt interactions in an assay containing normal PKD1 protein to that of an assay containing mutant PKD1 polypeptide, for example, a two hybrid assay.

The basic principle of the assay systems used to identify compounds that interfere with the interaction between the PKD1 protein, preferably a mutant PKD1 protein, and its cellular or extracellular protein binding partner or partners involves preparing a reaction mixture containing the PKD1 protein and the binding partner under conditions and for a time sufficient to allow the two proteins to interact or bind, thus forming a complex. In order to test a compound for inhibitory activity, reactions are conducted in the presence or absence of the test compound, i.e., the test compound can be initially included in the reaction mixture, or added at a time subsequent to the addition of PKD1 and its cellular or extracellular binding partner; controls are incubated without the test compound or with a placebo. The formation of any complexes between the PKD1 protein and the cellular or extracellular binding partner is then detected. The formation of a complex or interaction in the control reaction, but not in the reaction mixture containing the test compound indicates that the compound interferes with the interaction of the PKD1 protein and the binding partner. As noted above, complex formation or component interaction within reaction mixtures containing the test compound and normal PKD1 protein can also be compared to complex formation or component interaction within reaction mixtures containing the test compound and mutant PKD1 protein. This comparison can be important in those cases wherein it is desirable to identify compounds that disrupt interactions of mutant but not normal PKD1 proteins.

Any of the binding compounds, including but not limited to, compounds such as those identified in the foregoing assay systems can be tested for anti-ADPKD activity. ADPKD, an autosomal dominant disorder, can involve underexpression of a wild-type PKD1 allele, or expression of a PKD1 polypeptide that exhibits little or no PKD1 activity. In such an instance, even though the PKD1 polypeptide is present, the overall level of normal PKD1 polypeptide present is insufficient and leads to ADPKD symptoms. As such increase in the level of expression of the normal PKD1 polypeptide, to levels wherein ADPKD symptoms are ameliorated would be useful. Additionally, the term can refer to an increase in the level of normal PKD1 activity in the cell, to levels wherein ADPKD symptoms are ameliorated.

The identified compounds that inhibit PKD1 expression, synthesis and/or activity can be administered to a patient at therapeutically effective doses to treat polycystic kidney disease. A therapeutically effective dose refers to that amount of the compound sufficient to result in amelioration of symptoms of polycystic kidney disease. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography. Additional factors that can be utilized to optimize dosage can include, for example, such factors as the severity of the ADPKD symptoms as well as the age, weight and possible additional disorders that the patient can also exhibit. Those skilled in the art will be able to determine the appropriate dose based on the above factors.

Pharmaceutical compositions for use in accordance with the present invention can be formulated in conventional manner using one or more physiologically acceptable carriers or excipients. Thus, the compounds and their physiologically acceptable salts and solvates can be formulated for administration by inhalation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. For buccal administration the compositions can take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin, for use in an inhaler can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Alternatively, ADPKD can be caused by the production of an aberrant mutant form of the PKD1 protein, that either interferes with the normal allele product or introduces a novel function into the cell, which then leads to the mutant phenotype. For example, a mutant PKD1 protein can compete with the wild type protein for the binding of a substance required to relay a signal inside or outside of a cell.

Cell based and animal model based assays for the identification of compounds exhibiting anti-ADPKD activity are also encompassed within the present invention. Cells that contain and express mutant PKD1 polynucleotide sequences (e.g., a sequence substantially identical to the sequence as set forth in SEQ ID NO:1 and having one or more mutations of a C474T; G487A; T3110C; T8298G; A9164G; G9213A; C9326T; C9367T; G10064A; A10143G; T10234C; G10255T or the like; see Example 2), which encode a mutant PKD1 polypeptide, and thus exhibit cellular phenotypes associated with ADPKD, can be utilized to identify compounds that possess anti-ADPKD activity. Such cells can include cell lines consisting of naturally occurring or engineered cells that express mutant or express both normal and mutant PKD1 polypeptides. Such cells include, but are not limited to renal epithelial cells, including primary and immortalized human renal tubular cells, MDCK cells, LLPCK1 Cells, and human renal carcinoma cells. Methods of transforming cell with PKD1 polynucleotide sequences encoding wild-type or mutant proteins are described above.

Cells that exhibit ADPKD-like cellular phenotypes, can be exposed to a compound suspected of exhibiting anti-ADPKD activity at a sufficient concentration and for a time sufficient to elicit an anti-ADPKD1 activity in the exposed cells. After exposure, the cells are examined to determine whether one or more of the ADPKD-like cellular phenotypes has been altered to resemble a more wild type, non-ADPKD phenotype.

Among the cellular phenotypes that can be followed in the above assays are differences in the apical/basolateral distribution of membrane proteins. For example, normal (i.e., non-ADPKD) renal tubular cells in situ and in culture under defined conditions have a characteristic pattern of apical/basolateral distribution of cell surface markers. ADPKD renal cells, by contrast, exhibit a distribution pattern that reflects a partially reversed apical/basolateral polarity relative to the normal distribution. For example, sodium-potassium ATPase generally is found on the basolateral membranes of renal epithelial cells, but also can be found on the apical surface of ADPKD epithelial cells, both in cystic epithelia in vivo and in ADPKD cells in culture (Wilson et al., Am. J. Physiol. 260:F420-F430, 1991). Another marker that exhibits an alteration in polarity in normal versus ADPKD affected cells is the EGF receptor, which is normally located basolaterally, but in ADPKD cells is mislocated to the apical surface. Such a apical/basolateral marker distribution phenotype can be followed, for example, by standard immunohistology techniques using antibodies specific to a markers of interest.

Assays for the function of PKD1 also can include a measure of the rate of cell growth or apoptosis, since dysregulation of epithelial cell growth can be a key step in cyst formation. The cysts are fluid filled structures lined by epithelial cells that are both hyper-proliferative and hyper-apoptotic (Evan et al., Kidney International 16:743-750, 1979; Kovacs and Gomba, Kidney Blood Press. Res. 21:325-328, 1998; Lanoix et al., Oncogene 13: 1153-1160, 1996; Woo, New Engl. J. Med. 333:18-25, 1995, each of which is incorporated herein by reference). The cystic epithelium has a high mitotic rate in vivo as measured by PCNA staining (Nadasdy et al., J. Am. Soc. Nephrol. 5:1462-1468, 1995, which is incorporated herein by reference), and increased levels of expression of other markers of proliferation (Klingel et al., Amer. J. Kidney Dis. 19:22-30, 1992, which is incorporated herein by reference). In addition, cultured cells from ADPKD cystic kidneys have increased growth rates in vitro (Wilson et al., Kidney Int. 30:371-380, 1986. Wilson, Amer. J. Kidney Dis. 17:634-637, 1991, each of which is incorporated herein by reference).

Further, in studies of rodent models of polycystic kidney disease, the epithelial cells that line cysts of animals with naturally occurring forms of PKD showed abnormalities similar to those reported in human ADPKD (Harding et al., 1992; Ramasubbu et al., J. Am. Soc. Nephrol. 9:937-945, 1998; Rankin et al., J. Cell Physiol. 152:578-586, 1992; Rankin et al., In Vitro Cell Devel. Biol. Anim. 32:100-106, 1996, each of which is incorporated herein by reference). Moreover, mice that have transgenic overexpression of either c-myc or SV40-large T antigen developed PKD (Kelley et al. J. Am. Soc. Nephrol. 2:84-97, 1991; Trudel et al., Kidney Int. 39:665-671 1991, each of which is incorporated herein by reference). Also, expression of recombinant full length PKD1 in epithelial cells reduced their rate of growth and induced resistance to apoptosis when challenged with stimuli such as serum starvation or exposure to UV light, which are known to stimulate apoptosis (Boletta et al., Mol. Cell. 6:1267-1273, 2000, which is incorporated herein by reference). As such, biochemical pathways that are activated by PKD1 expression, including, for example, JAK2, STAT1/3, PI3 kinase, p21, and AKT, can provide surrogate markers for PKD1 activity.

The propensity of an epithelial cell to form tubules provides still another assay for the function of PKD1. In vivo, PKD is characterized by cystic transformation of renal tubules and pancreatic and biliary ductules. In vitro, expression of full length PKD1 induces spontaneous tubulogenesis in MDCK cells (Boletta et al., supra, 2000). In this model system, control MDCK cells, which did not express recombinant wild type full length PKD1, formed cystic structures unless treated with hepatocyte growth factor or with fibroblast conditioned medium when cultured suspended in collagen. In contrast, MDCK cells that expressed the full length wild type recombinant form of PKD1 spontaneously formed tubules in the absence of exogenous factors when cultured in this manner. As such, this model system can be used to identify ligands that bind to and activate the PKD1 protein, to determine pathways that are targeted for activation by therapeutic agents, and as an assay system to evaluate the effect of sequence variants on PKD1 function.

Additionally, assays for the function of a PKD1 polypeptide can, for example, include a measure of extracellular matrix (ECM) components, such as proteoglycans, laminin, fibronectin and the like, in that studies in both ADPKD and in rat models of acquired cystic disease (Carone et al., Kidney International 35:1034-1040, 1989) have shown alterations in such components. Thus, any compound that serves to create an extracellular matrix environment that more fully mimics the normal ECM should be considered as a candidate for testing for an ability to ameliorate ADPKD symptoms.

In addition, it is contemplated that the present invention can be used to measure the ability of a compound, such as those identified in the foregoing binding assays, to prevent or inhibit disease in animal models for ADPKD. Several naturally-occurring mutations for renal cystic disease have been found in animals, and are accepted in the art as models of ADPKD and provide test systems for assaying the effects of compounds that interact with PKD1 proteins. Of these models, the Han:SPRD rat model, provides an autosomal dominant model system (see, for example, Kaspareit-Rittinghausen et al., Vet. Path. 26:195, 1989), and several recessive models also are available (Reeders, Nature Genetics 1:235, 1992). In addition, knock-out mice, in which the PKD1 or PKD2 gene has been disrupted, are available and provide a relevant model system for genetic forms of ADPKD. As such, the PKD1 and PKD2 knock-out mice can be useful for confirming the effectiveness in vivo of compounds that interact with PKD1 proteins in vitro (see, for example, Wu et al., Nat. Genet. 24:75-78, 2000; Kim et al., Proc. Natl. Acad. Sci., USA 97:1731-1736, 2000; Lu et al., Nat. Genet. 21:160-161, 1999; Wu et al., Cell 93:177-188, 1998; Lu et al., Nat. Genet. 17:179-181, 1997, each of which is incorporated herein by reference).

Animal models exhibiting ADPKD-like symptoms associated with one or more of the mutant PKD1 polynucleotide sequences as disclosed herein can also be engineered by utilizing the PKD1 polynucleotide sequences such in conjunction with well known methods for producing transgenic animals. Animals of any species, including, but not limited to, mice, rats, rabbits, guinea pigs, pigs, mini-pigs, goats, and non-human primates, e.g., baboons, squirrels, monkeys, and chimpanzees can be used to generate such ADPKD animal models or transgenic animals. In instances where the PKD1 mutation leading to ADPKD symptoms causes a drop in the level of PKD1 protein or causes an ineffective PKD1 protein to be made (e.g., the PKD1 mutation is a dominant loss-of-function mutation, such as a W3001X, i.e., truncated after amino acid residue 3000, or a T3110C mutation; see, also, Table 4) various strategies can be utilized to generate animal models exhibiting ADPKD-like symptoms.

The present invention also provides transgenic non-human organisms, including invertebrates, vertebrates and mammals. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene integrated into the chromosomes of somatic cells.

Various methods to make the transgenic animals of the subject invention can be employed. Generally speaking, three such methods can be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191.

In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, the method of Love et al., (Biotechnology, 12, Jan. 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The non-human transgenic animals of the invention include, for example, bovine, porcine, ovine and avian animals (e.g., cow, pig, sheep, chicken, turkey). Such transgenic non-human animals are produced by introducing a transgene into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., Proc. Natl. Acad. Sci. USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal that includes exogenous genetic material within all of its cells. A transgenic animal can be produced by cross-breeding two chimeric animals that include exogenous genetic material within cells used in reproduction. Twenty-five percent of the resulting offspring will be transgenic i.e., animals that include the exogenous genetic material within all of their cells in both alleles. 50% of the resulting animals will include the exogenous genetic material within one allele and 25% will include no exogenous genetic material.

In the microinjection method useful in the practice of the invention, the transgene is digested and purified free from any vector DNA e.g. by gel electrophoresis. It is preferred that the transgene include an operatively associated promoter that interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionein, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken θ-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, Proc. Natl. Acad. Sci. USA 73:1260-1264, 1976). Efficient infection of the blastomeres is obtained by enzymatic treatment to remove the zona pellucida (Hogan et al., In "Manipulating the Mouse Embryo" (Cold Spring Harbor Laboratory Press, Cold Spring Harbor N.Y. 1986)). The viral vector system used to introduce the transgene is typically a replication-defective retro virus carrying the transgene (Jahner et al., Proc. Natl. Acad. Sci. USA 82:6927-6931, 1985; Van der Putten et al., Proc. Natl. Acad. Sci. USA 82:6148-6152, 1985). Transfection is easily and efficiently obtained by culturing the blastomeres on a monolayer of virus-producing cells (Van der Putten, supra; Stewart, et al., EMBO J. 6:383-388, 1987). Alternatively, infection can be performed at a later stage. Virus or virus-producing cells can be injected into the blastocoele (Jahner et al., Nature 298:623-628, 1982). Most of the founders will be mosaic for the transgene since incorporation occurs only in a subset of the cells that formed the transgenic nonhuman animal. Further, the founder can contain various retroviral insertions of the transgene at different positions in the genome that generally will segregate in the offspring. In addition, it is also possible to introduce transgenes into the germ line, albeit with low efficiency, by intrauterine retroviral infection of the midgestation embryo (Jahner et al., supra, 1982).

A third type of target cell for transgene introduction is the embryonal stem cell (ES). ES cells are obtained from pre-implantation embryos cultured in vitro and fused with embryos (Evans et al. Nature 292:154-156, 1981; Bradley et al., Nature 309:255-258, 1984; Gossler et al., Proc. Natl. Acad. Sci. USA 83:9065-9069, 1986; and Robertson et al., Nature 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal (for review see Jaenisch, Science 240:1468-1474, 1988).

The transgene can be any piece of DNA that is inserted by artifice into a cell, and becomes part of the genome of the organism (i.e., either stably integrated or as a stable extra-chromosomal element) that develops from that cell. Such a transgene can include a gene that is partly or entirely heterologous (i.e., foreign) to the transgenic organism, or can represent a gene homologous to an endogenous gene of the organism. Included within this definition is a transgene created by the providing of an RNA sequence that is transcribed into DNA, then incorporated into the genome. The transgenes of the invention include DNA sequences that encode a mutant PKD1 polypeptide, for example, a polypeptide having an amino acid sequence substantially identical to SEQ ID NO:2 and having a mutation of a A88V, a W967R, a L2696R, an R2985G, an R3039C, a V3285I, a H3311R, or any combination thereof; or encoding a truncated PKD1 polypeptide ending at amino acid 3000 (also referred to herein as "W3001X", where "X" indicates STOP codon; see, also, Table 4) and include sense, antisense, and dominant negative encoding polynucleotides, which can be expressed in a transgenic non-human animal. The term "transgenic" as used herein also includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete or partial loss of function that has been achieved by any transgenic technology familiar to those in the art. In one embodiment, transgenic animals having a gene knockout are those in which the target gene has been rendered nonfunctional by an insertion targeted to the gene to be rendered non-functional by homologous recombination.

The invention also includes animals having heterozygous mutations in or partial inhibition of function or expression of a PKD1 polypeptide. One of skill in the art would readily be able to determine if a particular mutation or if an antisense molecule was able to partially inhibit PKD1 expression. For example, in vitro testing can be desirable initially by comparison with wild-type (e.g., comparison of northern blots to examine a decrease in expression). After an embryo has been microinjected, colonized with transfected embryonic stem cells or infected with a retrovirus containing the transgene (except for practice of the subject invention in avian species, which is addressed elsewhere herein), the embryo is implanted into the oviduct of a pseudopregnant female. The progeny are tested for incorporation of the transgene by Southern blot analysis of blood samples using transgene specific probes. PCR is particularly useful in this regard. Positive progeny ($P_0$) are crossbred to produce offspring ($P_1$) that are analyzed for transgene expression by northern blot analysis of tissue samples.

In order to distinguish expression of like species transgenes from expression of an endogenous PKD1-related gene, a marker gene fragment can be included in the construct in the 3' untranslated region of the transgene and the northern blot probe designed to probe for the marker gene fragment. The serum levels of a PKD1 polypeptide can also be measured in the transgenic animal to determine the level of PKD1 expression. A method of creating a transgenic organism also can include methods of inserting a transgene into, for example, an embryo of an already created transgenic organism, the organism being transgenic for a different unrelated gene or polypeptide.

Transgenic organisms of the invention are highly useful in the production of organisms for study of, for example, polycystic kidney disease or PKD1-related diseases or disorders and in identifying agents or drugs that inhibit or modulate polycystic kidney disease, PKD1 associated disorders and inheritance. Expression of a mutant human PKD1 polynucleotide can be assayed, for example, by standard northern blot analysis, and the production of the mutant human PKD1 polypeptide can be assayed, for example, by detecting its presence using an antibody directed against the mutant human PKD1 polypeptide. Those animals found to express the mutant human PKD1 polypeptide can then be observed for the development of ADPKD-like symptoms.

As discussed above, animal models of ADPKD can be produced by engineering animals containing mutations in a copy of an endogenous PKD1 gene that correspond to mutations within the human PKD1 polynucleotide. Utilizing such a strategy, a PKD1 homologue can be identified and cloned from the animal of interest, using techniques such as those described herein. One or more mutations can be engineered into such a PKD1 homologue that correspond to mutations within the human PKD1 polynucleotide, as discussed above (e.g., resulting in a mutation of the amino acid sequence as set forth in SEQ ID NO:2 and having a mutation of a A88V, a W967R, a L2696R, an R2985G, a W3001X, an R3039C, a V3285I, a H3311R, or any combination thereof; see, also, Table 4). As disclosed herein, a mutant polypeptide produced by such an engineered corresponding PKD1 homologue can exhibit an aberrant PKD1 activity that is substantially similar to that exhibited by a mutant human PKD1 protein. The engineered PKD1 homologue can then be introduced into the genome of the animal of interest, using techniques such as those described, above. Accordingly, any of the ADPKD animal models described herein can be used to test compounds for an ability to ameliorate ADPKD symptoms, including those associated with the expression of a mutant PKD1 polypeptide substantially identical to SEQ ID NO:2 and having the mutation A88V, W967R, L2696R, R2985G, W3001X, R3039C, V3285I, H3311R, or a combination thereof (see Example 2 and Table 4).

As discussed above, mutations in the PKD1 polynucleotide that cause ADPKD can produce a form of the PKD1 protein that exhibits an aberrant activity that leads to the formation of ADPKD symptoms. A variety of techniques can be utilized to inhibit the expression, synthesis, or activity of such mutant PKD1 polynucleotides and polypeptides. For example, compounds such as those identified through assays described, above, which exhibit inhibitory activity, can be used in accordance with the invention to ameliorate ADPKD symptoms. Such molecules can include, but are not limited, to small and large organic molecules, peptides, and antibodies. Further, antisense and ribozyme molecules that inhibit expression of a PKD1 polynucleotide, (e.g., a mutant PKD1 polynucleotide), can also be used to inhibit the aberrant PKD1 activity. Such techniques are described, below. In yet another embodiment, triple helix molecules can be utilized in inhibiting aberrant PKD1 activity.

Among the compounds that can exhibit anti-ADPKD activity are antisense, ribozyme, and triple helix molecules. Such molecules can be designed to reduce or inhibit mutant PKD1 activity by modulating the expression or synthesis of PKD1 polypeptides. Techniques for the production and use of such molecules are well known to those of skill in the art.

Double stranded interfering RNA molecules are especially useful to inhibit expression of a target gene. For example, double stranded RNA molecules can be injected into a target cell or organism to inhibit expression of a gene and the resultant polypeptide's activity. It has been found that such double stranded RNA molecules are more effective at inhibiting expression than either RNA strand alone (Fire et al., Nature, 19:391 (6669): 806-11, 1998).

When a disorder is associated with abnormal expression of a PKD1 polypeptide (e.g., overexpression, or expression of a mutated form of the protein), a therapeutic approach that directly interferes with the translation of a PKD1 polypeptide (e.g., a wild type, variant or mutant PKD1 polypeptide) is possible. Alternatively, similar methodology can be used to study gene activity. For example, antisense nucleic acid, double stranded interfering RNA or ribozymes could be used to bind to a PKD1 mRNA sequence or to cleave it. Antisense RNA or DNA molecules bind specifically with a targeted gene's RNA message, interrupting the expression of that gene's protein product. The antisense binds to the messenger RNA forming a double stranded molecule that cannot be translated by the cell. Antisense oligonucleotides of about 15 to 25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of at least about 15 nucleotides also are preferred because they are less likely to cause problems when introduced into the target PKD1 polypeptide producing cell. The use of antisense methods to inhibit the in vitro translation of genes is well known in the art (Marcus-Sakura, Anal. Biochem., 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher et al., Antisense Res. and Devel., 1:227, 1991; Helene, Anticancer Drug Design, 6:569, 1991).

Ribozymes are RNA molecules possessing the ability to specifically cleave other single-stranded RNA in a manner analogous to DNA restriction endonucleases. Through the modification of nucleotide sequences that encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences that are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences. These and other uses of antisense and ribozymes methods to inhibit the in vivo translation of genes are known in the art (e.g., De Mesmaeker et al., Curr. Opin. Struct. Biol., 5:343, 1995; Gewirtz et al., Proc. Natl. Acad. Sci. USA, 93:3161, 1996b; Stein, Chem. and Biol. 3:319, 1996).

Specific ribozyme cleavage sites within any potential RNA target are initially identified by scanning the target molecule for ribozyme cleavage sites, which include the following sequence: GUA, GUU and GUC. Once identified, short RNA sequences of about 15 to 30 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using ribonuclease protection assays.

It is possible that the antisense, ribozyme, or triple helix molecules described herein can reduce or inhibit the translation of mRNA produced by mutant PKD1 alleles of the invention. In order to ensure that substantial normal levels of PKD1 activity are maintained in the cell, nucleic acid molecules that encode and express PKD1 polypeptides exhibiting normal PKD1 activity can be introduced into cells that do not contain sequences susceptible to whatever antisense, ribozyme, or triple helix treatments. Such sequences can be introduced via gene therapy methods such as those described, below. Alternatively, it can be preferable to coadminister normal PKD1 protein into the cell or tissue in order to maintain the requisite level of cellular or tissue PKD1 activity.

Antisense RNA and DNA molecules, ribozyme molecules and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well known modifications to the DNA molecules can be introduced as a means of increasing intracellular stability and half-life. Possible modifications include, but are not limited to, the addition of flanking sequences of ribonucleotide or deoxyribonucleotides to the 5' or 3' end or both of the molecule or the use of phosphorothioate or 2'-O-methyl rather than phosphodiesterase linkages within the oligodeoxyribonucleotide backbone.

As discussed above, mutations in the PKD1 polynucleotide that cause ADPKD can lower the level of expression of the PKD1 polynucleotide or; alternatively, can cause inactive or substantially inactive PKD1 proteins to be produced. In either instance, the result is an overall lower level of normal PKD1 activity in the tissues or cells in which PKD1 is normally expressed. This lower level of PKD1 activity, then, leads to ADPKD symptoms. Thus, such PKD1 mutations represent dominant loss-of-function mutations. For example, a polynucleotide having a sequence as set forth in SEQ ID NO:1 and having a mutation of a G9213A results in early termination of PKD1.

For example, normal PKD1 protein, at a level sufficient to ameliorate ADPKD symptoms can be administered to a patient exhibiting such symptoms or having a mutant PKD1 polynucleotide. Additionally, DNA sequences encoding normal PKD1 protein can be directly administered to a patient exhibiting ADPKD symptoms or administered to prevent or reduce ADPKD symptoms where they have been diagnosed as having a PKD1 mutation identified herein but have not yet demonstrated symptoms. Such administration can be at a concentration sufficient to produce a level of PKD1 protein such that ADPKD symptoms are ameliorated.

Further, subjects with these types of mutations can be treated by gene replacement therapy. A copy of the normal PKD1 polynucleotide can be inserted into cells, renal cells, for example, using viral or non-viral vectors that include, but are not limited to vectors derived from, for example, retroviruses, vaccinia virus, adeno-associated virus, herpes viruses, bovine papilloma virus or non-viral vectors, such as plasmids. In addition, techniques frequently employed by those skilled in the art for introducing DNA into mammalian cells can be utilized. For example, methods including but not limited to electroporation, DEAE-dextran mediated DNA transfer, DNA guns, liposomes, direct injection, and the like can be utilized to transfer recombinant vectors into host cells. Alternatively, the DNA can be transferred into cells through conjugation to proteins that are normally targeted to the inside of a cell. For example, the DNA can be conjugated to viral proteins that normally target viral particles into the targeted host cell.

Administering the whole gene or polypeptide is not necessary to avoid the appearance of ADPKD symptoms. The use of a "minigene" therapy approach also can serve to ameliorate such ADPKD symptoms (see Ragot et al., Nature 3:647, 1993; Dunckley et al., Hum. Mol. Genet. 2:717-723, 1993). A minigene system uses a portion of the PKD1 Coding region that encodes a partial, yet active or substantially active PKD1 polypeptide. As used herein, "substantially active" means that the polypeptide serves to ameliorate ADPKD symptoms. Thus, the minigene system utilizes only that portion of the normal PKD1 polynucleotide that encodes a portion of the PKD1 polypeptide capable of ameliorating ADPKD symptoms, and can, therefore represent an effective and even more efficient ADPKD therapy than full-length gene therapy approaches. Such a minigene can be inserted into cells and utilized via the procedures described, above, for full-length gene replacement. The cells into which the PKD1 minigene are to be introduced are, preferably, those cells, such as renal cells, which are affected by ADPKD. Alternatively, any suitable cell can be transfected with a PKD1 minigene so long as the minigene is expressed in a sustained, stable fashion and produces a polypeptide that ameliorates ADPKD symptoms.

A therapeutic minigene for the amelioration of ADPKD symptoms can comprise a nucleotide sequence that encodes at least one PKD1 polypeptide peptide domain, particularly a domain having an amino acid sequence substantially identical to a peptide portion SEQ ID NO:2 and having a mutation as shown in Table 4, for example, an A88V, W967R, L2696R, R2985G, W3001X, R3039C, V3285I, or H3311R mutation. Minigenes that encode such PKD1 polypeptides can be synthesized and/or engineered using the PKD1 polynucleotide sequence (SEQ ID NO:1).

The materials for use in the assay of the invention are ideally suited for the preparation of a kit. Such a kit can comprise a carrier means containing one or more container means such as vials, tubes, and the like, each of the container means comprising one of the separate elements to be used in the method. One of the container means can comprise a probe that is or can be detectably labeled. Such probe can be an oligonucleotide comprising at least 10 contiguous nucleotides and having a sequence of a fragment of SEQ ID NO:1 including: nucleotide 474, wherein nucleotide 474 is a T; nucleotide 487, wherein nucleotide 487 is an A; nucleotide 3110, wherein nucleotide 3110 is a C; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T (see, also, Example 2).

A kit containing one or more oligonucleotide probes of the invention can be useful, for example, for qualitatively identifying the presence of mutant PKD1 polynucleotide sequences in a sample, as well as for quantifying the degree of binding of the probe for determining the occurrence of specific strongly binding (hybridizing) sequences, thus indicating the likelihood for a subject having or predisposed to a disorder associated with PKD1. Where the kit utilizes nucleic acid hybridization to detect the target nucleic acid, the kit can also have containers containing reagents for amplification of the target nucleic acid sequence. When it is desirable to amplify the mutant target sequence, this can be accomplished using oligonucleotide primers, which are based upon identification of the flanking regions contiguous with the target nucleotide sequence. For example, primers such as those listed below in Tables 1 and 2 can be included in the kits of the invention. The kit can also contain a container comprising a reporter means such as an enzymatic, fluorescent, or radionuclide label, which can be bound to or incorporated into the oligonucleotide and can facilitate identification of the oligonucleotide.

The following examples are intended to illustrate but not limit the invention.

EXAMPLES

The present invention is based upon the use of widely spaced PKD1-specific anchor primers in long range PCR to generate 5 kb to 10 kb PKD1 polynucleotide segments. After appropriate dilution, the PCR products can be used as a template for mutation screening using any one of a variety of methods. Accordingly, a number of mutants have been identified in families with PKD1-associated disorders.

Using a number of PKD1-specific primers, eight templates ranging in size from about 0.3 to 5.8 kb were generated that span from the 5' untranslated region to intron 34 and cover all exons in the replicated region including exon 1 and exon 22 (Example 1). These reagents were used to evaluate 47 Asian PKD1 families (Example 2). Variant nucleotide sequences were found throughout the PKD1 polynucleotide sequence.

Forty-one That and 6 Korean ADPKD families were studied. Samples from 50 healthy That blood donors collected in blood banks served as normal controls. Genomic DNA was extracted from either fresh or frozen whole blood that had been stored for up to five years using commercially available kits (Puregene, Gentra) or standard phenol-chloroform methods. For the N23HA and 145.19 cell lines (Cell 77:881-894, 1994; Germino et al., Am J. Hum. Genet. 46:925-933, 1990; Ceccherini et al., Proc. Natl. Acad. Sci. USA 89:104-108, 1992, each of which is incorporated herein by reference; see, also, Watnick et al., supra, 1997), genomic DNA was isolated using the Puregene DNA isolation kit.

Example 1

Long Range Specific Templates

A two-part strategy was used to generate and validate PKD1-specific primers that could be used to amplify the replicated portion of PKD1. The sequence of PKD1 (SEQ ID NO:1) was aligned with that of two homologues present in GenBank (Accession Number AC002039) and identified potential sequence differences. Candidate primers were designed such that the mismatches were positioned at or adjacent to the 3' end of the oligonucleotide so as to maximize their specificity for PKD1.

Figure 2:
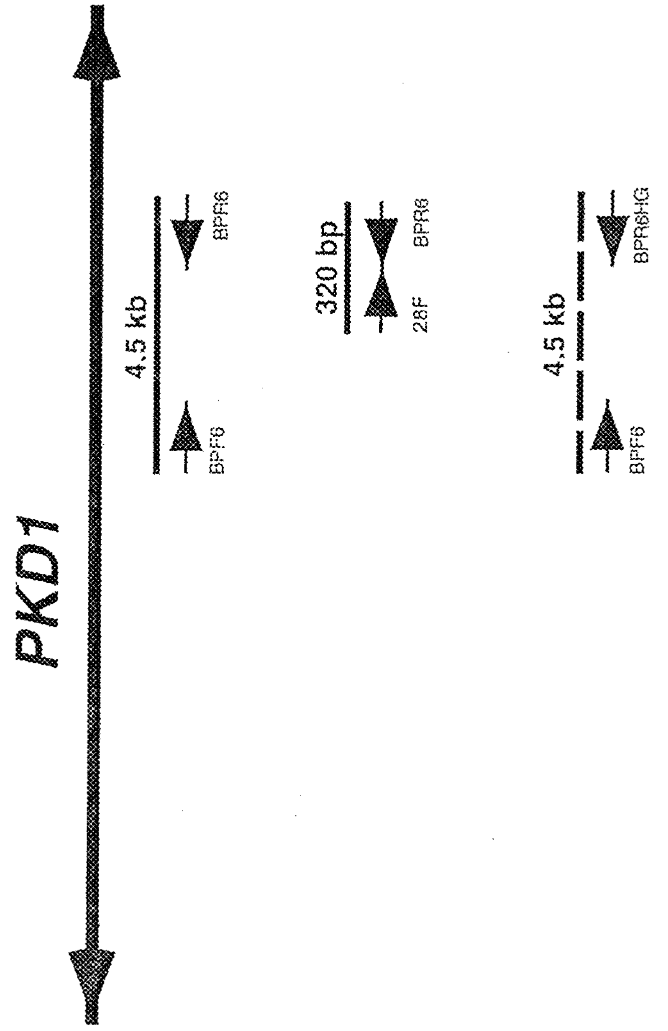
FIG. 2 shows the relative position of the BPF6-BPR6 long-range PCR template and the much shorter PKD1-specific exon 28 product, 28F-BPR6. The dashed line below exon 28 identified the long range PCR amplification product that resulted when BPF6, the sequence of which is common to the PKD1 gene and to the homologs, was used in combination with the homolog-specific primer, BPR6HG.

The primers were tested for specificity using rodent-human somatic cell hybrids that either contained only human 16p13.3 and therefore, human PKD1 (145.19, a radiation hybrid), or that lacked 16p13.3 and contained only the human PKD1-homologues (N23HA). FIG. 2 presents a representative example of this approach using the primer pair, BPF6 and the PKD1-specific primer BPR6. This primer pair amplified a product of the correct length (4.5 kb) under the stated conditions only when total human genomic DNA or 145.19 DNA is used as template. Similar results were obtained when BPR6 was used in combination with the non-specific primer 28F to generate a much shorter product.

As a final control, the absence of amplified product was verified using N23HA as template to confirm that the results obtained using total human genomic DNA and 145.19 DNA were due to the specificity of the primer and not the result of other causes (i.e., difference in quality of DNA or ratio of human/rodent template). A primer specific for the homologues (BPR6HG) was designed that was positioned the same distance from BPF6 as BPR6 and used to amplify a specific band of the same size as the corresponding PKD1-long range product. As predicted, a product of the correct size was amplified from both N23HA and total genomic DNA, but not from 145.19.

A total of eight primer pairs can be used to generate a series of templates that range in size from about 0.3 kb to 5.8 kb and include all exons and their flanking intron sequences in the replicated portion of PKD1 (exons 1 to 34). Table 1 summarizes the details for each product and includes the sequence of each primer, its respective position within the gene, its expected size, and the optimal annealing temperature and extension time for its amplification. FIG. 1 illustrates the relative position of each product with respect to the overall gene structure. It should be noted that exon 1 and its flanking sequences were particularly problematic to evaluate. Primer design was greatly limited by the high degree of homology and extreme GC bias in the region. A combination of widely space primers (to generate a fragment considerably larger than the segment of interest) and the GC melt system were used to circumvent these obstacles.

Specific details concerning the primer sequences, annealing temperatures and extension times used for each long-range (LR) template are provided in Table 1 (all sequences in Tables 1 and 2 are shown in 5' to 3' orientation from left to right). Three hundred to 400 ng of genomic DNA was used as template for each LR product, except for exon 1 (see below). The long range PCR amplification was performed as follows in a Perkin Elmer 9600 thermal cycler: denaturation at 95° C. for 3 min followed by 35 cycles of a two-step protocol that included denaturation at 95° C. for 20 sec followed by annealing and extension at a temperature and for a time specific for each primer pair (Table 1). A final extension at 72° C. for 10 min was included in each program. The total PCR volume was 50 Tl using 4 U of rTth DNA polymerase XL (Cetus, Perkin Elmer) and a final $MgOAC_2$ Concentration of 0.9 mM. A hot start protocol as recommended by the manufacturer was used for the first cycle of amplification. For the exon 1 LR product (Tl), the LR was generated using 500 ng of genomic DNA. The long range PCR amplification was modified as follows: denaturation 95° C. for 1 min followed by 35 two-step cycles of denaturation at 95° C. for 30 sec followed by annealing and extension at 69° C. for 7 min. The total PCR volume was 50 Tl using 1 Tl of Advantage-GC genomic polymerase (Clontech), GC melt of 1.5 M and final $MgOAC_2$ concentration of 1.1 mM.

TABLE 1

Oligonucleotide Primers for Long-Range Specific Templates from Exon 1-34 of PKD1 Gene

| Template | Primers | Sequence 5'□3' | Position (5') | Size (kb) | Tm (° C.) | ET (Min) | SEQ ID NO: |
|---|---|---|---|---|---|---|---|
| T1 | BPF14* | CCATCCACCTGCTGTGTGACCTGGTAAAT | 2043 | 2.2 | 69 | 7 | 3 |
| | BPR9 | CCACCTCATCGCCCCTTCCTAAGCAT | 4290 | | | | 4 |

TABLE 1-continued

Oligonucleotide Primers for Long-Range Specific Templates from Exon 1-34 of PKD1 Gene

| Template | Primers | Sequence 5'□3' | Position (5') | Size (kb) | Tm (° C.) | ET (Min) | SEQ ID NO: |
|---|---|---|---|---|---|---|---|
| T2-7 | BPF9* | ATTTTTTGAGATGGAGCTTC ACTCTTGCAGG | 17907 | 4.6 | 68 | 7 | 5 |
| | BPR4 | CGCTCGGCAGGCCCCTAACC | 22489 | | | | 6 |
| T8-12 | BPF12 | CCGCCCCCAGGAGCCTAGAC G | 22218 | 4.2 | 68 | 7 | 7 |
| | BPR5* | CATCCTGTTCATCCGCTCCA CGGTTAC | 26363 | | | | 8 |
| T13-15 | F13 | TGGAGGGAGGGACGCCAATC | 26246 | 4.4 | 68 | 7 | 9 |
| | R27* | GTCAACGTGGGCCTCCAAGT | 30612 | | | | 10 |
| T15-21 | F26* | AGCGCAACTACTTGGAGGCC C | 30603 | 3.4 | 70 | 4.5 | 11 |
| | R2 | GCAGGGTGAGCAGGTGGGGC CATCCTAC | 33953 | | | | 12 |
| T22 | BPF15 | GAGGCTGTGGGGGTCCAGTC AAGTGG | 36815 | 0.3 | 72 | 1 | 13 |
| | BPR12* | AGGGAGGCAGAGGAAAGGGC CG**A**AC | 37136 | | | | 14 |
| T23-28 | BPF6 | CCCCGTCCTCCCCGTCCTTT TGTC | 37325 | 4.2 | 69 | 7 | 15 |
| | BPR6* | AAGCGCAAAAGGGCTGCGTC G | 41524 | | | | 16 |
| T29-34 | BPF13* | GGCCCTCCCTGCCTTCTAGG CG | 41504 | 5.8 | 68 | 8 | 17 |
| | KG8R25* | GTTGCAGCCAAGCCCATGTT A | 47316 | | | | 18 |

Tm-annealing temperature; ET-extension time; *PKD1-specific primer.
Bold type in BPR12 primer sequence identifies intentional replacement of C by A to enhance discrimination of PKD1 from homologs.

The long-range templates were serially diluted (1:$10^4$ or 1:$10^5$) to remove genomic contamination, then used as templates for nested PCR of 200-400 bp exonic fragments. A total of 17 new primer pairs were developed for exons 1-12 and exon 22. The sequences and PCR conditions for each new pair are summarized in Table 2. Primer sequences and PCR conditions for exons 13-21 and 23-34 are described in Watnick et al., Am. J. Hum. Genet. 65:1561-1571, 1999; and Watnick et al., Hum. Mol. Genet. 6:1473-1481; 1997, which are incorporated herein by reference. Intron based primers were positioned approximately 30-50 bp away from consensus splice sites. Exons larger than approximately 400 bp were split into overlapping fragments of less than or equal to 350 bp. Two T1 of diluted long range (LR) product was used as template for amplification of each exon. Single strand conformation analysis was performed using standard protocols. SSCA analysis was performed by use of 8% polyacrylamide gels with 5% glycerol added. The radiolabeled PCR products were diluted with loading buffer, were denatured by heating at 95° C. for 5 min, then were placed on ice prior to being loaded and run on the gel at room temperature. Gels were run at 400 V overnight, dried, and placed on X-Omat XAR film (Kodak) at room temperature. Aberrantly migrating bands detected by SSCA were cut from the gel and eluted into 100 Tl of sterile water overnight. The eluted products were re-amplified using the same set of primers, purified using Centricon-100 columns (Amicon) and then sequences.

TABLE 2

Nested Primers Used for Mutation Detection

| Exons | Primer | Primer Sequence 5'→3' | Fragment size (bp) | $T_m$ (° C.) | SEQ ID NO: |
|---|---|---|---|---|---|
| T1 | 1F1 | GGTCGCGCTGTGGCGAAGG | 328 | 67 | 19 |
| T1 | 1R1 | CGGCGGGCGGCATCGT | | | 20 |

TABLE 2-continued

Nested Primers Used for Mutation Detection

| Exons | Primer | Primer Sequence 5'→3' | Fragment size (bp) | $T_m$ (° C.) | SEQ ID NO: |
|---|---|---|---|---|---|
| T1 | 1F2 | ACGGCGGGGCCATGCG | 348 | 67 | 21 |
| T1 | 1R2 | GCGTCCTGGCCCGCGTCC | | | 22 |
| T2-7 | 2F | TTGGGGATGCTGGCAATGTG | 272 | 62 | 23 |
| T2-7 | 2R | GGGATTCGGCAAAGCTGATG | | | 24 |
| T2-7 | 3F | CCATCAGCTTTGCCGAATCC | 171 | 62 | 25 |
| T2-7 | 3R | AGGGCAGAAGGGATATTGGG | | | 26 |
| T2-7 | 4F | AGACCCTTCCCACCAGACCT | 299 | 62 | 27 |
| T2-7 | 4R | TGAGCCCTGCCCAGTGTCT | | | 28 |
| T2-7 | 5F1 | GAGCCAGGAGGAGCAGAACCC | 259 | 65 | 29 |
| T2-7 | 5R1 | AGAGGGACAGGCAGGCAAAGG | | | 30 |
| T2-7 | 5F2 | CCCAGCCCTCCAGTGCCT | 284 | 65 | 31 |
| T2-7 | 5R2 | CCCAGGCAGCACATAGCGAT | | | 32 |
| T2-7 | 5F3 | CCGAGGTGGATGCCGCTG | 294 | 65 | 33 |
| T2-7 | 5R3 | GAAGGGGAGTGGGCAGCAGAC | | | 34 |
| T2-7 | 6F | CACTGACCGTTGACACCCTCG | 281 | 65 | 35 |
| T2-7 | 6R | TGCCCCAGTGCTTCAGAGATC | | | 36 |
| T2-7 | 7F | GGAGTGCCCTGAGCCCCCT | 311 | 65 | 37 |
| T2-7 | 7R | CCCCTAACCACAGCCAGCG | | | 38 |
| T8-12 | 8F | TCTGTTCGTCCTGGTGTCCTG | 215 | 65 | 39 |
| T8-12 | 8R | GCAGGAGGGCAGGTTGTAGAA | | | 40 |
| T8-12 | 9F | GGTAGGGGGAGTCTGGGCTT | 253 | 65 | 41 |
| T8-12 | 9R | GAGGCCACCCCGAGTCC | | | 42 |
| T8-12 | 10F | GTTGGGCATCTCTGACGGTG | 364 | 65 | 43 |
| T8-12 | 10R | GGAAGGTGGCCTGAGGAGAT | | | 44 |
| T8-12 | 11F2 | GGGGTCCACGGGCCATG | 311 | 67 | 45 |
| T8-12 | 11R2 | AAGCCCAGCAGCACGGTGAG | | | 46 |
| T8-12 | 11midF | GCTTGCAGCCACGGAAC | 386 | 65 | 47 |
| T8-12 | 11midR | GCAGTGCTACCACTGAGAAC | | | 48 |
| T8-12 | 11F1 | TGCCCCTGGGAGACCAACGATAC | 303 | 67 | 49 |
| T8-12 | 11R1 | GGCTGCTGCCCTCACTGGGAAG | | | 50 |
| 12 | 12F | GAGGCGACAGGCTAAGGG | 286 | 64 | 51 |
| | 12R-2 | CATGAAGCAGAGCAGAAGG | | | 61 |
| 13 | 13F: | TGGAGGGAGGGACGCCAATC | 308 | 67 | 62 |
| | 13R: | GAGGCTGGGGCTGGGACAA | | | 63 |
| 14 | 14F: | CCCGGTTCACTCACTGCG | 220 | 64 | 64 |
| | 14R: | CCGTGCTCAGAGCCTGAAAG | | | 65 |
| 15 | 15F16: | CGGGTGGGGAGCAGGTGG | 280 | 67 | 66 |
| | 15R16: | GCTCTGGGTCAGGACAGGGGA | | | 67 |

TABLE 2-continued

| Nested Primers Used for Mutation Detection | | | | | |
|---|---|---|---|---|---|
| Exons | Primer | Primer Sequence 5'→3' | Fragment size (bp) | $T_m$ (° C.) | SEQ ID NO: |
| 15 | 15F15: | CGCCTGGGGGTGTTCTTT | 270 | 64 | 68 |
| | 15R15: | ACGTGATGTTGTCGCCCG | | | 69 |
| 15 | 15F14: | GCCCCCGTGGTGGTCAGC | 250 | 67 | 70 |
| | 15R14: | CAGGCTGCGTGGGGATGC | | | 71 |
| 15 | 15F13: | CTGGAGGTGCTGCGCGTT | 256 | 67 | 72 |
| | 15R13: | CTGGCTCCACGCAGATGC | | | 73 |
| 15 | 15F12: | CGTGAACAGGGCGCATTA | 270 | 65 | 74 |
| | 15R12: | GCAGCAGAGATGTTGTTGGAC | | | 75 |
| 15 | 15F11: | CCAGGCTCCTATCTTGTGACA | 259 | 60 | 76 |
| | 15R11: | TGAAGTCACCTGTGCTGTTGT | | | 77 |
| 15 | 15F10: | CTACCTGTGGGATCTGGGG | 217 | 67 | 78 |
| | 15R10: | TGCTGAAGCTCACGCTCC | | | 79 |
| 15 | 15F9: | GGGCTCGTCGTCAATGCAAG | 267 | 67 | 80 |
| | 15R9: | CACCACCTGCAGCCCCTCTA | | | 81 |
| 15 | 15F8: | 5CCGCCCAGGACAGCATCTTC | 261 | 64 | 82 |
| | 15R8: | CGCTGCCCAGCATGTTGG | | | 83 |
| 15 | 15F7: | CGGCAAAGGCTTCTCGCTC | 288 | 64 | 84 |
| | 15R7: | CCGGGTGTGGGGAAGCTATG | | | 85 |
| 15 | 15F6: | CGAGCCATTTACCACCCATAG | 231 | 65 | 86 |
| | 15R6: | GCCCAGCACCAGCTCACAT | | | 87 |
| 15 | 15F5: | CCACGGGCACCAATGTGAG | 251 | 64 | 88 |
| | 15R5: | GGCAGCCAGCAGGATCTGAA | | | 89 |
| 15 | 15F4: | CAGCAGCAAGGTGGTGGC | 333 | 67 | 90 |
| | 15R4: | GCGTAGGCGACCCGAGAG | | | 91 |
| 15 | 15F3: | ACGGGCACTGAGAGGAACTTC | 206 | 64 | 92 |
| | 15R3: | ACCAGCGTGCGGTTCTCACT | | | 93 |
| 15 | 15F2: | GCCGCGACGTCACCTACAC | 265 | 67 | 94 |
| | 15R2: | TCGGCCCTGGGCTCATCT | | | 95 |
| 15 | 15F1: | GTCGCCAGGGCAGGACACAG | 228 | 68 | 96 |
| | R27': | AGGTCAACGTGGGCCTCCAA | | | 113 |
| 15 | 15F1-1: | ACTTGGAGGCCCACGTTGACC | 276 | 69 | 97 |
| | 15R1-1: | TGATGGGCACCAGGCGCTC | | | 98 |

TABLE 2-continued

| Nested Primers Used for Mutation Detection | | | | | |
|---|---|---|---|---|---|
| Exons | Primer | Primer Sequence 5'→3' | Fragment size (bp) | $T_m$ (° C.) | SEQ ID NO: |
| 15 | 15F1-2: | CATCCAGGCCAATGTGACGGT | 266 | 64 | 99 |
| | 15R1-2: | CCTGGTGGCAAGCTGGGTGTT | | | 100 |
| 16 | 16F: | TAAAACTGGATGGGGCTCTC | 294 | 56 | 101 |
| | 16R: | GGCCTCCACCAGCACTAA | | | 102 |
| 17 | 17F: | GGGTCCCCCAGTCCTTCCAG | 244 | 67 | 103 |
| | 17R: | TCCCCAGCCCGCCCACA | | | 104 |
| 18 | 18F: | GCCCCCTCACCACCCCTTCT | 342 | 67 | 105 |
| | 18R: | TCCCGCTGCTCCCCCCAC | | | 106 |
| 19 | 19F: | GATGCCGTGGGGACCGTC | 285 | 67 | 107 |
| | 19R: | GTGAGCAGGTGGCAGTCTCG | | | 108 |
| 20 | 20F: | CCACCCCCTCTGCTCGTAGGT | 232 | 64 | 109 |
| | 20R: | GGTCCCAAGCACGCATGCA | | | 110 |
| 21 | 21F: | TGCCGGCCTCCTGCGCTGCTGA | 232 | 67 | 111 |
| | TWR2-1: | GTAGGATGGCCCCACCTGCTCAC CCTGC | | | 112 |

Variants that were predicted to alter a restriction site were confirmed by restriction enzyme digestion analysis of re-amplified products. In cases where the change did not alter a restriction site, primers were designed with mismatches that create a new restriction site when combined with the point mutation in question. The following primer combinations were utilized:

ASP1 + 26R
(ASP1; 5'-CTGGTGACCTACATGGTCATGGCC GAGATC-3'; SEQ ID NO: 55);

ASP2 + 30R
(ASP2; 5'-GGTTGTCTATCCCGTCTACCTGGCCCTCCT-3'; SEQ ID NO: 56);

ASP3 + 30F
(ASP3; 5'-GTCCCCAGCCCCAGCCCACCTGGCC-3'; SEQ ID NO: 57).

When possible, segregation of the variant with the disease phenotype was tested. In cases where a missense change was unable to be determined on the normal haplotype (and thus be a normal variant) the mutation was tested for in a panel of 50 normal controls.

Example 2

Mutation Screening

The new PKD1-specific products were generated from one affected member of each of the 47 Asian families and then used as template for mutation detection of exons 1-12 and 22-34. Table 2 (above) lists the sequence and PCR condition for primer pairs that were used for nested amplification of individual exons and their adjacent intronic sequence. Overlapping pairs were designed for segments>400 base pairs in length.

A total of 13 novel variants were detected by SSCA using the conditions described above. Two are highly likely to be pathogenic mutations, four are predicted to encode missense substitutions not found in normals and seven are normal variants (see Table 3).

The first pathogenic mutation is a G to A transition at position 9213 in exon 25 that is predicted to result in a nonsense codon (W3001X). Its presence was confirmed by restriction analysis using the enzyme Mae I and it was found to segregate with disease. This variant is predicted to truncate the protein near the carboxyl end of the Receptor for Egg Jelly (REJ) domain. The W3001X mutation results in a greatly truncated product missing all of the membrane spanning elements, intervening loops and carboxy terminus. The second mutation (T3110C) is predicted to result in a non-conservative amino acid substitution (W967R) at a critical position of one of the PKD repeats. The mutation is unique to the family in which it was found and was not observed in a screen of over 100 normal That chromosomes. The W967R missense mutation is predicted to disrupt the secondary structure of PKD domain 3. The WDFGDGS (SEQ ID NO:58) motif within the CC' loop region is the most conserved sequence of the PKD domains. The tryptophan is replaced is the first residue of the turn at the end of the C strand and is conserved in 14 out of 16 PKD domains. Moreover, it is evolutionarily conserved in mouse and Fugu polycystin-1.

TABLE 3

Mutations Identified in the PKD1 Gene in a Thai Population

| Patient | Exon | Nucleic Acid Change | Codon Change | Consequence | Confirmation Enzyme |
|---|---|---|---|---|---|
| Pathogenic | | | | | |
| RAMA28-01[0] | 12 | T3110C | W967R | Missense (disrupt PKD domain3) | BsaW 1 (cut NC) |
| RAMA59-02* | 25 | G9213A | W3001X | Nonsense (early termination) | Mae I |
| Variants not found in 100 chromosomes | | | | | |
| RAMA3-02* | 22 | T8298G | L2696R | Missense | HinP1 I |
| RAMA87-01* | 25 | A9164G | R2985G | Missense | BsrB 1 |
| RAMA87-01* | 25 | C9326T | R3039C | Missense | Fau I (cut NC) |
| RAMA45-03* | 29 | G10064A | V3285I | Missense | Bsm I |
| Probable normal variants | | | | | |
| RAMA7-06 | 2 | C474T | A88V | Missense | Hph I |
| RAMA107-01 | 2 | G487A | A92A | Silent change | TspR I |
| RAMA94-01 | 25 | C9367T | G3052G | Silent change | Sfo I (cut NC) |
| RAMA66-01 | 30 | A10143G[HG] | H3311R | Missense | Nsp I (cut NC) |
| RAMA66-01 | 30 | T10234C[HG] | L3341L | Silent change | ASP1 + BseR I |
| RAMA51-01 | 30 | G10255T | R3348R | Silent change | ASP2 + MSC I |

*Segregation with disease; [0]cannot test for segregation; NC—Normal control; HG—Present in one copy of the homologues; ASP—Allele-specific primer.

These pathogenic mutations add to previously identified pathogenic mutations, including a deletion of G3336 (−G3336) in exon 13, resulting in a frame shift after amino acid 1041 (FS1041); C4168T (Q1653)X), C6089T (Q1960X) and C6326T (Q2039X) mutations in exon 15, each resulting in a nonsense termination; −G7205-G7211 in exon 16, resulting in a FS2331; a C7415T (R2402X) mutation in exon 18, resulting in a nonsense termination; a C7883T (Q2558X) mutation in exon 19, resulting in a nonsense termination; and a −C8159-T8160 mutation in exon 21, resulting in a FS2649 (Phakdeekitcharoen et al., supra, 2000). In addition, probable pathogenic mutations including G3707A (G1166S) and T6078A (V1956E) missense mutations in exon 15, and a C7433T (R2408C) missense mutation and an insertion of a GCG trinucleotide between G7535 and G7536 (extra Gly2422) in exon 18 have been identified (Phakdeekitcharoen et al., supra, 2000).

Four additional mutations unique to one of the families also were identified (see Table 3). The mutants segregate with disease, and were not observed in a screen of over 100 normal That chromosomes. Three of the four variants are predicted to result in non-conservative amino acid substitutions. Two of them (A9164G, C9326T) are present in the same allele of a single family (RAMA87). As such, these mutations meet several criteria expected of disease-producing mutations, including they are not found in normal, ethnically matched chromosomes, they segregate with the disease, and they result in non-conservative substitutions.

In one case a heteroduplex pattern was discovered for the exon 22 product of the proband by standard agarose electrophoresis. The heteroduplex pattern was confirmed to segregate with disease and subsequently determined that the novel variant was the result of a T to G transversion at position 8298. This mutation is predicted to substitute arginine for leucine at position 2696 of the protein sequence. This non-conservative substitution is within the REJ domain. Interestingly, the R3039C substitution occurs near a newly described putative proteolytic cleavage site of polycystin-1, His(3047)-Leu-Thr-Ala(3050) (SEQ ID NO:59). In the corresponding position of Fugu and murine polycystin-1, glutamic acid and arginine, respectively, are present, suggesting a non-critical role for a non-polar residue at this location.

Seven nucleotide substitutions that are likely normal variants were also identified. Two are missense variants that do not segregate with disease in the family in which they were discovered. The C474T substitution results in the conservative replacement of valine by alanine at position 88 in the first leucine rich (LRR) repeat. The amino acid is not conserved between species and is not predicted to disrupt the LRR structure. The second missense variant, A10143G, substitutes arginine for histidine at position 3311 within the first extracellular loop between TM2 and TM3. It too, is a conservative change involving a residue whose identity is not evolutionarily conserved at this position. The other five variants were silent nucleotide substitutions that were unique to the pedigree in which they were found and not found in more than 100 normal chromosomes. It is possible that these variants can be pathogenic by affecting gene splicing in the region. Two of the normal variants of exon 30, A10143G (H3311R) and T10234C (L3341L), were clustered together in a single PKD1 haplotype. Interestingly, both variants also are present in at least one of the homologues, suggesting a previous gene conversion event as the original of these PKD1 variants. Additional PKD1 variants, which do not appear to be associated with a PKD1-associated disorder, include two silent mutations, G4885A (T1558T) and C6058T (S1949S), and a missense mutation, G6195A (R1995H), in exon 15; a silent T7376C (L2389L) mutation in exon 17; a silent C7696T (C2495C) mutation in exon 18; and a missense G8021A (D2604N) mutation in exon 20 (Phakdeekitcharoen et al., supra, 2000).

Table 4 summarizes the clinical findings for the probands of 17 That families. The genotypes and phenotypes for patients with ADPKD are shown. It has been estimated on the basis of studies of Caucasian populations that approximately 15% of mutations are localized to the nonreplicated portion of the PKD1 gene. If the same frequency is true for the That population (the patients were not screened for mutations in the nonreiterated portion), then the present studies have identified approximately 45% to 54 percent of all mutations present in the nonreplicated region. This detection rate likely can be increased by using more sensitive detection methods such as DHPLC (Kristensen et al., supra, 2001), HTCSGD (Leung et al., supra, 2001), or the like.

TABLE 4

Genotypes and Phenotypes in Thai ADPKD1

| | | | Genotype | | Phenotype | | | | | | | |
|---|---|---|---|---|---|---|---|---|---|---|---|---|
| Patients | Age | Exon | Codon Change | Consequence | HT | Renal insuff. (Cr > 2) | Renal stone | Palpable kidneys | Liver Cyst | Heart Valv. Abnorm. | Brain Aneur | Ref. |
| RAMA28-0 | 30 | 12 | W967R | Missense | + | − | − | − | − | − | − | |
| RAMA103- | 57 | 13 | FS after 1041 | Frameshift | + | − | + | − | + | − | − | (*) |
| RAMA49-0 | 26 | 15 | G1166S | Missense | + | − | − | + | − | − | − | (*) |
| RAMA36-0 | 47 | 15 | Q1653X | Nonsense | + | − | − | + | | − | − | (*) |
| RAMA108- | 57 | 15 | V1956E | Missense | + | + | − | − | | − | − | (*) |
| RAMA77-0 | 53 | 15 | Q1960X | Nonsense | + | + | − | + | + | − | − | (*) |
| RAMA32-0 | 36 | 15 | Q2039X | Nonsense | + | + | − | + | | − | − | (*) |
| RAMA97-0 | 45 | 17 | R2402X | Nonsense | + | + | − | − | | − | − | (*) |
| RAMA96-0 | 30 | 18 | R2408C | Missense | − | − | + | − | + | − | − | (*) |
| RAMA99-0 | 56 | 18 | R2430X | Nonsense | + | + | + | − | + | − | − | (*) |
| RAMA66-0 | 39 | 18 | 2442 add'l. Gly | Extra Glycine | + | − | + | − | − | − | − | (*) |
| RAMA55-0 | 52 | 19 | Q2558X | Nonsense | − | − | − | + | + | − | − | (*) |
| RAMA5-01 | 53 | 21 | FS after 2649 | Frameshift | + | + | + | + | + | + | + | (*) |
| RAMA3-02 | 40 | 22 | L2696R | Missense | + | + | − | + | + | − | − | |
| RAMA87-0 | 61 | 25 | R2985G | Missense | − | − | − | + | + | − | − | |
| | | 25 | R3039C | Missense | | | | | | − | − | |
| RAMA59-0 | 35 | 25 | W3001X | Nonsense | + | + | + | − | − | − | − | |
| RAMA45-0 | 59 | 29 | V32851 | Missense | + | + | − | − | − | − | − | |

HT—hypertension; Renal insuff.—renal insufficiency; Heart Valv. Abnorm.—heart valvular abnormalities; Brain Aneur.—brain aneurisyms; (*) Phakdeekitcharoen et al., supra, 2000.

Although the invention has been described with reference to the above examples, it will be understood that modifications and variations are encompassed within the spirit and scope of the invention. Accordingly, the invention is limited only by the following claims.

What is claimed is:

1. A method of amplifying a PKD1-specific polynucleotide, comprising:

(a) contacting a PKD1 polynucleotide in a biological sample obtained from a human with a primer that selectively hybridizes to a nucleotide sequence within a polycystic kidney disease-associated protein-1 (PKD1) gene sequence to produce a PKD1-specific amplification product; and (b) amplifying the PKD1 polynucleotide to obtain a PKD1-specific amplification product, wherein the primer selectively hybridizes to a PKD1 gene sequence as set forth in SEQ ID NO:1, and wherein the primer is selected from the group consisting of SEQ ID NOs: 3, 5, 8, 14, 16 and 17.

2. The method of claim 1, wherein amplifying the PKD1 polynucleotide to obtain a PKD1-specific amplification product comprises the use of a primer pair selected from SEQ ID NOS:3 and 4; SEQ ID NOS:5 and 6; SEQ ID NOS:7 and 8; SEQ ID NOS:13 and 14; SEQ ID NOS:15 and 16; and SEQ ID NOS:17 and 18.

3. The method of claim 1, further comprising performing a nested PCR reaction by contacting the PKD1-specific amplification product with a primer set under conditions suitable to perform nested PCR to obtain a nested PCR product.

4. The method of claim 3, further comprising a dilution step, to remove genomic contamination from the amplification products, prior to the nested PCR reaction.

5. The method of claim 3, wherein the primer set comprises one or more oligonucleotide selected from the group consisting of SEQ ID NOs: 28, 43, 48, 51, 60, 61, 63, 100 and 102.

6. The method of claim 1, wherein amplifying the PKD1 polynucleotide to obtain a PKD1-specific amplification product comprises the use of one or more oligonucleotides selected from the group consisting of SEQ ID NOs: 6, 14 and 17.

* * * * *

UNITED STATES PATENT AND TRADEMARK OFFICE

CERTIFICATE OF CORRECTION

PATENT NO. : 9,670,543 B2
APPLICATION NO. : 13/965083
DATED : June 6, 2017
INVENTOR(S) : Gregory G. Germino, Terry J. Watnick and Bunyong Phakdeekitcharoen It is certified that error appears in the above-identified patent and that said Letters Patent is hereby corrected as shown below:

In the Specification

Column 1, Lines 14-17 second paragraph (government support statement) please replace with the following:
STATEMENT OF GOVERNMENTAL INTEREST
This invention was made with government support under grant numbers DK048006, TW005393, DK002562, awarded by the National Institutes of Health. The government has certain rights in the invention.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*